US012027027B2

(12) United States Patent
Pham et al.

(10) Patent No.: US 12,027,027 B2
(45) Date of Patent: Jul. 2, 2024

(54) DETECTING FALLS USING A MOBILE DEVICE

(71) Applicant: Apple Inc., Cupertino, CA (US)

(72) Inventors: Hung A. Pham, Oakland, CA (US); Stephen P. Jackson, San Francisco, CA (US); Vinay R. Majjigi, Mountain View, CA (US); Karthik Jayaraman Raghuram, Mountain View, CA (US); Adeeti V. Ullal, Mountain View, CA (US); Yann Jerome Julien Renard, San Carlos, CA (US); Telford Earl Forgety, III, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/945,977

(22) Filed: Sep. 15, 2022

(65) Prior Publication Data

US 2023/0042265 A1   Feb. 9, 2023

Related U.S. Application Data

(63) Continuation of application No. 16/929,043, filed on Jul. 14, 2020, now Pat. No. 11,527,140, which is a (Continued)

(51) Int. Cl.
*G08B 1/08* (2006.01)
*A61B 5/00* (2006.01)
(Continued)

(52) U.S. Cl.
CPC .......... *G08B 21/0446* (2013.01); *A61B 5/002* (2013.01); *A61B 5/0205* (2013.01);
(Continued)

(58) Field of Classification Search
CPC ...................... G08B 21/0446; G08B 13/2454; A61B 5/002; A61B 5/0205; A61B 5/024;
(Continued)

(56) References Cited

U.S. PATENT DOCUMENTS 8,206,325 B1   6/2012   Najafi et al.
8,217,795 B2   7/2012   Carlton-Foss
(Continued)

FOREIGN PATENT DOCUMENTS

CN   102186420   9/2011
CN   102903207   1/2013
(Continued)

OTHER PUBLICATIONS

Fortino et al., "Fall-MobileGuard: Smart real-time fall detection system," EAI International Conference on Body Area Networks, Sep. 28, 2015, pp. 44-50.
(Continued)

*Primary Examiner* — Toan N Pham
(74) *Attorney, Agent, or Firm* — Fish & Richardson P.C.

(57) ABSTRACT

In an example method, a mobile device obtains sample data generated by one or more sensors over a period of time, where the one or more sensors are worn by a user. The mobile device determines that the user has fallen based on the sample data, and determines, based on the sample data, a severity of an injury suffered by the user. The mobile device generates one or more notifications based on the determination that the user has fallen and the determined severity of the injury.

20 Claims, 39 Drawing Sheets

Related U.S. Application Data continuation-in-part of application No. 16/852,370, filed on Apr. 17, 2020, now Pat. No. 11,276,290, which is a continuation of application No. 16/128,464, filed on Sep. 11, 2018, now Pat. No. 10,629,048.

(60) Provisional application No. 62/565,988, filed on Sep. 29, 2017.

(51) Int. Cl.

| | | |
|---|---|---|
| *A61B 5/0205* | (2006.01) | |
| *A61B 5/024* | (2006.01) | |
| *A61B 5/11* | (2006.01) | |
| *G01C 5/06* | (2006.01) | |
| *G01C 21/12* | (2006.01) | |
| *G01S 19/13* | (2010.01) | |
| *G06F 3/01* | (2006.01) | |
| *G08B 13/24* | (2006.01) | |
| *G08B 21/04* | (2006.01) | |

(52) U.S. Cl.
CPC ............ *A61B 5/024* (2013.01); *A61B 5/1112* (2013.01); *A61B 5/1117* (2013.01); *A61B 5/1121* (2013.01); *A61B 5/1123* (2013.01); *A61B 5/681* (2013.01); *A61B 5/7246* (2013.01); *A61B 5/7264* (2013.01); *A61B 5/7405* (2013.01); *A61B 5/742* (2013.01); *A61B 5/7455* (2013.01); *A61B 5/746* (2013.01); *A61B 5/747* (2013.01); *G01C 5/06* (2013.01); *G01C 21/12* (2013.01); *G01S 19/13* (2013.01); *G06F 3/011* (2013.01); *G08B 13/2454* (2013.01); *A61B 2503/10* (2013.01); *A61B 2560/0242* (2013.01); *A61B 2562/0219* (2013.01)

(58) Field of Classification Search
CPC ... A61B 5/1112; A61B 5/1117; A61B 5/1121; A61B 5/1123; A61B 5/681; A61B 5/7246; A61B 5/7264; A61B 5/7405; A61B 5/742; A61B 5/7455; A61B 5/746; A61B 5/747; A61B 2503/10; A61B 2560/0242; A61B 2562/0219; G01S 19/13; G06F 3/011; G01C 5/06; G01C 21/12

See application file for complete search history.

(56) References Cited

U.S. PATENT DOCUMENTS

| | | | |
|---|---|---|---|
| 8,909,497 | B1 | 12/2014 | Shkolnikov |
| 9,179,864 | B2 | 11/2015 | Otto et al. |
| 9,342,108 | B2 | 5/2016 | Rothkopf et al. |
| 9,597,004 | B2 | 3/2017 | Hughes et al. |
| 9,640,057 | B1 | 5/2017 | Ross |
| 9,773,397 | B2* | 9/2017 | Ten Kate ............... A61B 5/746 |
| 9,818,282 | B2* | 11/2017 | Burton ................ G08B 25/10 |
| 9,959,733 | B2* | 5/2018 | Gu ..................... G08B 21/0446 |
| 10,147,296 | B2 | 12/2018 | Gregg |
| 10,226,204 | B2 | 3/2019 | Heaton |
| 10,629,048 | B2 | 4/2020 | Tan et al. |
| 10,692,011 | B2 | 6/2020 | Pathak et al. |
| 10,950,112 | B2 | 3/2021 | Kate et al. |
| 11,276,290 | B2 | 3/2022 | Tan et al. |
| 11,282,361 | B2 | 3/2022 | Sharma et al. |
| 11,282,362 | B2 | 3/2022 | Tan et al. |
| 11,282,363 | B2 | 3/2022 | Tan et al. |
| 11,527,140 | B2 | 12/2022 | Pham et al. |
| 11,842,615 | B2 | 12/2023 | Tan et al. |
| 2008/0001735 | A1 | 1/2008 | Tran |
| 2009/0322540 | A1 | 12/2009 | Richardson et al. |
| 2012/0101411 | A1 | 4/2012 | Hausdorff et al. |
| 2012/0259577 | A1 | 10/2012 | Ganyi |
| 2012/0314901 | A1 | 12/2012 | Hanson et al. |
| 2013/0054180 | A1 | 2/2013 | Barfield |
| 2013/0120147 | A1 | 5/2013 | Narasimhan et al. |
| 2013/0143519 | A1 | 6/2013 | Doezema |
| 2014/0100487 | A1 | 4/2014 | McNair |
| 2014/0375461 | A1 | 12/2014 | Richardson et al. |
| 2015/0269824 | A1 | 9/2015 | Zhang |
| 2016/0113551 | A1 | 4/2016 | Annegam et al. |
| 2016/0220153 | A1 | 8/2016 | Annegam et al. |
| 2016/0260311 | A1 | 9/2016 | Asano |
| 2017/0055851 | A1 | 3/2017 | Al-Ali |
| 2017/0193787 | A1 | 7/2017 | Devdas et al. |
| 2017/0200359 | A1 | 7/2017 | Gregg |
| 2018/0000385 | A1 | 1/2018 | Heaton et al. |
| 2018/0070889 | A1* | 3/2018 | Lee ................... G08B 21/0446 |
| 2018/0177436 | A1 | 6/2018 | Chang et al. |
| 2018/0247713 | A1 | 8/2018 | Rothman |
| 2018/0333083 | A1 | 11/2018 | Orellano |
| 2019/0099114 | A1 | 4/2019 | Mouradian et al. |
| 2019/0103007 | A1 | 4/2019 | Tan et al. |
| 2019/0200915 | A1 | 7/2019 | Baker et al. |
| 2019/0320945 | A1 | 10/2019 | Johnson et al. |
| 2020/0205697 | A1 | 7/2020 | Zheng et al. |
| 2020/0250954 | A1 | 8/2020 | Tan et al. |
| 2020/0342735 | A1 | 10/2020 | Tan et al. |
| 2020/0342736 | A1 | 10/2020 | Tan et al. |
| 2020/0342737 | A1 | 10/2020 | Pham et al. |
| 2021/0005071 | A1 | 1/2021 | Sharma et al. |
| 2022/0036714 | A1 | 2/2022 | Tan et al. |
| 2023/0011207 | A1 | 4/2023 | Khalak et al. |
| 2023/0112071 | A1 | 4/2023 | Khalak et al. |
| 2024/0127683 | A1 | 4/2024 | Tan et al. |

FOREIGN PATENT DOCUMENTS

| | | |
|---|---|---|
| CN | 103593944 | 2/2014 |
| CN | 104055518 | 9/2014 |
| CN | 104504855 | 4/2015 |
| CN | 105448040 | 3/2016 |
| CN | 105530865 | 4/2016 |
| CN | 105769205 | 7/2016 |
| CN | 106037749 | 10/2016 |
| CN | 106530611 | 3/2017 |
| CN | 107123239 | 9/2017 |
| CN | 107205679 | 9/2017 |
| CN | 107233099 | 10/2017 |
| CN | 107305645 | 10/2017 |
| CN | 108257679 | 7/2018 |
| CN | 111132603 | 5/2020 |
| CN | 111383420 | 7/2020 |
| JP | 2007507320 | 3/2007 |
| JP | 2011521349 | 7/2011 |
| JP | 2016512777 | 5/2016 |
| JP | 2016529081 | 9/2016 |
| JP | 2016177437 | 10/2016 |
| JP | 2016177449 | 10/2016 |
| KR | 1020110071212 | 6/2011 |
| WO | WO 2012/146957 | 11/2012 |
| WO | WO 2015/087164 | 6/2015 |

OTHER PUBLICATIONS

Shahzad et al., "FallDroid: An Automated Smart-Phone-Based Fall Detection System Using Multiple Kernel Learning," IEEE Transactions of Industrial Informatics, May 23, 2018, 11 pages.

'who.com' [online], "Falls," Published on Jan. 16, 2018, [retrieved on Mar. 15, 2019], retrieved from the Internet: URL:<https://www.who.int/en/news-room/fact-sheets/detail/falls>. 4 pages.

Yongkun et al., "A New Smart Fall-down Detector for Senior Healthcare System Using Inertial Micro sensors," 2014 36th Annual International Conference of the IEEE Engineering in Medicine and Biology Society, Aug. 26, 2014, pp. 590-593.

(56) References Cited

OTHER PUBLICATIONS

Shahiduzzaman et al., "Fall Detection by Accelerometer and Heart Rate Variability Measurement," Global Journal of Computer Science and Technology: G Interdisciplinary, Dec. 31, 2015, 15(3), 7 pages.

* cited by examiner

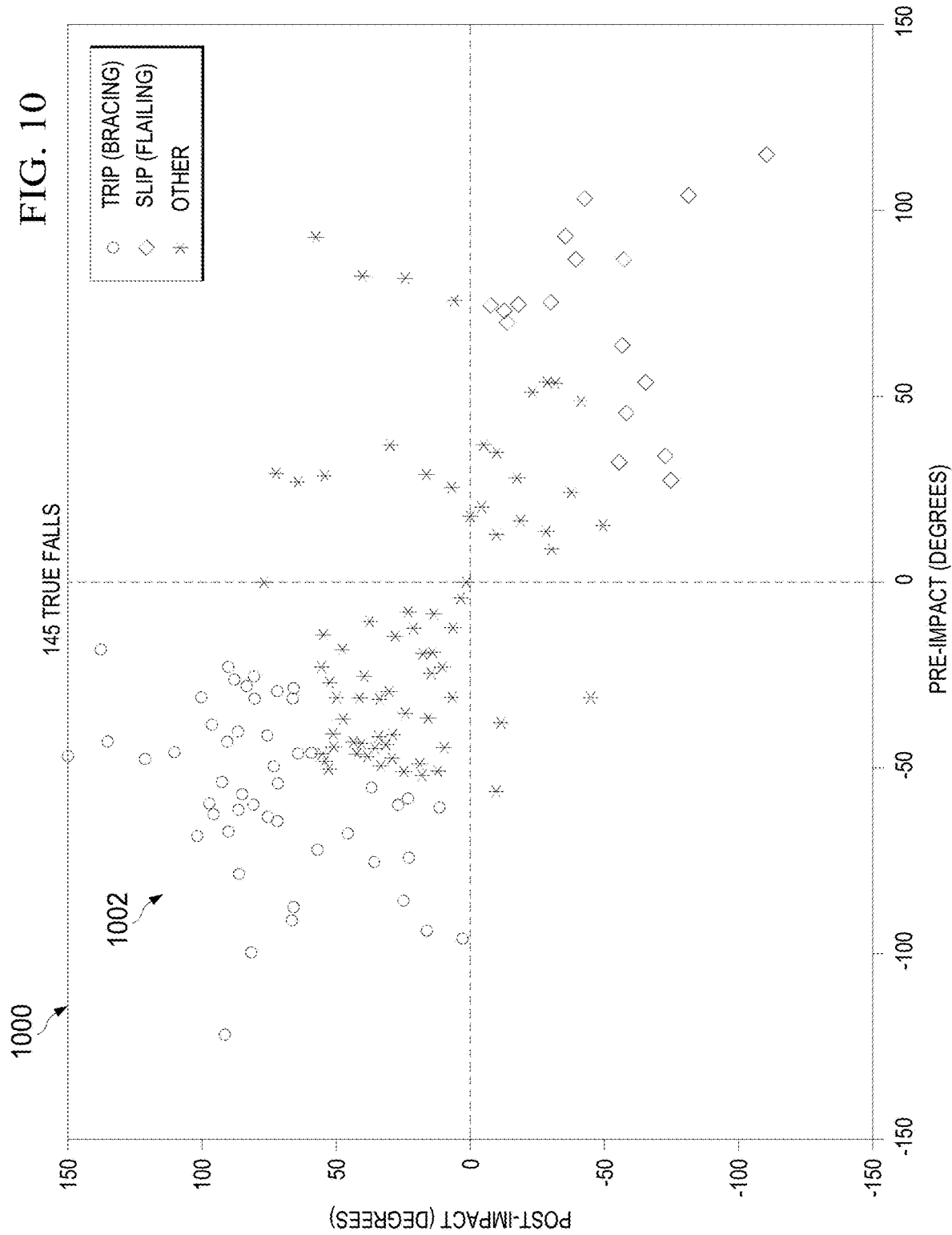

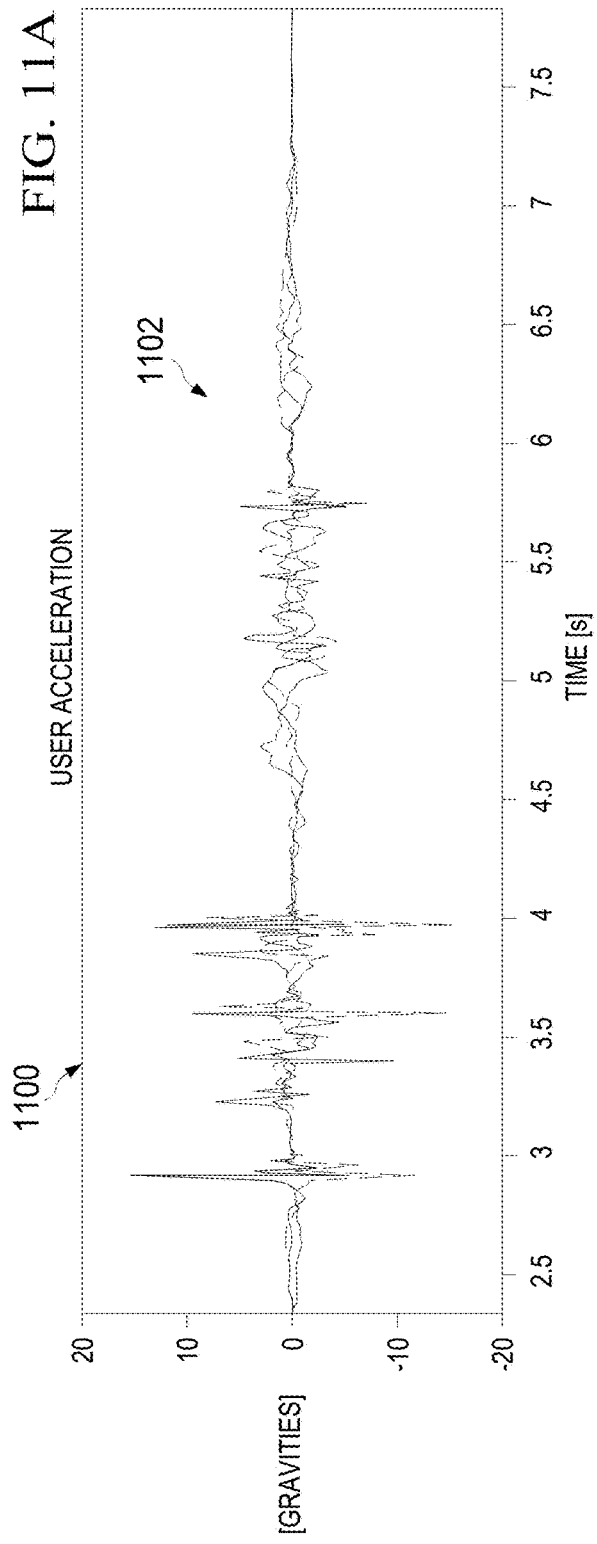
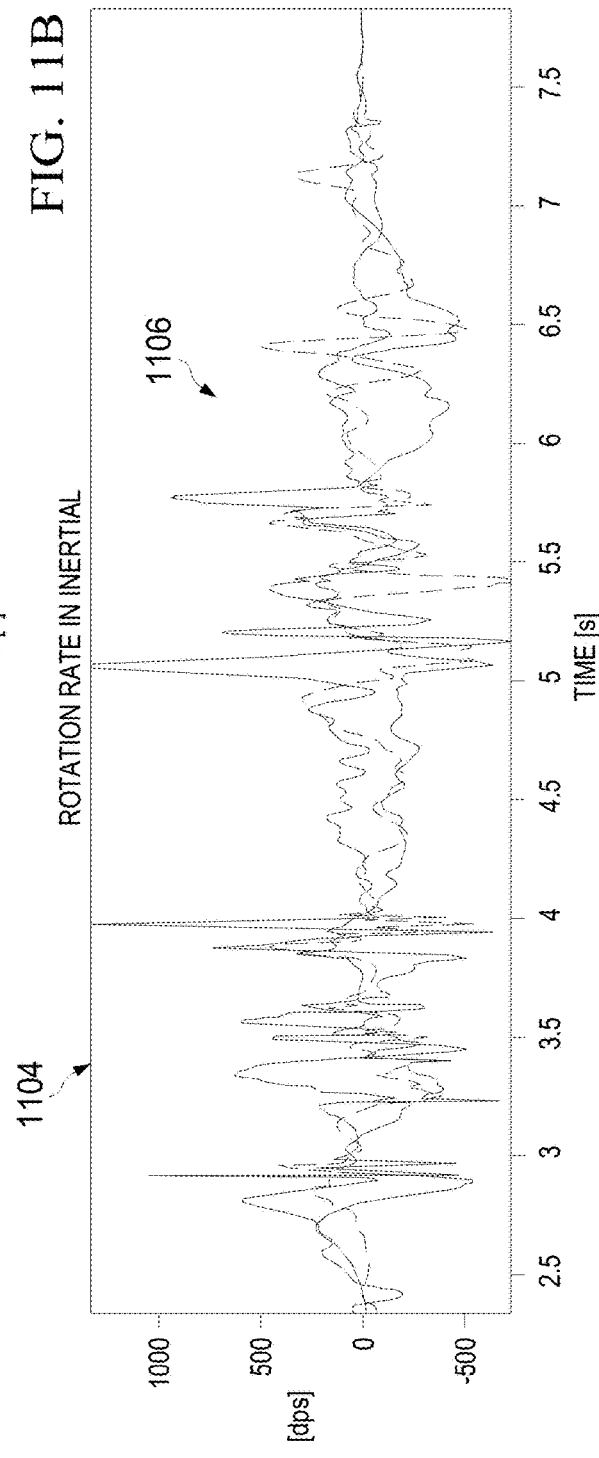

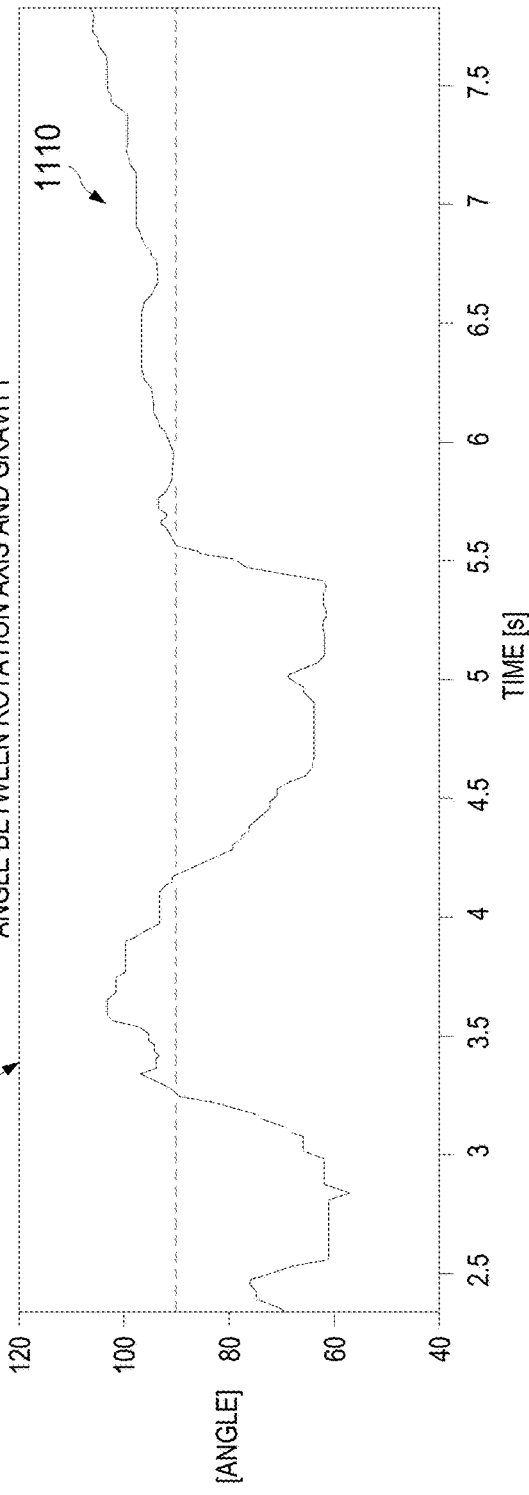
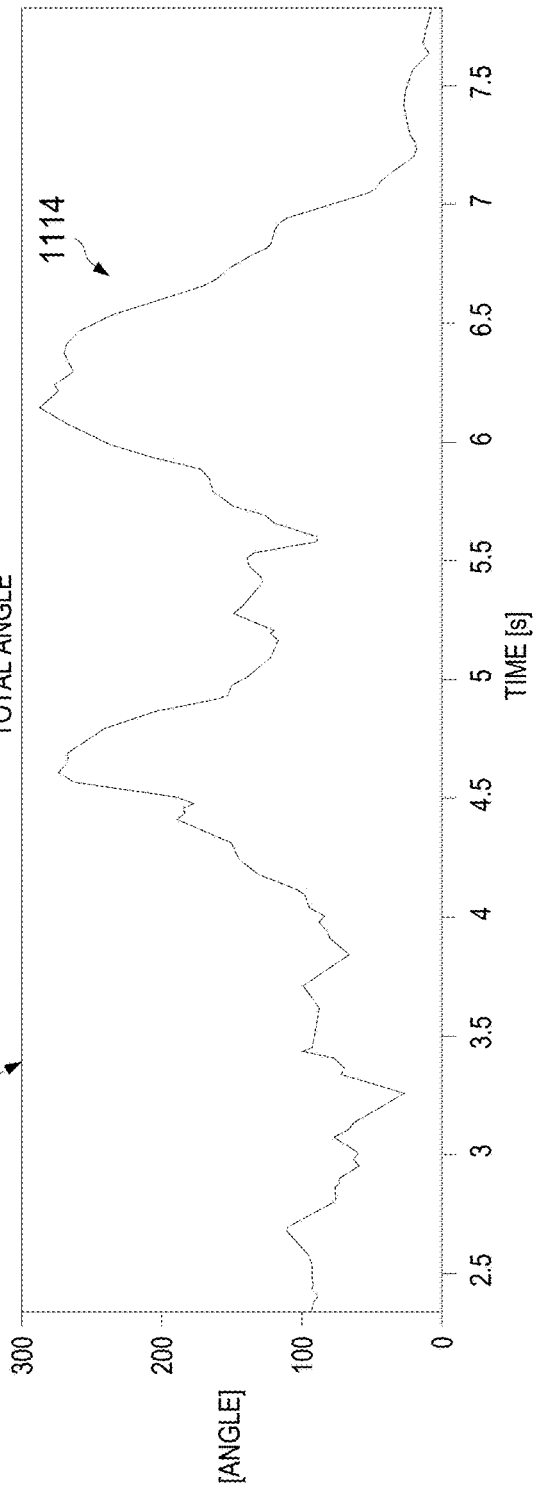

DETECTING FALLS USING A MOBILE DEVICE

CROSS-REFERENCE TO RELATED APPLICATION

This application is a continuation of U.S. patent application Ser. No. 16/929,043, filed Jul. 14, 2020, now U.S. Pat. No. 11,527,140, which is a continuation-in-part of U.S. patent application Ser. No. 16/852,370, filed Apr. 17, 2020, now U.S. Pat. No. 11,276,290, which is a continuation of U.S. application Ser. No. 16/128,464, filed Sep. 11, 2018, now U.S. Pat. No. 10,629,048, which claims priority to U.S. Provisional Application No. 62/565,988, filed Sep. 29, 2017, the entire contents of each of which are incorporated herein by reference.

TECHNICAL FIELD

The disclosure relates to techniques for determining whether a user has fallen using a mobile device.

BACKGROUND

A motion sensor is a device that measures the motion experienced by an object (e.g., the velocity or acceleration of the object with respect to time, the orientation or change in orientation of the object with respect to time, etc.). In some cases, a mobile device (e.g., a cellular phone, a smart phone, a tablet computer, a wearable electronic device such as a smart watch, etc.) can include one or more motion sensors that determine the motion experienced by the mobile device over a period of time. If the mobile device is worn by a user, the measurements obtained by the motion sensor can be used to determine the motion experienced by the user over the period of time.

SUMMARY

Systems, methods, devices and non-transitory, computer-readable mediums are disclosed for electronically determining whether a user has fallen using a mobile device.

In an aspect, a method includes obtaining, by a mobile device, motion data indicating motion measured by a motion sensor over a time period. The motion sensor is worn or carried by a user. The method also includes determining, by the mobile device, an impact experienced by the user based on the motion data, the impact occurring during a first interval of the time period. The method also includes determining, by the mobile device based on the motion data, one or more first motion characteristics of the user during a second interval of the time period. The second interval occurs prior to the first interval. The method also includes determining, by the mobile device based on the motion data, one or more second motion characteristics of the user during a third interval of the time period. The third interval occurs after the first interval. The method also includes determining, by the mobile device, that the user has fallen based on the impact, the one or more first motion characteristics of the user, and the one or more second motion characteristics of the user, and responsive to determining that the user has fallen, generating, by the mobile device, a notification indicating that the user has fallen.

Implementations of this aspect can include one or more of the following features.

In some implementations, determining the one or more first motion characteristics can include determining, based on the motion data, that the user was walking during the second interval.

In some implementations, determining the one or more first motion characteristics can include determining, based on the motion data, that the user was ascending or descending stairs during the second interval.

In some implementations, determining the one or more first motion characteristics can include determining, based on the motion data, that the user was moving a body part according to a flailing motion or a bracing motion during the second interval.

In some implementations, determining the one or more second motion characteristics can include determining, based on the motion data, that the user was walking during the third interval.

In some implementations, determining the one or more second motion characteristics can include determining, based on the motion data, that the user was standing during the third interval.

In some implementations, determining the one or more second motion characteristics can include determining, based on the motion data, that an orientation of a body part of the user changed N or more times during the third interval.

In some implementations, determining that the user has fallen can include determining, based on the motion data, that the impact is greater than a first threshold value, and determining, based on the motion data, that a motion of the user was impaired during the third interval.

In some implementations, determining that the user has fallen can include determining, based on the motion data, that the impact is less than a first threshold value and greater than a second threshold value, determining, based on the motion data, that the user was at least one of walking during the second interval, ascending stairs during the second interval, or descending stairs during the second interval, determining, based on the motion data, that the user was moving a body part according to a flailing motion or a bracing motion during the second interval, and determining, based on the motion data, that a motion of the user was impaired during the third interval.

In some implementations, generating the notification can include presenting an indication that the user has fallen on at least one of a display device or an audio device of the mobile device.

In some implementations, generating the notification can include transmitting data to a communications device remote from the mobile device, the data comprising an indication that the user has fallen.

In some implementations, determining that the user has fallen can include generating a statistical model based on one or more sampled impacts, one or more sampled first motion characteristics, and one or more sampled second motion characteristics. The one or more sampled impacts, the one or more sampled first motion characteristics, and the one or more sampled second motion characteristics can be determined based on sample motion data. The sample motion data can indicate motion measured by one or more additional sensors over one or more additional time periods, where each additional motion sensor is worn by a respective additional user.

In some implementations, the statistical model can be a Bayesian statistical model.

In some implementations, the one or more sampled first motion characteristics can include an indication of a type of activity being performed by a particular additional user with respect to the sample motion data, an indication of an activity level of a particular additional user with respect to the sample motion data, and/or an indication of a walking speed of a particular additional user with respect to the sample motion data.

In some implementations, the method can be performed by a co-processor of the mobile device. The co-processor can be configured to receive motion data obtained from one or more motion sensors, process the motion data, and provide the processed motion data to one or more processors of the mobile device.

In some implementations, the mobile device can include the motion sensor.

In some implementations, the mobile device can be worn on an arm or a wrist of the user while the motion is being measured by the sensor.

In some implementations, the mobile device can be a wearable mobile device.

In another aspect, a method includes obtaining, by a mobile device, a first signal indicating an acceleration measured by an accelerometer over a time period, and a second signal indicating an orientation measured by an orientation sensor over the time period, wherein the accelerometer and the orientation sensor are physically coupled to a user. The method also includes determining, by the mobile device, rotation data indicating an amount of rotation experienced by the user during the time period, determining, by the mobile device, that the user has tumbled based on the rotation data, and responsive to determining that the user has tumbled, generating, by the mobile device, a notification indicating that the user has tumbled.

Implementations of this aspect can include one or more of the following features.

In some implementations, the rotation data can include a third signal indicating a rotation rate experienced by the user during the time period.

In some implementations, the rotation data can include an indication of one or more rotational axes of the rotation in a reference coordinate system by the user during the time period.

In some implementations, the rotation data can include an indication of an average rotational axis of the rotation by the user during the time period.

In some implementations, determining that the user has tumbled can include determining a variation between the one or more rotational axes of the rotation by the user during the time period and the average rotational axis of the rotation by the user during the time period.

In some implementations, determining that the user has tumbled can include determining that the variation is less than a first threshold value, and responsive to determining that the variation is less than the first threshold value, determining a fourth signal corresponding to an angular displacement of the user during the time period based on the third signal.

In some implementations, determining the fourth signal can include integrating the third signal with respect to the period of time.

In some implementations, determining that the user has tumbled can include determining that the angular displacement of the user during the period of time is greater than a second threshold value, determining that at least one of the one or more rotational axes of the rotation by the user during the time period is greater than a third threshold value, and responsive to determining that the angular displacement experienced of the user during the period of time is greater than the second threshold value and determining that at least one of the one or more rotational axes of the rotation by the user during the time period is greater than the third threshold value, determining that the user has tumbled.

In some implementations, generating the notification can include presenting an indication that the user has tumbled on at least one of a display device or an audio device of the mobile device.

In some implementations, generating the notification can include transmitting data to a communications device remote from the mobile device, the data comprising an indication that the user has tumbled.

In some implementations, the method can be performed by a co-processor of the mobile device. The co-processor can be configured to receive motion data obtained from one or more sensors, process the motion data, and provide the processed motion data to one or more processors of the mobile device.

In another aspect, a method includes obtaining, by a mobile device, motion data indicating a motion measured by one or more motion sensors over a first time period. The one or more motion sensors are worn by a user. The method also includes determining, by the mobile device, that the user has fallen based on the motion data, and responsive to determining that the user has fallen, generating, by the mobile device, one or more notifications indicating that the user has fallen.

Implementations of this aspect can include one or more of the following features.

In some implementations, generating the one or more notifications can include presenting a first notification to the user indicating that the user has fallen.

In some implementations, the first notification can include at least one of a visual message, an audio message, or a haptic message.

In some implementations, generating the one or more notifications can include receiving, by the mobile device, an input from the user in response to the first notification. The input can indicate a request for assistance by the user. Further, generating the one or more notifications can include, responsive to receiving the input, transmitting a second notification indicating the request for assistance to a communications device remote from the mobile device.

In some implementations, the communications device can be an emergency response system.

In some implementations, the second notification can indicate a location of the mobile device.

In some implementations, generating the one or more notifications can include determining, by the mobile device, an absence of movement by the user during a second time period after the user has fallen, and responsive to determining the absence of movement by the user during the second time period, transmitting a second notification indicating a request for assistance to a communications device remote from the mobile device.

In some implementations, generating the one or more notifications can include determining, by the mobile device, that the user has moved during a second time period after the user has fallen, and responsive to determining that the user has moved during the second time period, refraining from transmitting a second notification indicating a request for assistance to a communications device remote from the mobile device.

In some implementations, the one or more notifications can be generated according to a state machine.

In some implementations, the one or more motion sensors can include at least one of an accelerometer or a gyroscope.

In some implementations, the mobile device can be a wearable mobile device.

In some implementations, determining that the user has fallen can include determining that the user experienced an impact based on the motion data.

In some implementations, determining that the user has fallen can include determining a behavior of the user during the first time period.

In another aspect, a method includes obtaining, by a mobile device, sample data generated by a plurality of sensors over a time period. The plurality of sensors is worn by a user. The sample data includes motion data indicating a motion of the user obtained from one or more motion sensors of the plurality of sensors, and at least one of location data indicating a location of the mobile device obtained from one or more location sensors of the plurality of sensors, altitude data indicating an altitude of the mobile device obtained from one or more altitude sensors of the plurality of sensors, or heart rate data indicating a heart rate of the user obtained from one or more heart rate sensor of the plurality of sensors. The method also includes determining, by the mobile device, that the user has fallen based on the sample data, and responsive to determining that the user has fallen, generating, by the mobile device, one or more notifications indicating that the user has fallen.

Implementations of this aspect can include one or more of the following features.

In some implementations, the one or more motion sensors can include at least one of an accelerometer or a gyroscope.

In some implementations, obtaining the motion data can include obtaining acceleration data using the accelerometer during a first time interval during the period of time. The gyroscope can be disabled during the first time interval. Obtaining the motion data can further include determining, based on the acceleration data obtained during the first time interval, that a movement of a user exceeded a threshold level during the first time interval, and responsive to determining that the movement of the user exceeded the threshold level during the first time interval, obtaining acceleration data using the accelerometer and gyroscope data using the gyroscope during a second time interval after the first time interval.

In some implementations, the one or more altitude sensors can include at least one of an altimeter or a barometer.

In some implementations, the one or more location sensors can include at least one of a wireless transceiver or a global Navigation Satellite System receiver.

In some implementations, determining that the user has fallen can include determining, based on the motion data, a change in orientation of the mobile device during the period of time, and determining that the user has fallen based on the change in orientation.

In some implementations, determining that the user has fallen can include determining, based on the motion data, an impact experienced by the user during the period of time, and determining that the user has fallen based on the impact.

In some implementations, determining that the user has fallen can include determining, based on the altitude data, a change in altitude of the mobile device during the period of time, and determining that the user has fallen based on the change in altitude.

In some implementations, determining that the user has fallen can include determining, based on the heart rate data, a change in heart rate of the user during the period of time, and determining that the user has fallen based on the change in heart rate.

In some implementations, determining the change in heart rate of the user during the period of time can include determining a rate of decay of the heart rate of the user during the period of time.

In some implementations, determining that the user has fallen can include determining, based on the location data, an environmental condition at the location of the mobile device, and determining that the user has fallen based on the environment conditional.

In some implementations, the environmental condition can be weather.

In some implementations, the mobile device can determine that the user has fallen based on the motion data, the location data, the altitude data, and the heart rate data.

In some implementations, the mobile device can be a wearable mobile device.

In some implementations, generating the one or more notifications can include transmitting a notification to a communications device remote from the mobile device.

In some implementations, the communications device can be an emergency response system.

In another aspect, a method includes receiving, by a mobile device, motion data obtained by one or more sensors over a time period, where the one or more sensors are worn by a user; determining, by the mobile device based on the motion data, an impact experienced by the user during the time of period; determining, by the mobile device, one or more of characteristics of the user; determining, by the mobile device based on the motion data and the one or more characteristics of the user, a likelihood that the user requires assistance subsequent to the impact; and generating, by the mobile device, one or more notifications based on likelihood.

Implementations of this aspect can include one or more of the following features.

In some implementations, the one or more characteristics of the user can include an age of the user. The likelihood can increase with an increase in the age of the user.

In some implementations, the one or more characteristics of the user can include a gender of the user. The likelihood can depend on the gender of the user.

In some implementations, the one or more characteristics of the user can include a historical physical activity level of the user. The likelihood can increase with a decrease in the historical physical activity level of the user. In some implementations, the historical physical activity level can be indicative of a frequency of movement by the user prior to the impact. In some implementations, the historical physical activity level can be indicative of an intensity of movement by the user prior to the impact.

In some implementations, the one or more characteristics of the user can include a vascular health of the user. The likelihood can increase with a decrease in the vascular health of the user. In some implementations, the vascular health of the user can be determined based on a maximal oxygen uptake ($VO_2$ max) of the user.

In some implementations, the one or more characteristics of the user can include a historical walking speed of the user. The likelihood can increase with a decrease in the historical walking speed of a user.

In some implementations, generating the one or more notifications can include determining that the likelihood exceeds a threshold level, and responsive to determining that the likelihood exceeds the threshold level, generating the one or more notifications.

In some implementations, generating the one or more notifications can include transmitting a first notification to a communications device remote from the mobile device, the first notification comprising an indication that the user has fallen. The communications device can be an emergency response system.

In some implementations, the mobile device can be a wearable mobile device.

In some implementations, at least some of the one or more sensors can be disposed on or in the mobile device.

In some implementations, at least some of the one or more sensors can be remote from the mobile device.

In another aspect, a method includes obtaining, by a mobile device, a database including a plurality of data records. Each data record includes an indication of a respective impact previously experienced by a user of the mobile device, and sensor data generated by one or more first sensors worn by the user during that impact. The method also includes obtaining, by the mobile device, additional sensor data generated by one or more second sensors worn by the user over a period of time; determining, by the mobile device, whether the user has fallen during the period of time based on the database and the additional sensor data; and generating, by the mobile device, one or more notifications based on the determination of whether the user has fallen during the period of time.

Implementations of this aspect can include one or more of the following features.

In some implementations, the method can include generating an additional data record based the additional sensor data; and including the additional data record in the database.

In some implementations, the database can be stored on a storage device of the mobile device.

In some implementations, the method can include generating, by the mobile device, one or more clusters of the plurality of data records based on similarities between the plurality of data records. The one or more clusters can be generated using k-means clustering.

In some implementations, the one or more first sensors and the one or more second sensors can include at least one of an accelerometer or an orientation sensor. For each data record, the sensor data can include one or more first signals indicating an acceleration measured by the accelerometer during the impact associated with the data record, and one or more second signals indicating an orientation measured by the orientation sensor during the impact associated with the data record.

In some implementations, the additional sensor data can include one or more additional first signals indicating an acceleration measured by the accelerometer during the period of time, and one or more additional second signals indicating an orientation measured by the orientation sensor during the period of time. Each data record can include metadata regarding the impact associated with the data record. The metadata can include at least one of: an indication of a respective time of the impact associated with the data record, or an indication of a respective day of the week of the impact associated with the data record.

In some implementations, determining whether the user has fallen can include determining, based on the additional sensor data, that the user has experienced an impact.

In some implementations, determining whether the user has fallen can include, responsive to determining that the user has experienced the impact, determining, based on the additional sensor data, a likelihood that the impact corresponds to the user falling.

In some implementations, determining whether the user has fallen can include determining that the user has fallen based on the determined likelihood, and responsive to determining that the user has fallen, determining a similarity metric indicating a similarity between the additional sensor data and the sensor data of one or more clusters of the plurality of data records.

In some implementations, generating the one or more notifications can include determining that the similarity metric is less than a threshold level, and responsive to determining that the similarity metric is less than the threshold level, generating a first notification to the user to confirm whether the user has fallen.

In some implementations, generating the one or more notifications can include receiving, from the user, an input indicating that the user has fallen; and responsive to receiving the input, transmitting a second notification to a communications device remote from the mobile device. The second notification can include an indication that the user has fallen. The communications device can be an emergency response system.

In some implementations, determining whether the user has fallen during the period of time can include determining, based on the additional sensor data, that the user experienced multiple impacts during the period of time; determining, based on the additional sensor data, that the multiple impacts are similar to one another; and in response to determining that the user experienced multiple impacts during the period of time and determining that the multiple impacts are similar to one another, determining that the user is less likely to have fallen during the period of time.

In some implementations, determining whether the user has fallen during the period of time can include determining, based on the additional sensor data, that the user experienced multiple impacts a periodic sequence during the period of time; and in response to determining that the user experienced multiple impacts in a periodic sequence during the period of time, determining that the user is less likely to have fallen during the period of time.

In some implementations, determining whether the user has fallen during the period of time can include determining, based on the additional sensor data, a smoothness of a movement of the user during the period of time; and determining whether the user has fallen during the period of time based on the smoothness of the movement of the user.

In some implementations, determining whether the user has fallen during the period of time can include determining, based on the additional sensor data, an acceleration of the user during the period of time with respect to a first direction and a second direction orthogonal to the first direction; determining that the acceleration in the first direction is greater than a first threshold value and that the acceleration in the second direction is less than a second threshold value; in response to determining that the acceleration in the first direction is greater than the first threshold value and that the acceleration in the second direction is less than the second threshold value, determining that the user is less likely to have fallen during the period of time. The first direction can be orthogonal to a direction of gravity. The second direction can be parallel to the direction of gravity.

In some implementations, at least some of the one or more first sensors or the one or more second sensors can be disposed on or in the mobile device.

In some implementations, at least some of the one or more first sensors or the one or more second sensors can be remote from the mobile device.

In some implementations, at least some of the one or more first sensors can be the same as at least some of the one or more second sensors.

In another aspect, a method includes receiving, by a mobile device, motion data obtained by one or more sensors, where the one or more sensors are worn by a user; determining, by the mobile device based on the motion data, that the user has fallen at a first time; determining, by the mobile device based on the motion data, whether the user has moved between a second time and a third time subsequent to the first time; and upon determining that the user has not moved between the second time and the third time, initiating a communication to an emergency response service at a fourth time after the third time, the communication comprising an indication that the user has fallen and a location of the user.

Implementations of this aspect can include one or more of the following features.

In some implementations, the one or more sensors can include one or more accelerometers. The motion data can include one or more acceleration signals obtained by the one or more accelerometers. Determining whether the user has moved between the first time and the second time can include determining a change in the one or more acceleration signals between the first time and the second time.

In some implementations, the one or more sensors can include one or more orientation sensors. The motion data can include one or more orientation signals obtained by the one or more orientation sensors. Determining whether the user has moved between the first time and the second time can include determining a change in the one or more orientation signals between the first time and the second time.

In some implementations, determining whether the user has moved between the second time and the third time can include determining whether the user is walking between the second time and the third time.

In some implementations, determining whether the user has moved between the second time and the third time can include determining whether the user stood up between the second time and the third time.

In some implementations, the method can include, upon determining that the user has moved between the second time and the third time, refraining from initiating the communication to the emergency response service.

In some implementations, the method can include, subsequent to initiating the communication to the emergency response service, receiving, by the mobile device from the user, a command to terminate the communication; and responsive to receiving the command to terminate the communication, terminating the communication.

In some implementations, the mobile device can be a wearable mobile device.

In some implementations, at least some of the one or more sensors can be disposed on or in the mobile device.

In some implementations, at least some of the one or more sensors can be remote from the mobile device.

In another aspect, a method includes obtaining, by a mobile device, sample data generated by one or more sensors over a period of time, where the one or more sensors are worn by a user; determining, by the mobile device, that the user has fallen based on the sample data; determining, by the mobile device based on the sample data, a severity of an injury suffered by the user; and generating, by the mobile device, one or more notifications based on the determination that the user has fallen and the determined severity of the injury.

Implementations of this aspect can include one or more of the following features.

In some implementations, the one or more sensors can include at least one of an accelerometer, an orientation sensor, or an altimeter.

In some implementations, the sample data can include motion data indicating a motion of the user over the period of time. Determining that the user has fallen can include determining, based on the motion data, a first impact experienced by the user during the period of time, and determining, based on the motion data, a change in orientation of a portion of the user's body during the period of time.

In some implementations, the portion of the user's body can include the user's wrist.

In some implementations, the motion data can include a first signal indicating an acceleration measured by the accelerometer over the period of time, and a second signal indicating an orientation measured by the orientation sensor over the period of time.

In some implementations, determining the severity of the injury suffered by the user can include determining, based on the first signal and the second signal, a severity of the first impact experienced by the user.

In some implementations, determining the severity of the injury suffered by the user can include determining, based on the first signal and the second signal, that the user experienced multiple impacts including the first impact during the period of time.

In some implementations, determining the severity of the injury suffered by the user can include determining, based on the first signal and the second signal, a first set of characteristics associated with the first impact; determining, based on the first signal and the second signal, a second set of characteristics associated with a second impact experienced by the user during the period of time; and determining a similarity between the first set of characteristics and the second set of characteristics.

In some implementations, the motion data can include a third signal indicating an altitude measured by the altimeter over the period of time. Determining the severity of the injury suffered by the user can include determining, based on the third signal, a distance fallen by the user over the period of time. Determining the severity of the injury suffered by the user can include determining the severity of the injury based on the determined severity of the impact experienced by user and the determined distance fallen by the user.

In some implementations, generating the one or more notifications can include transmitting a first notification to a communications device remote from the mobile device. The first notification can include an indication that the user has fallen and an indication of the determined severity of the injury suffered by the user. The communications device can be an emergency response system.

In some implementations, the mobile device can be a wearable mobile device.

In some implementations, at least some of the one or more sensors can be disposed on or in the mobile device.

Particular implementations provide at least the following advantages. In some cases, the implementations described herein can be used to determine whether a user has fallen, and in response, automatically take an appropriate action. As an example, a mobile device can monitor the movement of a user as he goes about his daily life (e.g., walking, running, sitting, laying down, participating in a sport or athletic activity, and so forth). Based on the user's movements, the mobile device can determine whether a user has fallen, and if so, whether the user may be in need of assistance (e.g., physical assistance in standing and/or recovering from the fall, medical attention to treat injuries sustained in the fall, and so forth). In response, the mobile device can automatically notify others (e.g., a caretaker, a physician, medical responder, or a bystander) of the situation, such that they can provide assistance to the user. Thus, assistance can be rendered to the user more quickly and effectively.

Further, the implementations described herein can be used to determine whether a user has fallen and/or whether the user may be in need of assistance more accurately. Thus, resources can be more effectively used. For instance, the mobile device can determine whether the user has fallen and/or whether the user may be in need of assistance with fewer false positives. Thus, the mobile device is less likely to consume computational and/or network resources to generate and transmit notifications to others when the user does not need assistance. Further, medical and logistical resources can be deployed to assist a user with a greater degree of confidence that they are needed, thereby reducing the likelihood of waste. Accordingly, resources can be consumed more efficiently, and in a manner that increases the effective response capacity of a system.

Other implementations are directed to systems, devices and non-transitory, computer-readable mediums including computer-executable instructions for performing the techniques described herein.

The details of one or more embodiments are set forth in the accompanying drawings and the description below. Other features and advantages will be apparent from the description and drawings, and from the claims.

DESCRIPTION OF DRAWINGS

FIG. 10 is a diagram of an example scatter plot of pose angle data collected from a sample population of users that had fallen.

FIG. 11A shows a plot of example acceleration signals obtained by a mobile device over a sliding sample window.

FIG. 11B shows a plot of example rate of rotation signals with respect to the inertia frame obtained by a mobile device over a sliding sample window.

FIG. 11C shows an axis of rotation signal indicating the instantaneous axis of rotation of a mobile device over the sliding sample window.

FIG. 11D shows a total angular displacement signal corresponding to the total angular displacement of a mobile device over a sliding sample window.

DETAILED DESCRIPTION

Overview

Figure 1:
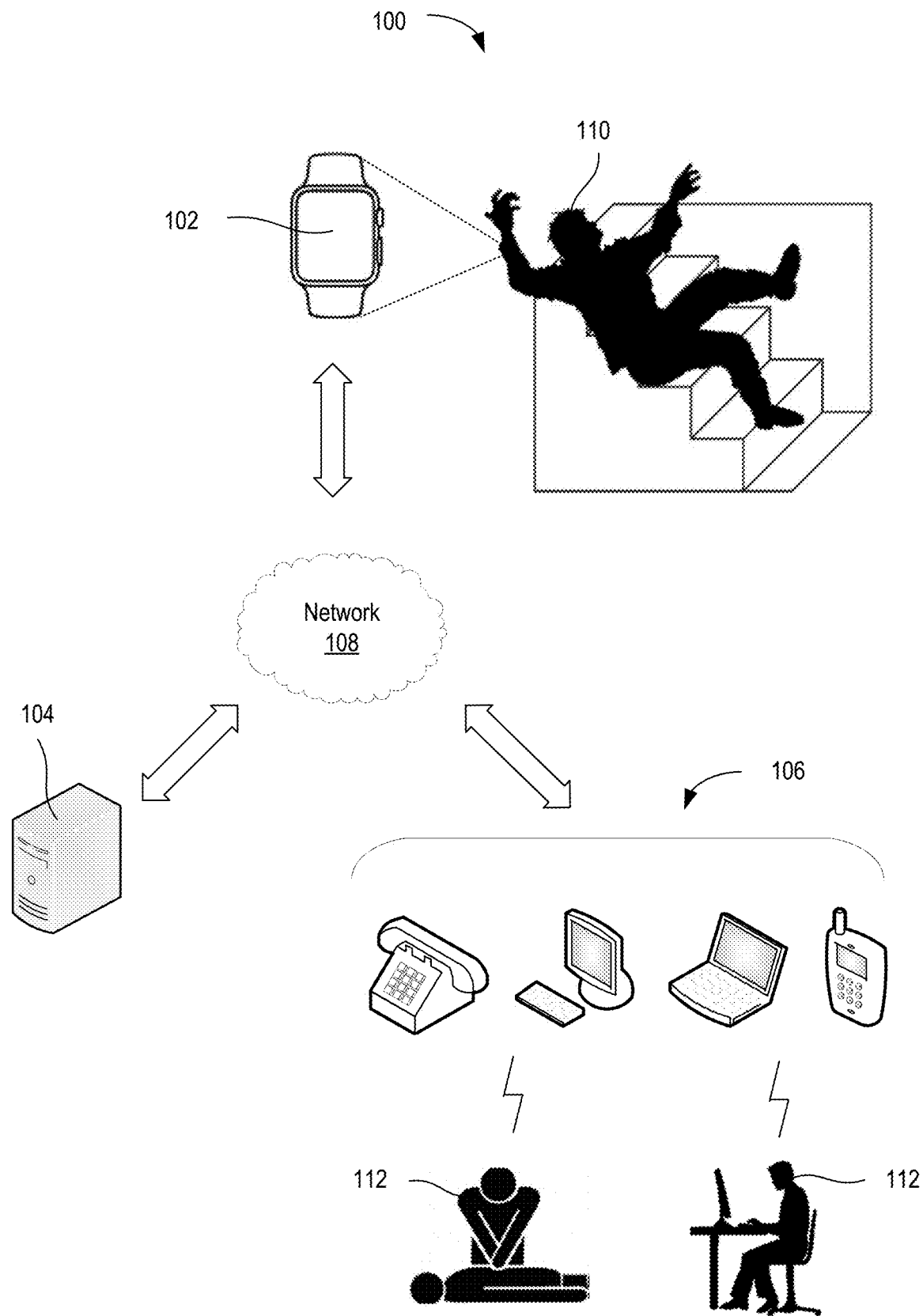
FIG. 1 is a diagram of an example system for determining whether a user has fallen and/or may be in need of assistance.

FIG. 1 shows an example system 100 for determining whether a user has fallen and/or may be in need of assistance. The system 100 includes a mobile device 102, a server computer system 104, communications devices 106, and a network 108.

In an example usage of the system 100, a user 110 positions the mobile device 102 on his body, and goes about his daily life. This can include, for example, walking, running, sitting, laying down, participating in a sport or athletic activity, or any other physical activity. During this time, the mobile device 102 collects sensor data regarding movement of the mobile device 102, an orientation of the mobile device 102, and/or other dynamic properties. Based on this information, the system 100 determines whether the user has fallen, and if so, whether the user may be in need of assistance.

As an example, the user 110 may stumble while walking and fall to the ground. Further, after falling, the user 110 may be unable to stand again on his own and/or have suffered from an injury as a result of the fall. Thus, he may be in need of assistance, such as physical assistance in standing and/or recovering from the fall, medical attention to treat injuries sustained in the fall, or other help. In response, the system 100 can automatically notify others of the situation. For example, the mobile device 102 can generate and transmit a notification to one or more of the communications devices 106 to notify one or more users 112 (e.g., caretakers, physicians, medical responders, emergency contact persons, etc.) of the situation, such that they can take action. As another example, the mobile device 102 can generate and transmit a notification to one or more bystanders in proximity to the user (e.g., by broadcasting a visual and/or auditory alert), such they can take action. As another example, the mobile device 102 can generate and transmit a notification to the server computer system 104 (e.g., to relay the notification to others and/or to store the information for future analysis). Thus, assistance can be rendered to the user 110 more quickly and effectively.

In some cases, the system 100 can determine that the user 110 has experienced an external force, but has not fallen and is not in need of assistance. As an example, the user 110 may have been contacted during an athletic activity (e.g., bumped by another while playing basketball), but has not fallen due to the contact and is able to recover without assistance from others. Accordingly, the system 100 can refrain from generating and transmitting a notification to others.

In some cases, the system 100 can determine that the user 110 has fallen, but that the user is not in need of assistance. As an example, the user 110 may have fallen as a part of an athletic activity (e.g., slipped while skiing), but is able to recover without assistance from others. Accordingly, the system 100 can refrain from generating and transmitting a notification to others.

In some cases, the system 100 can determine that the user 110 has fallen, determine the severity of the injury suffered by the user 110 due to the fall, and perform one or more actions (or refrain from performing one or more actions) in response. As an example, the system 100 can determine that a user 110 has fallen, but has suffered no injury or only a minor injury such that he is able to recover without assistance from others. In response, the system 100 can refrain from generating and transmitting a notification to others. As another example, a system 100 can determine that a user 110 has fallen and has suffered a more severe injury such that he may be in need of assistance. In response, the system 100 can generate and transmit a notification to others to assist the user.

In some cases, the system 100 can make these determinations based on motion data obtained before, during, and/or after an impact experienced by the user 110. For example, the mobile device 102 can collect motion data (e.g., an acceleration signal obtained by a motion sensor of the mobile device 102), and the system 100 can use the motion data to identify a point in time at which the user experienced an impact. Upon identifying the impact time, the system 100 can analyze the motion data obtained during the impact, prior to the impact, and/or after the impact to determine whether the user has fallen, and if so, the severity of injury suffered by the user and/or whether the user may be in need of assistance.

In some cases, the system 100 can also make these determinations in a way that eliminates or otherwise reduces the occurrence of false positives (e.g., incorrect determinations that the user has fallen and/or is in need of assistance, when the user has not actually fallen and/or is not actually in need of assistance). In some implementations, these determinations can be made on a user specific basis. For example, these determinations can be made for a particular user based on historical sensor data that had been previously collected regarding that user, historical information regarding that user's previous activities, the personal characteristics of the user (e.g., physical characteristics, age, demographic, etc.), and/or other information specific to the user.

The implementations described herein enable the system 100 to determine whether a user has fallen and/or whether the user may be in need of assistance more accurately, such that resources can be more effectively used. For instance, the system 100 can determine whether the user has fallen and/or whether the user may be in need of assistance with fewer false positives. Thus, the system 100 is less likely to consume computational and/or network resources to generate and transmit notifications to others when the user does not need assistance. Further, medical and logistical resources can be deployed to assist a user with a greater degree of confidence that they are needed, thereby reducing the likelihood of waste. Accordingly, resources can be consumed more efficiently, and in a manner that increases the effective response capacity of one or more systems (e.g., a computer system, a communications system, and/or an emergency response system).

The mobile device 102 can be any portable electronic device for receiving, processing, and/or transmitting data, including but not limited to cellular phones, smart phones, tablet computers, wearable computers (e.g., smart watches), and the like. The mobile device 102 is communicatively connected to server computer system 104 and/or the communications devices 106 using the network 108.

The server computer system 104 is communicatively connected to mobile device 102 and/or the communications devices 106 using the network 108. The server computer system 104 is illustrated as a respective single component. However, in practice, it can be implemented on one or more computing devices (e.g., each computing device including at least one processor such as a microprocessor or microcontroller). A server computer system 104 can be, for instance, a single computing device that is connected to the network 108. In some implementations, the server computer system 104 can include multiple computing devices that are connected to the network 108. In some implementations, the server computer system 104 need not be located locally to the rest of the system 100, and portions of a server computer system 104 can be located in one or more remote physical locations.

A communications device 106 can be any device that is used to transmit and/or receive information transmitted across the network 108. Examples of the communications devices 106 include computers (such as desktop computers, notebook computers, server systems, etc.), mobile devices (such as cellular phones, smartphones, tablets, personal data assistants, notebook computers with networking capability), telephones, faxes, and other devices capable of transmitting and receiving data from the network 108. The communications devices 106 can include devices that operate using one or more operating system (e.g., Microsoft Windows, Apple OS X, Linux, Unix, Android, Apple iOS, etc.) and/or architectures (e.g., x86, PowerPC, ARM, etc.) In some implementations, one or more of the communications devices 106 need not be located locally with respect to the rest of the system 100, and one or more of the communications devices 106 can be located in one or more remote physical locations.

The network 108 can be any communications network through which data can be transferred and shared. For example, the network 108 can be a local area network (LAN) or a wide-area network (WAN), such as the Internet. As another example, the network 108 can be a telephone or cellular communications network. The network 108 can be implemented using various networking interfaces, for instance wireless networking interfaces (such as Wi-Fi, Bluetooth, or infrared) or wired networking interfaces (such as Ethernet or serial connection). The network 108 also can include combinations of more than one network, and can be implemented using one or more networking interfaces.

Figure 2A:
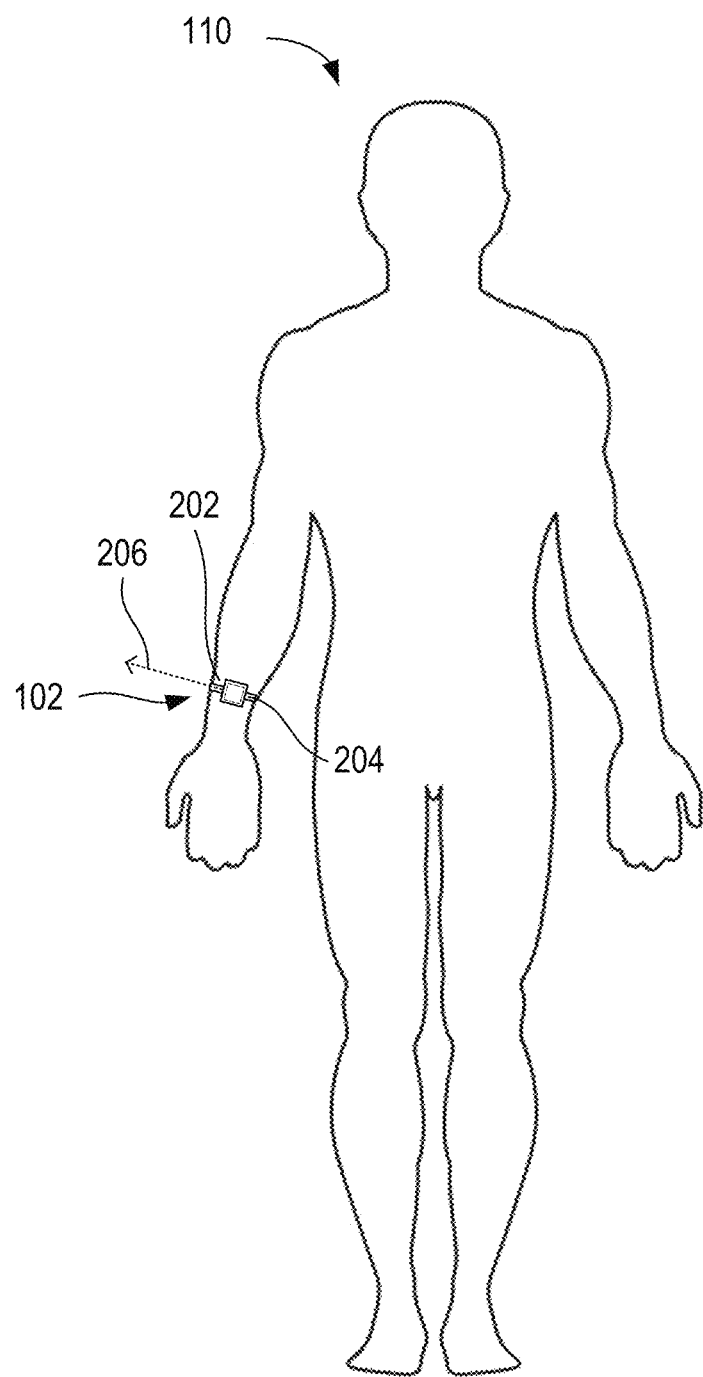
FIG. 2A is a diagram showing an example position of a mobile device on a user's body.

As described above, a user 110 can position the mobile device 102 on his body, and go about his daily life. As an example, as shown in FIG. 2A, the mobile device 102 can be a wearable electronic device or wearable computer (e.g., a smart watch), that is secured to a wrist 202 of the user 110. The mobile device 102 can be secured to the user 110, for example, through a band or strap 204 that encircles the wrist 202. Further, the orientation of the mobile device 102 can differ, depend on the location at which is it placed on the user's body and the user's positioning of his body. As an example, the orientation 206 of the mobile device 102 is shown in FIG. 2A. The orientation 206 can refer, for example, to a vector projecting from a front edge of the mobile device 102 (e.g., the y-axis shown in FIG. 2B).

Although an example mobile device 102 and an example position of the mobile device 102 is shown, it is understood that these are merely illustrative examples. In practice, the mobile device 102 can be any portable electronic device for receiving, processing, and/or transmitting data, including but not limited to cellular phones, smart phones, tablet computers, wearable computers (e.g., smart watches), and the like. As an example, the mobile device 102 can be implemented according to the architecture 2500 shown and described with respect to FIG. 25. Further, in practice, the mobile device 102 can be positioned on other locations of a user's body (e.g., arm, shoulder, leg, hip, head, abdomen, hand, foot, or any other location).

Figure 2B:
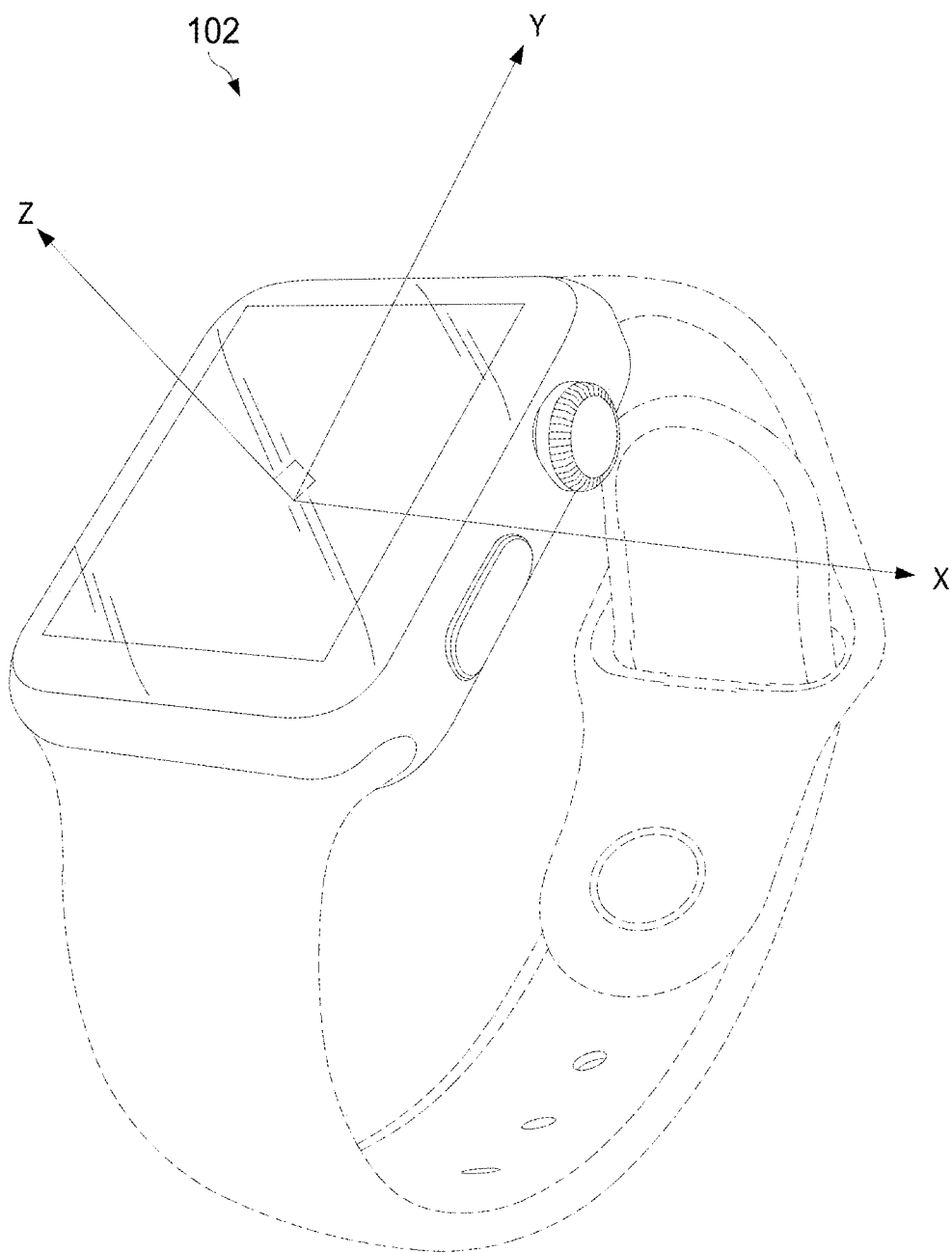
FIG. 2B is a diagram showing example directional axes with respect a mobile device.

As the user 110 goes about his daily life with the mobile device 102 on his body (e.g., walks, runs, sits, lays down, participates in a sport or athletic activity, or any other physical activity), the mobile device 102 collects sensor data regarding the motion of the user 110. For instance, using the motion sensors 2510 shown in FIG. 25 (e.g., one or more accelerometers), the mobile device 102 can measure an acceleration experienced by the motion sensors 2510, and correspondingly, the acceleration experienced by the mobile device 102. Further, using the motion sensors 2510 (e.g., one or more compasses or gyroscopes), the mobile device 102 can measure an orientation of the motion sensors 2510, and correspondingly, an orientation of the mobile device 102. In some cases, the motion sensors 2510 can collect data continuously or periodically over a period of time or in response to a trigger event. In some cases, the motion sensors 2510 can collect motion data with respect to one or more specific directions relative to the orientation of the mobile device 102. For example, the motion sensors 2510 can collect sensor data regarding an acceleration of the mobile device 102 with respect to the x-axis (e.g., a vector projecting from a side edge of the mobile device 102, as shown in FIG. 2B), the y-axis (e.g., a vector projecting from a front edge of the mobile device 102, as shown in FIG. 2B) and/or the z-axis (e.g., a vector projecting from a top surface or screen of the mobile device 102, as shown in FIG. 2B), where the x-axis, y-axis, and z-axis refer to a Cartesian coordinate system in a frame of reference fixed to the mobile device 102 (e.g., a "body" frame).

Figure 3:
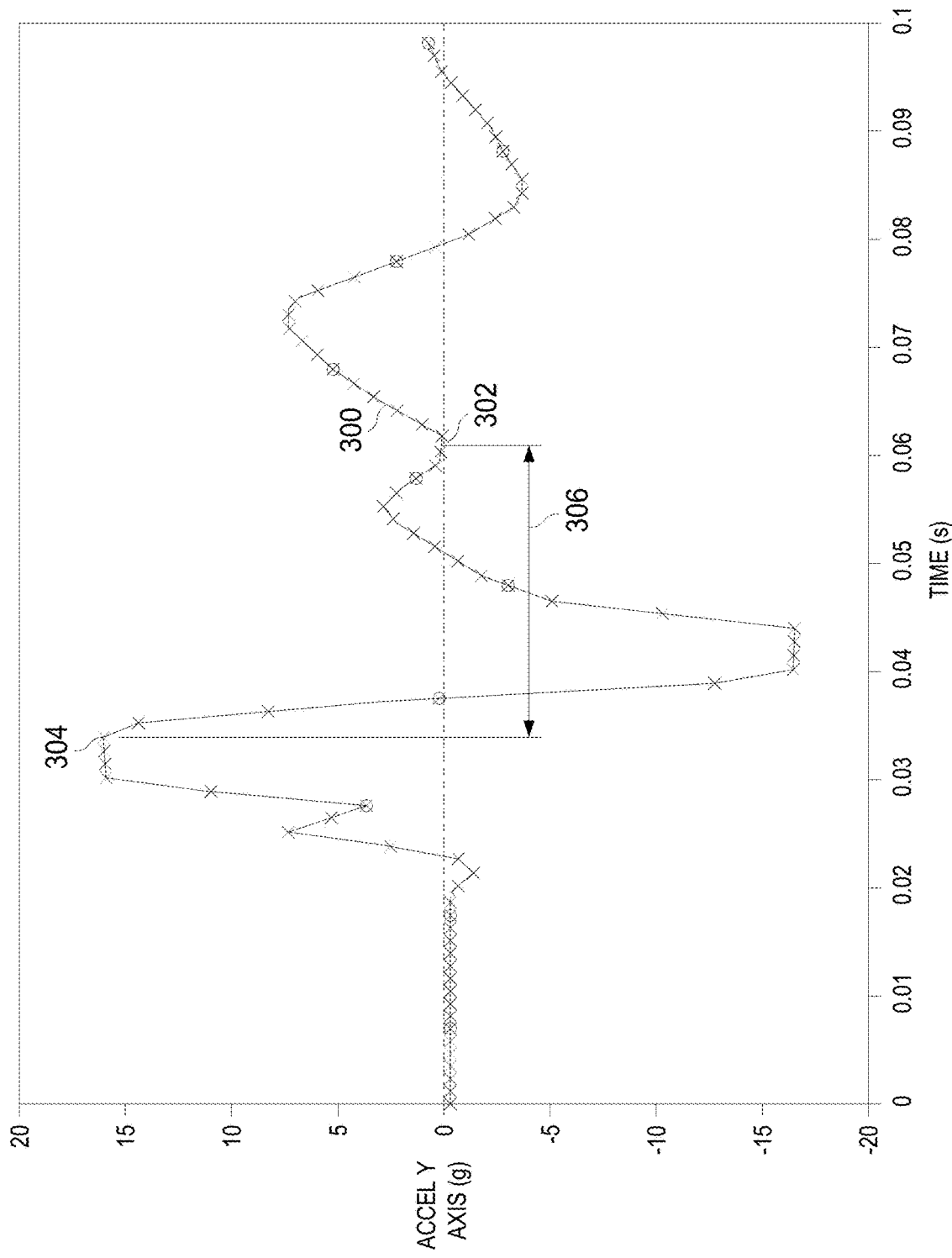
FIG. 3 is a diagram showing an example acceleration signal obtained by a mobile device.

As an example, as shown in FIG. 3, as the user 110 moves, the mobile device 102 can use the motion sensors 2510 to continuously or periodically collect sensor data regarding an acceleration experienced by the motion sensors 2510 with respect to y-axis over a period of time. The resulting sensor data can be presented in the form of a time-varying acceleration signal 300. In some cases, the mobile device 102 can obtain acceleration samples at a sample frequency of 800 Hz using the motion sensors 2510, with a sampling bandwidth of 200 Hz. In practice, other sampling frequencies and/or sampling bandwidths are also possible.

In the example above, the acceleration signal 300 indicates the acceleration experienced by the mobile device 102 with respect to the y-axis of the mobile device. In some cases, the acceleration signal 300 can also indicate the acceleration experienced by the mobile device 102 with respect to multiple different directions. For example, the acceleration signal 300 can include an x-component, a y-component, and a z-component, referring to the acceleration experienced by the mobile device 102 with respect to the x-axis, the y-axis, and the z-axis of the mobile device 102, respectively. Each component also can be referred as a channel of the acceleration signal (e.g., "x-channel," the "y-channel," and the "z-channel").

The mobile device 102 can analyze the acceleration signal 300 to determine whether the user has fallen. For instance, if the user has fallen, the mobile device 102 may experience a relatively strong impact (e.g., when the user's body strikes the ground). Such an impact can be identified based on a magnitude of the acceleration experienced by the mobile device 102 (e.g., the rate of change in the velocity of the mobile device), a magnitude of the jerk experienced by the mobile device (e.g., the rate of change in the acceleration of the mobile device), and an oscillatory behavior of the acceleration experienced by the mobile device 102. Each of these parameters can be determined using the acceleration signal 300.

As an example, the magnitude of the acceleration experienced by the mobile device 102 can be determined, for each channel of the acceleration signal, using the relationship:

$$mag = \max(abs(\alpha(n))),$$

where mag is the magnitude of acceleration for that channel, $\alpha(n)$ is the nth sample of the acceleration signal 300 for that channel, and max is the maximum calculated over a sliding window of samples of the acceleration signal 300, $n_{window}$. In some cases, $n_{window}$ can correspond to the number of samples spanning an interval of time of 0.2 seconds or approximately 0.2 second. For example, if the sampling frequency for the acceleration signal 300 is 800 Hz, $n_{window}$ can be 160. In practice, other values for $n_{window}$ are also possible.

Alternatively, the magnitude of the acceleration experienced by the mobile device 102 can be determined, for each channel of the acceleration signal, using the relationship:

$$mag = \max(\alpha(n)) - \min(\alpha(n)),$$

where mag is the magnitude of acceleration for that channel, $\alpha(n)$ is the nth sample of the acceleration signal 300 for that channel, max is the maximum calculated over a sliding window of samples $n_{window}$, and min is the minimum calculated over the window of samples the acceleration signal 300, $n_{window}$. As above, in some cases, $n_{window}$ can correspond to the number of samples spanning an interval of time of 0.2 seconds or approximately 0.2 second, though in practice, other values for $n_{window}$ are also possible.

If the acceleration signal 300 includes acceleration measurements with respect to a single direction (e.g., having a single channel, such as a y-channel), the magnitude of the acceleration with respect to that direction can be determined using the relationship above. The resulting value is representative of the magnitude of the acceleration for the acceleration signal 300. Alternatively, the total energy from all three channels over the window of interest (e.g. $n_{window}$) may be used as the total magnitude of acceleration. For example, one notion of total energy could be computed as:

$$mag = \text{sqrt}(\max(|x|)^2 + \max(|y|)^2 + \max(|z|)^2).$$

If the acceleration signal 300 includes acceleration measurements with respect to multiple directions (e.g., having multiple channels, such as a x-channel, a y-channel, and a z-channel), the magnitude of the acceleration with respect to each direction can be individually determined using the relationship above, resulting in three individual magnitude values (corresponding to the three channels, respectively). The greatest magnitude value can be selected as representative of the magnitude of the acceleration for the acceleration signal 300.

As another example, the magnitude of the jerk experienced by the mobile device 102 can be determined, for each channel of the acceleration, using the relationship:

$$\text{jerk} = \frac{abs(a(n) - a(n-1))}{\Delta T},$$

where jerk is the magnitude of the jerk for that channel, $\alpha(n)$ is the nth sample of the acceleration signal 300 for that channel, and $\Delta T$ is sampling interval of the acceleration signal 300 (e.g., the inverse of the sampling frequency).

If the acceleration signal 300 includes acceleration measurements with respect to a single direction (e.g., having a single channel, such as a y-channel), the magnitude of the jerk with respect to that direction can be determined using the relationship above. The resulting value is representative of the magnitude of the jerk for the acceleration signal 300.

If the acceleration signal 300 includes acceleration measurements with respect to multiple directions (e.g., having multiple channels, such as a x-channel, a y-channel, and a z-channel), the magnitude of the jerk with respect to each direction can be individually determined using the relationship above, resulting in three individual magnitude values (corresponding to the three channels, respectively). The greatest magnitude value can be selected as representative of the magnitude of the jerk for the acceleration signal 300.

As another example, the oscillatory behavior of the acceleration experienced by the mobile device 102 can be determined by identifying a "third-zero crossing" of the acceleration signal 300. The third-zero crossing refers to the point in time at which the acceleration signal 300 changes from a negative value to a positive value, or vice versa, for the third time for a particular period of oscillation (e.g., "crosses" zero for the third time). As an example, within the window shown in FIG. 3, the third-zero crossing of the acceleration signal 300 occurs at point 302. The time between the maximum value of the acceleration signal 300 (e.g., point 304) and the third-zero crossing point 302 after that maximum value is referred to as the time to the third-zero crossing 306. This value can be used as an estimate for the period of oscillation of the acceleration signal 300, and can be used to estimate the frequency of oscillation of the acceleration signal 300. This can be useful, for example, as the impact response of the components of the motion sensor (e.g., microelectromechanical systems [MEMS] components) can be similar to that of a second-order underdamped system. Thus, the period or frequency of oscillation can be used as an approximation of the response.

The magnitude of the acceleration experienced by the mobile device 102, the magnitude of the jerk experienced by the mobile device 102, and the oscillatory behavior of the acceleration experienced by the mobile device 102 (e.g., the third-zero crossing of the acceleration signal 300) can be used in conjunction to identify impacts that may be indicative of a user falling. In some cases, this determination can be made using a statistical or probabilistic model (e.g., a Bayesian model).

Figure 4:
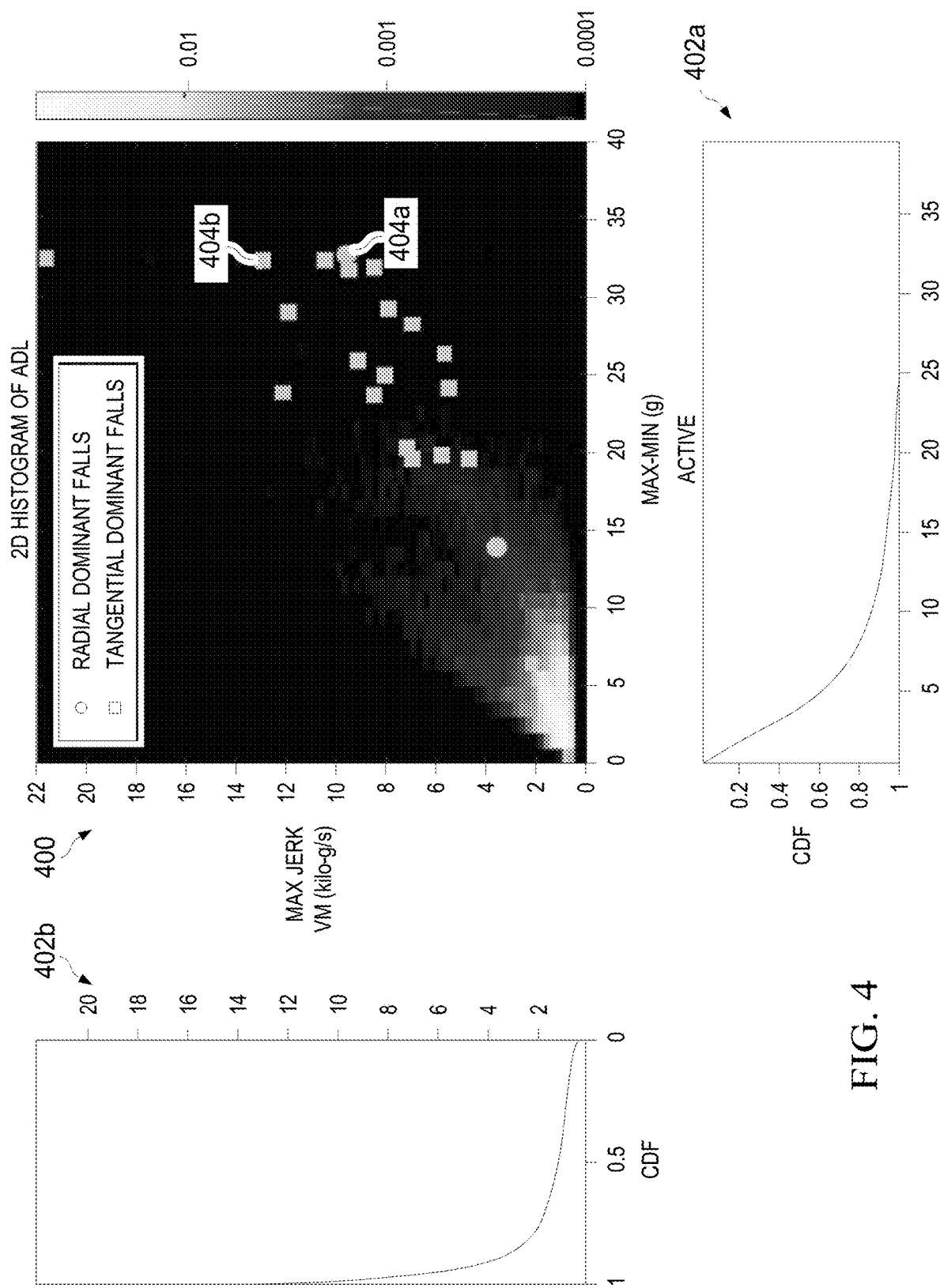
FIG. 4 is a diagram of an example heat map of motion data collected from a sample population of users that did not fall while performing physical activities, and data points indicating motion data collected from a sample population of users that fell.

For example, FIG. 4 shows a heat map 400 of motion data collected from a sample population of users as they performed daily activities (e.g., "active daily life"). This motion data does not include any motion data resulting from a user falling. The heat map 400 compares (i) the magnitude of the acceleration experienced by a mobile device (x-axis), and (ii) the magnitude of jerk experienced by a mobile device (y-axis) for the sample population. Further, the distribution of motion data in the heat map 400 with respect to each axis is shown by a respective cumulative data function 402a or 402b. As shown in FIG. 4, the motion data is primarily concentrated in a region corresponding to a relatively low magnitude of acceleration, combined with a relatively low magnitude of jerk.

FIG. 4 also shows several points 404a and 404b representing motion data collected from a sample population of users that fell. Circular points 404a indicate "radial dominant falls," and square points 404b indicate "tangential dominant falls." These terms refer to the primary movement direction of the mobile device 102 as the user fell (e.g., the motion of a user's arm and wrist as he falls) with respect to the oscillatory movement of the mobile device 102 as a user walks (e.g., the swinging motion of the user's arm and wrist as he walks). As shown in FIG. 4, each of these points 404a and 404b are situated in a region corresponding to a relatively higher magnitude of acceleration, combined with a relatively higher magnitude of jerk. Accordingly, impacts that may be indicative of a user falling can be identified, at least in part, by identifying motion data having a sufficiently high magnitude of acceleration (e.g., greater than a particular threshold acceleration value), combined with a sufficiently high magnitude of jerk (e.g., greater than a particular threshold jerk value). In practice, the threshold acceleration value and/or the threshold jerk value can vary (e.g., based on empirically collected sample data).

Figure 5:
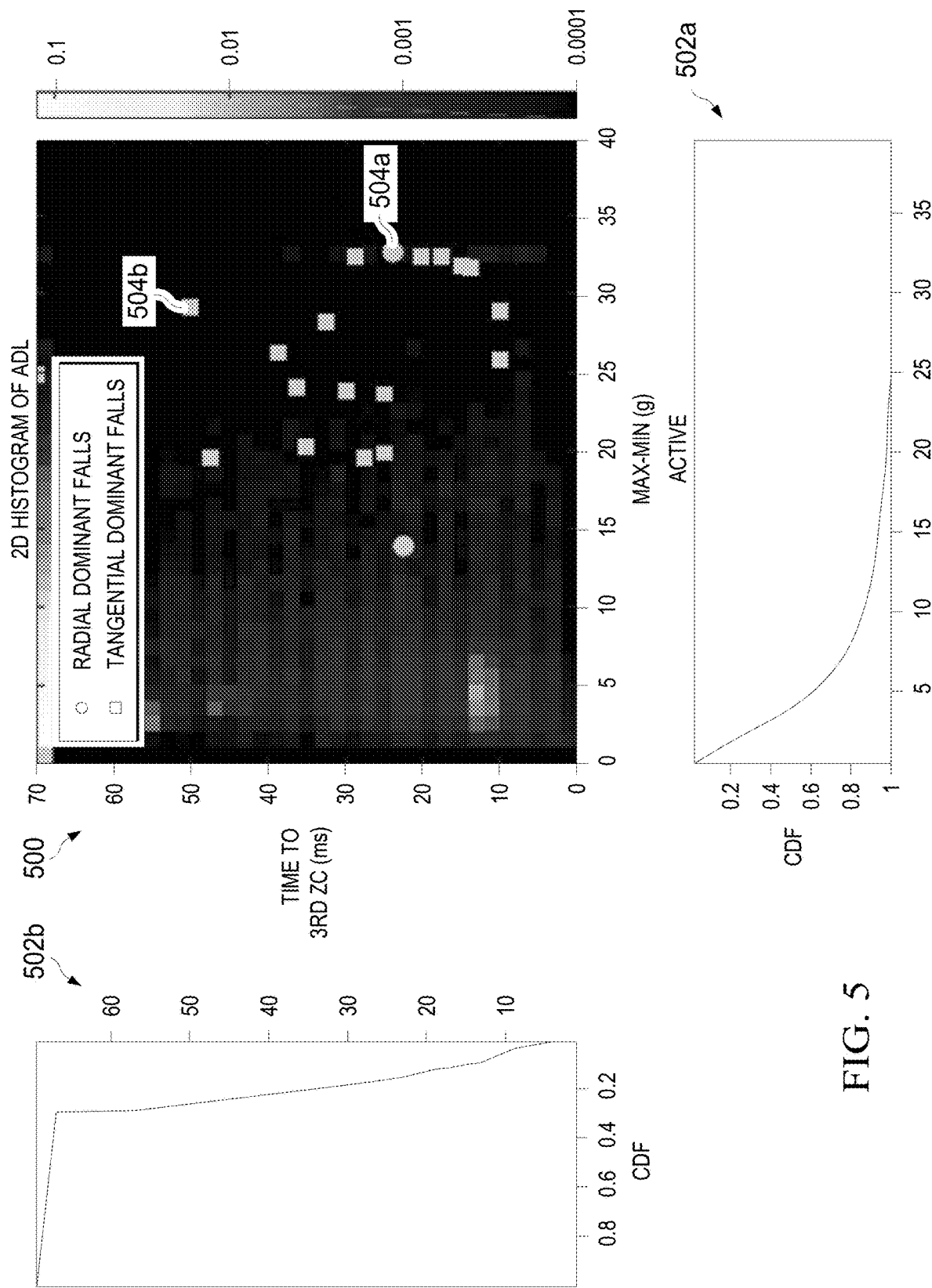
FIG. 5 is a diagram of another example heat map of motion data collected from a sample population of users that did not fall while performing physical activities, and data points indicating motion data collected from a sample population of users that fell.

As another example, FIG. 5 shows a heat map 500 of motion data collected from a sample population of users as they performed daily activities (e.g., "active daily life"). As with the heat map 400 of FIG. 4, this motion data also does not include any motion data resulting from a user falling. The heat map 500 compares (i) the magnitude of the acceleration experienced by a mobile device (x-axis), and (ii) the time to the third-zero crossing of an acceleration signal obtained by a mobile device (y-axis) for the sample population. Further, the distribution of motion data in the heat map 500 with respect to each axis is shown by a respective cumulative data function 502a or 502b. As shown in FIG. 5, the motion data is primarily concentrated in a region corresponding to a relatively low magnitude of acceleration, combined with a relatively high time to the third-zero crossing of an acceleration signal.

FIG. 5 also shows several points 504a and 504b representing motion data collected from a sample population of users that fell. In a similar manner as with FIG. 4, circular points 504a indicate "radial dominant falls," and square points 504b indicate "tangential dominant falls." As shown in FIG. 5, each of these points 504a and 504b are situated in a region corresponding to a relatively higher magnitude of acceleration, combined with a relatively lower time to the third-zero crossing of an acceleration signal. Accordingly, impacts that may be indicative of a user falling can be identified, at least in part, by identifying motion data having a sufficiently high magnitude of acceleration (e.g., greater than a particular threshold acceleration value), combined with a sufficiently low time to the third-zero crossing of an acceleration signal (e.g., less than a particular threshold time value). In practice, the threshold acceleration value and/or the threshold time value can vary (e.g., based on empirically collected sample data).

As described herein, the mobile device 102 can collect motion data, and use the motion data to identify a point in time at which the user experienced an impact. Upon identifying the impact time, the mobile device 102 can analyze motion data obtained during the impact, prior to the impact, and/or after the impact to determine whether the user has fallen, and if so, whether the user may be in need of assistance. In some cases, the mobile device 102 can facilitate this analysis by continuously collecting and buffering motion data. Motion data can include an acceleration signal describing an acceleration experienced by the mobile device 102 (e.g., an acceleration signal 300) and/or an orientation signal describing an orientation of the mobile device 102 (e.g., a signal representing orientation measurements obtained using the motion sensors 2510, such as using a gyroscope or a compass). As an example, the mobile device 102 can retain, on a running basis, portions of an acceleration signal and portions of an orientation signal, each corresponding to a sliding window of time t. Upon identifying an impact (e.g., using the acceleration signal, as described above), the mobile device 102 can retrieve portions of the buffered motion data corresponding to measurements obtained during the impact, prior to the impact, and/or after the impact, and analyze those portions to make a determination regarding the user's condition.

For instance, the mobile device 102 can analyze portions of an acceleration signal and portions of an orientation signal corresponding to measurements obtained prior to an identified impact ("pre-impact" information). Based on the analysis, the mobile device 102 can determine whether the impact likely corresponds to the user falling. In some cases, this determination can be made using a statistical or probabilistic model.

As an example, certain types of activities by a user may be more likely to trigger a fall (e.g., walking, running, navigating stairs, or other such activities). Accordingly, an activity classifier can be used to identify whether a user was performing one of these types of activities prior to the impact. If so, the likelihood that the user has fallen can be higher. Otherwise, the likelihood that the user has fallen can be lower.

An activity classifier can be implemented, for example, by collecting motion data from a sample population (e.g., acceleration signals and/or orientation signals describing motion by each individual of the sample population). Further, information can be collected regarding the physical activities being performed by the sample population (e.g., an indication of the physical activity being performed by each individual at the time that the motion data was measured, such as walking, running, biking, golfing, boxing, skiing, playing basketball, or any other activity). This information can be obtained, for example, from the server computer system 104 (e.g., a server computer system to collect and aggregate data from multiple different mobile devices). Based on this information, particular traits or patterns can be determined for each different type of physical activity. Accordingly, when motion data is collected from an additional user, the motion data can be compared against the previously collected motion data to classify that user's activity.

Further, an activity classifier can be implemented using various techniques. For example, in some cases, an activity classifier can be implemented through the use of "machine learning" techniques such as decision tree learning, association rule learning, artificial neural networks, deep learning, inductive logic programming, support vector machines clustering, Bayesian networks, reinforcement learning, representation learning, similarity and metric learning, sparse dictionary learning, genetic algorithms, rule-based machine learning, learning classifier systems, among others.

As another example, the historical activity level of a user can indicate whether a user is more likely to have fallen and is in need of assistance. For instance, an athletic user who is historically highly active (e.g., historically exhibits frequent and intense movements) may be at a lower risk of falling in a manner that requires assistance. However, a frail user who is historically not active (e.g., historically exhibits infrequent and slight movements) may be at a higher risk of falling in a manner that requires assistance. Accordingly, an activity level classifier can be used to identify the historical activity level of a user, and the likelihood that the user has fallen and is in need of assistance can be adjusted based on the classification.

An activity level classifier can also be implemented, for example, by collecting motion data from a sample population (e.g., acceleration signals and/or orientation signals describing motion by each individual of the sample population). Further, information can be collected regarding the activity levels of the sample population (e.g., an indication of how athletic, physically healthy, and/or ambulatory each individual was at the time that the motion data was measured). This information can be obtained, for example, from the server computer system 104 (e.g., a server computer system to collect and aggregate data from multiple different mobile devices). Based on this information, particular traits or patterns can be determined for each different type of activity level. Accordingly, when motion data is collected from an additional user, the motion data can be compared against the previously collected motion data to classify that user's activity level.

Further, an activity level classifier also can be implemented using various techniques. For example, in some cases, an activity level classifier can be implemented through the use of "machine learning" techniques such as decision tree learning, association rule learning, artificial neural networks, deep learning, inductive logic programming, support vector machines clustering, Bayesian networks, reinforcement learning, representation learning, similarity and metric learning, sparse dictionary learning, genetic algorithms, rule-based machine learning, learning classifier systems, among others.

In some cases, the statistical or probabilistic model can consider additional information regarding the user, such as the user's age, the walking speed of the user, the number of steps that a user takes per day, the number of calories expended by the user per day, a maximum exertion of the user during a day, the gender of the user, the vascular health of the user (e.g., quantified using metrics such as a maximal oxygen uptake, $VO_2$ max, of the user), or other characteristics of the user. The likelihood that a user has fallen can be increased or decreased based on each of these characteristics. For instance, a user who is older may be at a higher risk of falling in a manner that requires assistance, while a user who is younger may be at a lower risk of falling in a manner that requires assistance. Further, a user who has a lower maximum walking speed may be at a higher risk of falling in a manner that requires assistance, while a user who has a higher maximum walking speed may be at a lower risk of falling in a manner that requires assistance. Further, a user has a lower vascular health (e.g., a lower $VO_2$ max) may be at a higher risk of falling in a manner that requires assistance, while a user who has a higher vascular health (e.g., a higher $VO_2$ max) may be at a lower risk of falling in a manner that requires assistance. $VO_2$ max can be measured for example, by measuring the ventilation of the user, and the oxygen and carbon dioxide concentration of the inhaled and exhaled as the user performs a physical activity (e.g., walks on a graded surface, a treadmill, ergometer, etc.). In some implementations, as least some of these measurements can be obtained using air one or more sensors included in and/or communicatively coupled with a mobile device.

As another example, the gender of the user may correspond to a higher or lower risk of falling in a manner that requires assistance.

Further, multiple different characteristics can be used in conjunction to determine the falling risk of a user. As an example, the statistical or probabilistic model can include a multi-dimensional risk assessment model (e.g., a multi-dimensional risk matrix), with each dimension corresponding to a different characteristic of the user and its contribution to the overall risk of the user. Information regarding each user can be collected, from the server computer system 104 (e.g., a server computer system to collect and aggregate data from multiple different mobile devices) and/or user inputs.

In some cases, the mobile device 102 can consider other types of movement made by the user prior to an identified impact. As another example, when a user is falling, a user will often attempt to brace himself from the ground. Accordingly, a mobile device 102 can determine whether a user was performing a bracing motion with his arms prior to an identified impact. If so, the likelihood that the user has fallen can be higher. Otherwise, the likelihood that the user has fallen can be lower.

When performing a bracing motion, a user's hand, and correspondingly the mobile device 102, may accelerate towards the ground for a period of time. Thus, the mobile device 102 may observe a positive acceleration in the inertial z-direction (e.g., the direction perpendicular to ground, or the direction of gravity). By measuring the acceleration in the internal z-direction, the mobile device 102 can determine a duration of the fall. For example, the duration of the fall can be estimated as the period of time in which the acceleration signal along the inertial z-direction is above a particular threshold value.

As another example when the user is falling, he may often flail his arms. For instance, if a user slips, trips, or tumbles while walking, the user may move his arms erratically or chaotically prior to impacting the ground in an attempt to balance himself. Thus, a mobile device 102 can determine whether a user was flailing his arms prior to an identified impact. If so, the likelihood that the user has fallen can be higher. Otherwise, the likelihood that the user has fallen can be lower.

A flailing motion can be detected, in part, by estimating the mobile device's "pose angle," or orientation with respect to the inertial frame (e.g., the earth frame). This can be determined, for example, using both the acceleration signal (e.g., to identify the direction of gravity, or the inertial z-direction) and the orientation signal (e.g., to determine the orientation of the device with respect to the direction of gravity). Using this information, a change in the pose angle of the mobile device 102 over time also can be determined (e.g., the maximum difference in pose angle over a sample window, such as $n_{window}$). A relatively larger change in pose angle over a period of time (e.g., a large change in orientation of the mobile device 102, and correspondingly, the orientation of the user's wrist and arm) can indicate that the user is more likely to be performing a flailing motion.

In some cases, the amount of "chaos" in a user's motions can be determined by obtaining an acceleration signal corresponding to the motions of a user during a period of time, and determining the path length of the acceleration signal. When a user moves erratically (e.g., performs a flailing motion), the acceleration signal will exhibit a higher degree of variation during that period of time. Accordingly, the path length of the acceleration signal will be longer. In contrast, when a user moves less erratically, the acceleration signal will exhibit a lesser degree of variation during that period of time. Accordingly, the path length of the acceleration signal will be shorter.

In some cases, the path length of the acceleration signal can be calculated using the equation:

(path length of acceleration signal)=$\Sigma|\alpha_n-\alpha_{n-1}|$ where $\alpha_n$ is the nth sample in an acceleration signal. The path length can be determined by performing a summation of samples obtained over a sliding window (e.g., a 1.4 second window around a fall or impact). In some cases, chaos can be determined using other techniques (e.g., by measuring the entropy of the acceleration signal).

Figure 6:
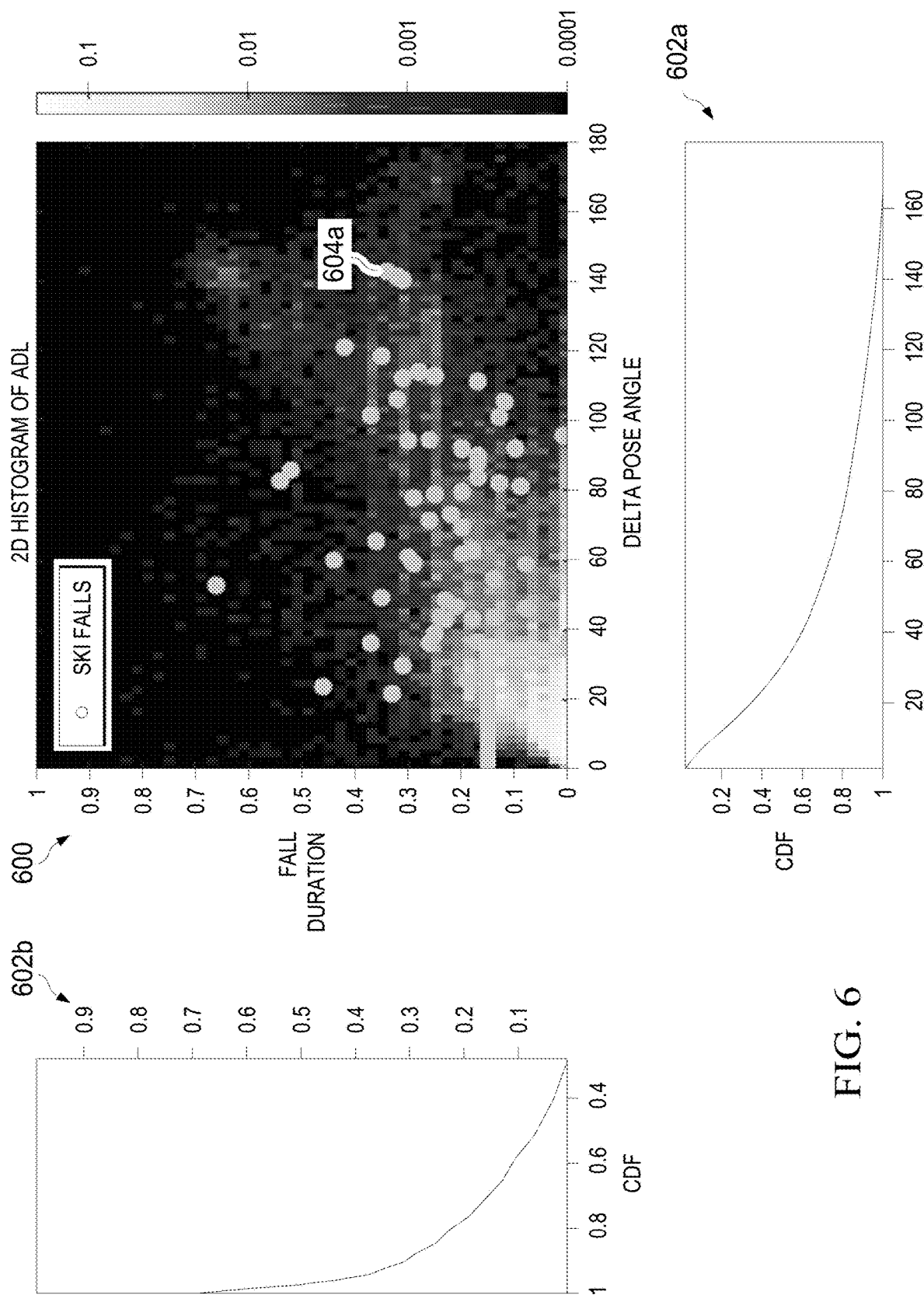
FIG. 6 is a diagram of another example heat map of motion data collected from a sample population of users that did not fall while performing physical activities, and data points indicating motion data collected from a sample population of users that fell.

This "pre-impact" information can be used in conjunction to determine whether the user is likely to have fallen. For example, FIG. 6 shows a heat map 600 of motion data collected from a sample population of users as they performed daily activities (e.g., "active daily life"). This motion data does not include any motion data resulting from a user falling. The heat map 600 compares (i) the change in pose angle of a mobile device (x-axis), and (ii) the fall duration of the mobile device (y-axis) for the sample population. Further, the distribution of motion data in the heat map 600 with respect to each axis is shown by a respective cumulative data function 602a or 602b. As shown in FIG. 6, the motion data is primarily concentrated in a region corresponding to a relatively low change in pose angle, combined with a relatively low fall duration.

FIG. 6 also shows several points 604 representing motion data collected from a sample population of users that fell, where the motion data was collected immediately prior to the users falling. As shown in FIG. 6, each of these points 604 are situated in a region corresponding to a relatively higher change in pose angle, combined with a relatively higher fall duration. Accordingly, a user falling can be identified, at least in part, by identifying motion data—collected immediately prior to an identified impact—having a sufficiently large change in pose angle (e.g., greater than a particular threshold angle), combined with a sufficiently long fall duration (e.g., greater than a particular threshold amount of time). In practice, the threshold angle and/or the threshold amount of time can vary (e.g., based on empirically collected sample data).

The mobile device 102 can also analyze portions of an acceleration signal and portions of an orientation signal corresponding to measurements obtained after an identified impact ("post-impact" information). Based on the analysis, the mobile device 102 can determine whether the user may be in need of assistance. In some cases, this determination can be made using a statistical or probabilistic model.

As an example, if a user falls and is injured or in distress due the fall, the user may exhibit signs of trauma and/or impairment in motion. Signs of trauma and/or impairment in motion can be identified based on the acceleration signal and/or the orientation signal. For instance, the mobile device 102 can analyze portions of an acceleration signal and portions of an orientation signal corresponding to measurements obtained after an identified impact. Based on the analysis, the mobile device 102 can determine whether the impact likely corresponds to signs of trauma and/or impairment in motion.

This analysis can be performed, for example, using an activity classifier. An activity classifier can be implemented, for example, by collecting motion data from a sample population after they have fallen down (e.g., acceleration signals and/or orientation signals describing motion by each individual of the sample population after they fell). Further, information can be collected regarding the condition of each of the individuals after he fell (e.g., an indication that certain individuals exhibited signs of trauma after the fall, an indication that certain individuals exhibited impairment in motion after the fall, and so forth). This information can be obtained, for example, from the server computer system 104 (e.g., a server computer system to collect and aggregate data from multiple different mobile devices). Based on this information, particular traits or patterns can be determined for each different type of condition (e.g., signs of trauma, no signs of trauma, impairment in motion, no impairment in motion, and so forth). Accordingly, when motion data is collected from an additional user, the motion data can be compared against the previously collected motion data to classify that user's condition after he has fallen.

In a similar manner as described above, an activity classifier can be implemented using various techniques (e.g., decision tree learning, association rule learning, artificial neural networks, deep learning, inductive logic programming, support vector machines clustering, Bayesian networks, reinforcement learning, representation learning, similarity and metric learning, sparse dictionary learning, genetic algorithms, rule-based machine learning, learning classifier systems, among others).

The mobile device 102 can also determine a user's condition after he has fallen by identifying one or more motion-based metrics. For example, based on the acceleration signal and/or the orientation signal, the mobile device 102 can determine whether the user has taken any steps after he has fallen (e.g., by identifying trends or patterns in the signals representative of the user taking a step, and/or using a sensor such as a pedometer). If so, the likelihood that the user is in need of assistance is lower. Otherwise, the likelihood that the user is in need of assistance is higher.

As another example, based on the acceleration signal and/or the orientation signal, the mobile device 102 can determine whether the user has stood up after he has fallen (e.g., by identifying trends or patterns in the signals representative of the user rising from the ground and standing). If so, the likelihood that the user is in need of assistance is lower. Otherwise, the likelihood that the user is in need of assistance is higher.

As another example, the mobile device 102 can determine a duration of time during which the standard deviation and the magnitude of the acceleration vector was below a threshold value. If the magnitude of the acceleration vector was below the threshold value for a certain period of time, this may indicate that the user is stationary (e.g., not moving his body). Further, if the user is stationary after he has fallen, this may indicate that the user is dazed or injured. Accordingly, the likelihood that the user is in need of assistance is higher. However, if the standard deviation and the magnitude of the acceleration vector exceeded the threshold value for that period of time, this may indicate that the user is moving his body after he has fallen (e.g., the user is not stationary). Accordingly, the likelihood that the user is in need of assistance is lower.

Figure 7:
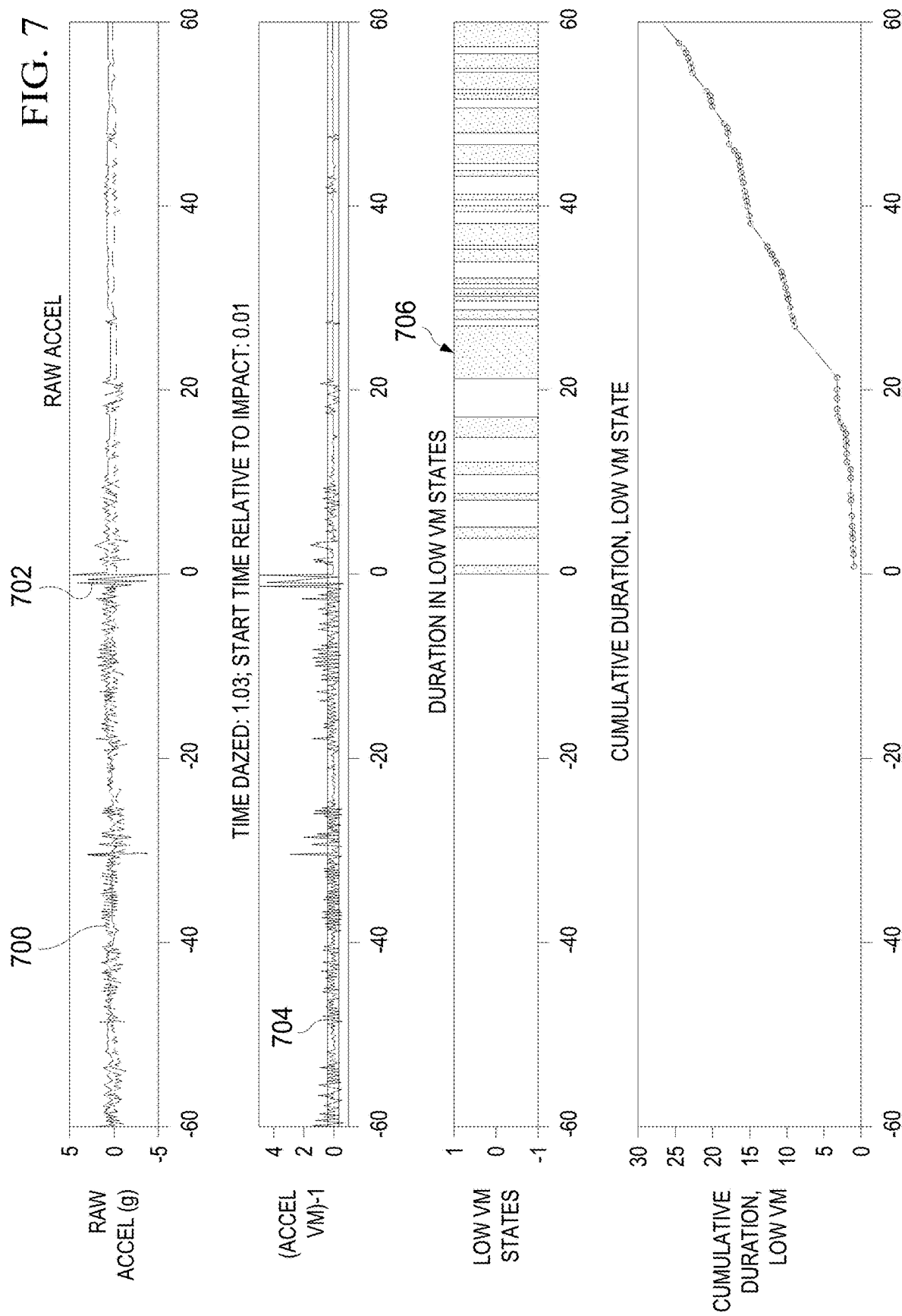
FIG. 7 is a diagram of an example technique for determining a duration of time during which the magnitude of an acceleration vector was below a threshold value.

For instance, as shown in FIG. 7, the mobile device 102 can obtain a "raw" acceleration signal 700 (e.g., in a similar manner as described above with respect to the acceleration signal 300). In the example shown in FIG. 7, the acceleration signal 700 contains three channels, each referring to measured acceleration according to a different direction with respect to the mobile device 102 (e.g., an x-channel, y-channel, and z-channel). Further, the acceleration signal 700 exhibits a sharp increase 702 indicative of an impact.

Further, the mobile device 102 can compute the vector magnitude (VM) of acceleration signal 700 to obtain the vector magnitude signal 704. In practice, when the mobile device 102 is static (e.g., not moving), the vector magnitude signal 704 will be 1 (or approximately 1). When the mobile device 102 is moving, the vector magnitude signal 704 will deviate from 1. Therefore, the relationship |VM−1| can be used as a metric of quiescence. Similarly, the standard deviation of the acceleration signal can also be used as a metric of quiescence.

Further, the mobile device 102 can identify the periods of time 706 after the impact during which the magnitude of the normalized acceleration signal 704 is less than a particular threshold value (indicated by darkened rectangles). In some cases, the threshold value can be 0.025 g. However, in practice, this threshold value can vary, depending on the implementation.

Further, the mobile device 102 can sum each of the periods of time 706 to determine a cumulative duration of time 708 during which the magnitude of the normalized acceleration signal 704 was below a threshold value. If the cumulative duration of time 708 is relatively larger, the likelihood that the user is in need of assistance is higher. However, if the cumulative duration of time 708 is relatively smaller, the likelihood that the user is in need of assistance is lower.

As another example, based on the acceleration signal and/or the orientation signal, the mobile device 102 can determine the pose angle of the mobile device 102. This pose angle can be determined, for example, based on the acceleration signal (e.g., a filtered acceleration signal) and/or the motion orientation of the mobile device 102 (e.g., information derived from a fusion of acceleration data and gyroscopic data). A filtered acceleration signal can be, for example, an acceleration signal having one or more channels (e.g., x-channel, y-channel, and/or z-cannel), with high-frequency content removed (e.g., greater than a particular threshold frequency). In some cases, the removed high-frequency content can correspond to machine-caused motion (e.g., buses, trains, etc.). Based on these sources of information, the mobile device 102 can determine which direction the forearm of the wearer is pointing (e.g., approximately the pose angle of the mobile device 102 in the x-direction).

If the forearm of the wearer is pointing toward the horizon for a longer period of time (e.g., greater than a threshold amount of time), with no motions below or above the horizon, the user may be more likely to be injured. For example, this may indicate that the user is lying on the floor, and is not moving their arm up and down. However, if the user's forearm is moving above and below the horizon repeatedly, with relatively large motions, (e.g., 45°), then this may indicate that a user is less impaired, particular if a determination is made that the user had been ascending or descending stairs.

As another example, based on the acceleration signal and/or the orientation signal, the mobile device 102 can determine the number of times that the acceleration signal (e.g., a filtered acceleration signal) crosses a given threshold value T. This metric can be referred to as the number of threshold-crossings. As above, a filtered acceleration signal can be, for example, an acceleration signal having one or more, with high-frequency content removed. Symmetric crossings require that the acceleration signal went both above T and below (−T) (or vice-versa), whereas asymmetric crossings count the number of times the signal went beyond ±T, regardless of whether it then crossed ∓T.

These threshold-crossings indicate human movement. For example, a user's steps will typically generate symmetric threshold-crossings, while a user reaching for something or rotating the wrist will typically cause asymmetric crossings, and so forth. By counting the number of threshold-crossings, the mobile device 102 can determine whether an individual is likely to be impaired. For example, the greater number of threshold-crossings, the less likely that the user is impaired.

In some cases, this "post-impact" information can be used in conjunction to determine whether the user may be in need of assistance. As an example, the mobile device 102 can make a determination regarding a user's condition after he has fallen based on sample data collected from a sample population. For instance, the mobile device can collect motion data from a sample population (e.g., acceleration signals and/or orientation signals). Further, information can be collected regarding the condition of each of the individuals (e.g., an indication that certain individuals exhibited signs of trauma when the motion data was measured, an indication that certain individuals exhibited impairment in motion when the motion data was measured, and so forth). This information can be obtained, for example, from the server computer system 104 (e.g., a server computer system to collect and aggregate data from multiple different mobile devices).

Using this information, one or more correlations can be determined between the characteristics of a user's movement and the condition of the user. For example, based on the sample data collected from the sample population, a correlation can be determined between one or more particular characteristics of a user's movement corresponding to a user exhibiting signs of trauma. Accordingly, if the mobile device 102 determines that the user's motion exhibits similar characteristics, the mobile device 102 can determine that the user is likewise exhibiting signs of trauma. As another example, based on the sample data collected from the sample population, a correlation can be determined between one or more particular characteristics of a user's movement corresponding to a user exhibiting in impairment in motion. Accordingly, if the mobile device 102 determines that the user's motion exhibits similar characteristics, the mobile device 102 can determine that the user is likewise exhibiting an impairment in motion.

These correlations can be determined using various techniques. For example, in some cases, these correlations can be determined through the use of "machine learning" techniques such as decision tree learning, association rule learning, artificial neural networks, deep learning, inductive logic programming, support vector machines clustering, Bayesian networks, reinforcement learning, representation learning, similarity and metric learning, sparse dictionary learning, genetic algorithms, rule-based machine learning, learning classifier systems, among others.

Figure 8:
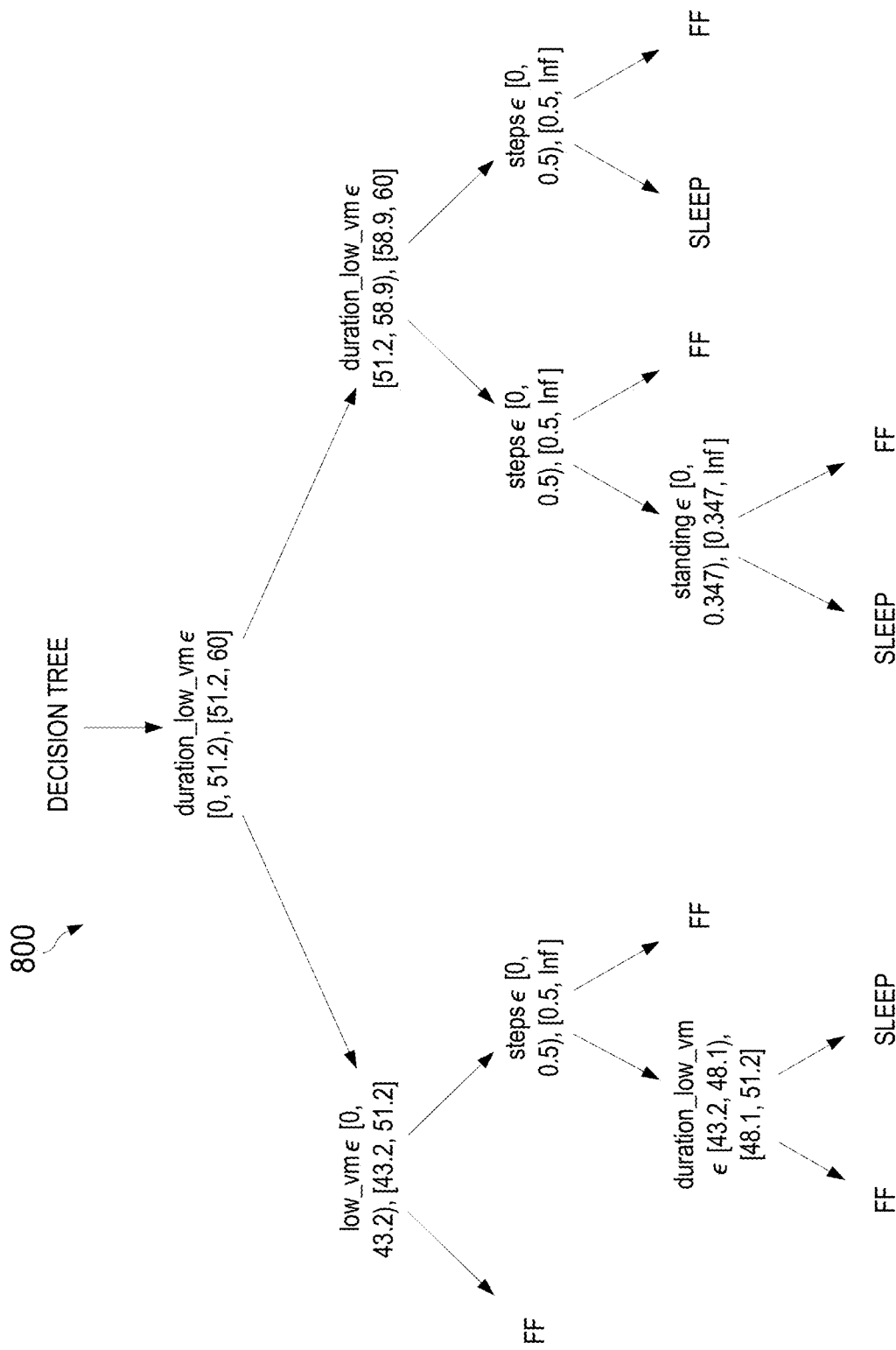
FIG. 8 is a diagram of an example decision tree for determining whether a user is exhibiting signs of trauma and/or impairment in motion.

As an example, FIG. 8 shows a decision tree 800 generated using sample data collected from a sample population (e.g., "trained" using the sample data). In this example, the sample data includes "positive control" information collected from users who were sleeping (e.g., simulating the behavior of individuals who exhibit signs of trauma or impairment in motion). The sample data includes "negative control" information collected from unimpaired users who were performing day to day physical activities.

As shown in FIG. 8, certain combinations of characteristics are indicative of a user exhibiting signs of trauma and/or impairment in motion. For example, if (i) the duration of time during which the magnitude of an acceleration signal was low (parameter "duration_low_vm") is between 48.1 seconds and 51.2 seconds, and (ii) the user took fewer than 0.5 steps (parameter "steps"), a determination can be made that the user is exhibiting signs of trauma and/or impairment in motion.

As another example, if (i) the duration of time during which the magnitude of an acceleration signal was low (parameter "duration_low_vm") is between 51.2 seconds and 58.9 seconds, (ii) the user took fewer than 0.5 steps (parameter "steps"), and (iii) the user was standing for less than 34.7 seconds (parameter "standing"), a determination can be made that the user is exhibiting signs of trauma and/or impairment in motion. In the example shown in FIG. 8, the duration that a user was standing during the post-fall period (parameter "standing") is indicated by an integer between 0 and 600, referring to the duration time in tenths of seconds out of a total sample window of 60 seconds. For instance, if the "standing" value is 347, this indicates that the user was standing for 34.7 seconds post-fall out of the sample window of 60 seconds. In this example, this particular branch indicates that "sleep" (the positive control) was likely if the user was standing between 0 and 34.7 seconds (e.g., the user was standing for less than or equal to approximately half of the post-fall period). In practice, this reflects the expectation that a user would not be standing after a fall.

As another example, if (i) the duration of time during which the magnitude of an acceleration signal was low ("duration_low_vm") is between 51.2 seconds and 58.9 seconds, and (ii) the user took greater than 0.5 steps ("steps"), a determination can be made that the user is not exhibiting signs of trauma and/or impairment in motion. Although example decision branches and parameter values are shown in FIG. 8, these are merely illustrative examples. In practice, the decision branches and/or parameter values of a decision tree can vary, depending on the implementation.

In the example described above, the mobile device 102 determines whether a user may be in need of assistance based on the acceleration signal and the orientation signal. However, the mobile device 102 is not limited to only using these types of information. For instance, in some cases, the mobile device 102 can consider additional information, such as a signal describing a heart rate of the user. As an example, the heart rate of the user is deviates from a particular range (e.g., a "normal" or "healthy" range), the mobile device 102 may determine that the user is more likely to be in need of assistance.

In some cases, "pre-impact" information, impact information, and "post-impact" information can be used in conjunction to determine whether a user has fallen and may be in need of assistance. In some cases, this determination can be made using a decision tree.

Figure 9:
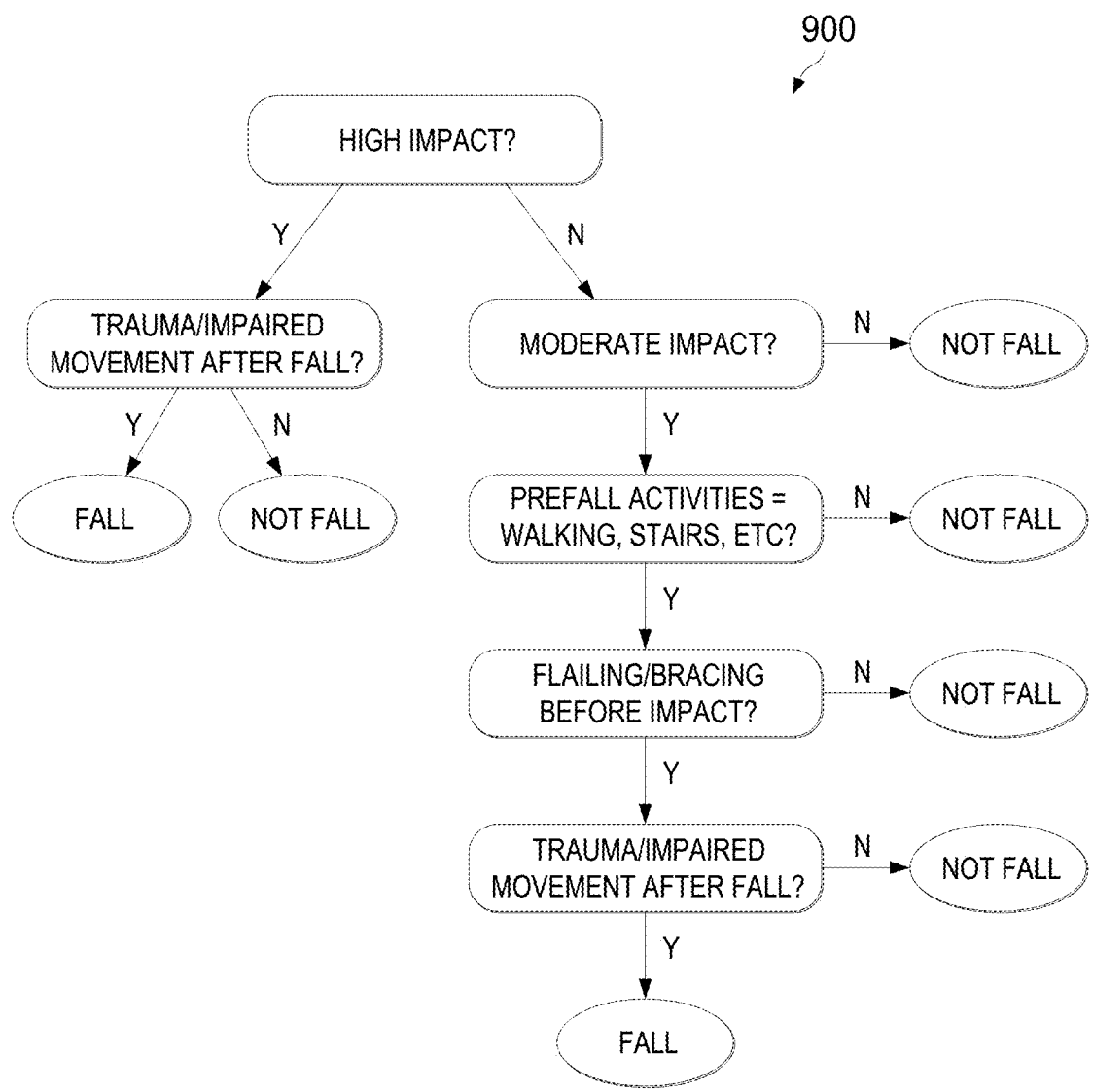
FIG. 9 is a diagram of an example decision tree for determining that either a user has fallen and may be in need of assistance, or a user has either not fallen or has fallen but is not in need of assistance.

As an example, FIG. 9 shows a decision tree 900 for determining that either (i) a user has fallen and may be in need of assistance (indicated as "fall" in decision tree 900), or (ii) a user has either not fallen, or has fallen but is not in need of assistance (indicated as "not fall" in decision tree 900). As shown in FIG. 9, certain combinations of characteristics are indicative of each outcome.

For example, if the user experienced a high impact (e.g., greater than a first threshold value), and exhibited signs of trauma and/or impairment in motion after the impact, a determination can be made that the user has fallen and may be in need of assistance. As another example, if the user experienced a moderate impact (e.g., less than the first threshold value, but greater than a second threshold value smaller than the first threshold value), was performing certain activities prior to the impact (e.g., walking, climbing stairs, etc.), was performing a flailing or a bracing motion prior to impact, and exhibited signs of trauma and/or impairment in motion after the impact, a determination can be made that the user has fallen and may be in need of assistance. Otherwise, a determination can be made that the user has either not fallen, or has fallen but is not in need of assistance. Although example decision branches are shown in FIG. 9, these are merely illustrative examples. In practice, the decision branches of a decision tree can vary, depending on the implementation.

In some cases, a fall detector can be a Bayesian classifier. As an example, the posterior probability of fall can be calculated given a set of features:

$$p(\text{fall}|f1,f2,f3,\ldots) = p(f1|\text{fall})p(f2|\text{fall})p(f3|\text{fall})\ldots$$
$$p(\text{fall})/p(f1,f2,f3,\ldots),$$

where f1, f2, f3, . . . are features computed from acceleration and orientation signals (e.g., an impact magnitude, a jerk, a time to the third zero-crossing, a pre-impact activity, a presence of bracing or flailing, and/or post-impact features determined from a sample population), and p(fall) is the priori probability of a fall, which can be determined based on age, gender and/or other biometric information from the sample population. Analogously, the posterior probability of an impact not being a fall can be computed as:

$$(ADL|f1,f2,f3,\ldots) = p(f1|ADL)p(f2|ADL)\ldots$$
$$p(f3|ADL)p(ADL)/p(f1,f2,f3,\ldots),$$

where ADL represents activities of daily living, which do not contain any instances of the user falling. The mobile device 102 can determine that a fall has occurred when the ratio p(fall|f1, f2, f3, . . . )/p(ADL|f1, f2, f3, . . . ) is greater than a threshold value. In practice, the threshold value can vary, depending on the implementation.

Other types of information can also be used to determine whether a user has fallen. As an example, as discussed above, erratic motions over a period of time may be more indicative of a fall (e.g., the user may be flailing his arms while falling). However, periodic motions over a period of time may be more indicative of intentional movement by the user (e.g., periodic movements of the arms while shaking hands, chopping food, etc.). Accordingly, the periodicity of a user's motion can be used to determine whether a user has fallen.

In some cases, the periodicity of a user's motion can be determined based on a first periodicity metric corresponding to a Fast Fourier Transform (FFT) of the coherent energy of the acceleration signal over a window of time (e.g., 10 seconds) after a detected impact. The coherent energy is the sum of the peaks in the spectrum whose quality is greater than a particular threshold value. A greater first periodicity metric can indicate greater periodicity of movement, which may correspond to a lower likelihood that the user has fallen. A lower first periodicity metric can indicate lesser periodicity of movement, which may correspond to a higher likelihood that the user has fallen.

In some cases, the periodicity of a user's motion can be determined based on a second periodicity metric corresponding to an interquartile range (IQR) of the inter-peak interval of the acceleration signal over a window of time (e.g., 10 seconds) after a detected impact. This can be calculated by identifying all of the peaks around the detected impact that are greater than a particular threshold value, then calculating the IQR of the intervals between adjacent peaks. If the repeating peaks are spaced equally (or substantially equally) apart, the IQR will be small, indicating periodic movement. Accordingly, a lower second periodicity metric can indicate greater periodicity of movement, which may correspond to a lower likelihood that the user has fallen. In contrast, a greater second periodicity metric can indicate lesser periodicity of movement, which may correspond to a higher likelihood that the user has fallen.

In some cases, the mobile device 102 can be used to distinguish between different types of falls. For example, a mobile device 102 can distinguish between a tripping fall (e.g., a fall in which a user stumbles forward, such as when his feet are caught by an obstruction), a slipping fall (e.g., a fall in which a user falls backwards, such as when he loses his balance on a slippery surface), a tumbling fall (e.g., a fall in which a user has rotated or rolled about an axis of rotation, such as when a user rolls down a hill or flight of stairs), and/or other types of falls. This can be useful, for example, as different types of falls may have different effects on a user (e.g., some may be more injurious to a user, while others may be less so). Thus, the mobile device 102 can take a more specific action in response to the particular nature of the user's fall.

As described herein, a mobile device can determine whether a user has fallen based, at least in part, on the mobile device's "pose angle," or orientation with respect to the inertial frame (e.g., the earth frame). In some cases, this can be determined using information obtained by an accelerometer (e.g., by using an acceleration signal generated by the accelerometer to determine to identify the direction of gravity, or the inertial z-direction) and/or information from an orientation sensor, such as a gyroscope (e.g., by using an orientation signal generated by the gyroscope to determine the orientation of the device with respect to the direction of gravity).

In some cases, a mobile device can distinguish between tripping falls and slipping falls based on changes in the pose angle of the mobile device prior to and/or after an impact, and determining whether the measured changes in the pose angle are indicative of a trip or a fall. As an example, when a user trips, he often moves his arm downward to brace for impact. Accordingly, if the mobile device is attached to the user's wrist, it may experience a negative change in pose angle before the impact. Further, at the time of the fall, the pose angle may be pointing towards the ground. As another example, when a user slips, he often throws his arms upward in an attempt to regain his balance. Accordingly, if the mobile device is attached to the user's wrist, it may experience a positive change in pose angle before the impact.

These characteristics can be used to distinguish tripping falls from slipping falls. For example, FIG. 10 shows a scatter plot 1000 of pose angle data collected from a sample population of users that experienced different types of falls using a mobile device attached to each user's wrist. Each point 1002 indicates a particular type of fall (e.g., a tripping fall, a slipping fall, or other types of falls), the corresponding pose angle change (e.g., in degrees) of the mobile device prior to the impact (indicated in the x-axis), and the corresponding pose angle change of the mobile device after the impact (indicated in the y-axis). The sign of the pose angle change can indicate the direction of motion. For example, a positive pose angle change can indicate the final pose angle of the mobile device is higher than the initial pose angle during the time-window of consideration. Likewise, a negative value of pose angle change can indicate that the final pose angle of the mobile device is lower than the initial pose angle. As shown in FIG. 10, when a user experiences a tripping fall, the mobile device moves in the downward direction prior to impact as the user is preparing to brace, and then moves upwards after hitting the surface. Accordingly, trip falls often have a negative pose angle change prior to impact and a positive pose angle change after the impact. In contrast, when a user experiences a slipping fall, the mobile device moves in the upward direction as the user flails his arm before impact, and then moves downwards after impact. Accordingly, slip falls often have a positive pose angle change before impact and a negative pose angle change after the impact. Thus, a mobile device can distinguish between tripping falls and slipping falls based on changes in the pose angle of the mobile device prior to and/or after an impact, and determining whether the measured changes in the pose angle are indicative of a trip or a fall. Further, if the magnitude of pose angle change in either direction is not large enough to convincingly suggest a trip or slip-like fall behavior, the fall may be categorized into a hold-all category of "other" falls. For example, this may be likely in case of falls where the user faints due to dehydration, where there may not be a pronounced flailing or bracing motion before impact as the user loses consciousness In some cases, a system can determine whether a user has tumbled (e.g., fallen in such a way that the user has rotated or rolled about an axis of rotation). This can be beneficial, for example, as tumbling falls can be particularly injurious to a user, and can correspond to higher likelihood that a user is in need of assistance. Example tumbling falls include a user falling and rolling down a flight of stairs or a hill, a user falling headlong (e.g., partially or fully somersaulting), a user "logrolling," or another fall involving a certain degree of rolling or rotation.

As an example, as described above, a user 110 can position the mobile device 102 on his body, and go about his daily life (e.g., walk, run, sit, lay down, participate in a sport or athletic activity, or any other physical activity). During this time, the mobile device 102 collects sensor data regarding the motion of the user 110. For instance, using the motion sensors 2510 shown in FIG. 25 (e.g., one or more accelerometers), the mobile device 102 can measure an acceleration experienced by the motion sensors 2510, and correspondingly, the acceleration experienced by the mobile device 102. Further, using the motion sensors 2510 (e.g., one or more compasses or gyroscopes), the mobile device 102 can measure an orientation of the mobile device 102. In some cases, the motion sensors 2510 can collect data continuously or periodically over a period of time or in response to a trigger event. Further, the mobile device 102 can determine the acceleration and/or orientation with respect to a frame of reference fixed to the mobile device 102 (e.g., a body frame) and/or with respect to the inertial frame (e.g., the earth frame).

The mobile device 102 can continuously measure the acceleration and the orientation of the mobile device over a sliding sample window (e.g., to generate a continuous sample buffer). The acceleration signal can be used to identify the direction of gravity (or the inertial z-direction), and the orientation signal can be used to determine the orientation of the mobile device 102 with respect to the direction of gravity. Using this information, the mobile device 102 can determine the pose angle of the mobile device 102 (approximating the orientation of the user 110). Further, using this information, the rate of rotation of the mobile device 102 can be determined with respect to both the body frame and the inertia frame (approximating the rate of rotation of the user 110 with respect to the body frame and the inertia frame).

As examples, plot 1100 in FIG. 11A shows acceleration signals 1102 obtained over a sliding sample window spanning approximately 2.5 seconds to 7.5 seconds, and plot 1104 in FIG. 11B shows a corresponding rate of rotation signals 1106 with respect to the inertia frame over the same sliding sample window. In this example, a user has fallen on a flight of stairs at approximately the 3 second mark, contacted the stairs and/or railings approximately between the 3 second and 6.5 second marks, and began rolling down the stairs at 6.5 second mark. Plot 1100 includes three different acceleration signals 1102, each corresponding to a different direction (e.g., an x-direction, y-direction, and z-direction in a Cartesian coordinate system in a frame of reference fixed to the mobile device 102, or the body frame). Similarly, plot 1104 includes three different rate of rotation signals 1106, each corresponding to a different direction (e.g., an x-direction, y-direction, and z-direction in a Cartesian coordinate system fixed to the inertial frame). Although a sliding sample window having an example length is shown, in practice, a sliding sample window can have any length (e.g., 1 second, 2 seconds, 3 seconds, 4 seconds, or any other length of time). Further, different frames of references can be used other than Cartesian coordinate system. For example, in some cases, a quaternion coordinate system can be used.

Further, using this information, the mobile device 102 can determine one or more instantaneous axes of rotation of the mobile device 102 over the sliding sample window, the average axis of rotation of the mobile device over the sliding sample window, and a degree of uncertainty associated with the average axis of rotation (e.g., a variance value, standard deviation value, or other uncertainty metric). As an example, plot 1108 in FIG. 11C shows an axis of rotation signal 1110 indicating the instantaneous axis of rotation of the mobile device 102 with respect to the inertial frame for any given point in time in the sliding sample window. An angle of 0° indicates that the mobile device 102 is rotating along an axis parallel to the direction of gravity at a particular point in time, while an angle of 90° indicates that the mobile device is rotating along an axis perpendicular to the direction of gravity at a particular point in time. The average axis of rotation of the mobile device over the sliding sample window and the degree of uncertainty associated with the average axis of rotation can be determined using this signal (e.g., by averaging the values of the signal, and determining a variance, standard deviation, or other uncertainty metric based on the values of the signal).

Further, the mobile device 102 can determine whether the mobile device 102 is rotating with respect to a consistent axis of rotation over the sliding sample window. As an example, if the variation or deviation between the one or more instantaneous axes of rotation of the mobile device 102 and the average axis of rotation during the sliding sample window is lower, the mobile device 102 can determine that the mobile device 102 is rotating more consistently about a particular axis of rotation. However, if the variation or deviation between the one or more instantaneous axes of rotation of the mobile device 102 and the average axis of rotation during the sliding sample window is higher, the mobile device 102 can determine that the mobile device 102 is rotating less consistently about a particular axis of rotation. In some cases, the mobile device 102 can determine that it is rotating with respect to a consistent axis of rotation over the sliding sample window if the variation or deviation between the one or more instantaneous axes of rotation of the mobile device 102 and the average axis of rotation during the sliding sample window is lower than a particular threshold value.

If the mobile device 102 determines that mobile device 102 is rotating with respect to a consistent axis of rotation over the sliding sample window, the mobile device 102 can determine an angular displacement of the mobile device 102 with respect to the sliding sample window. This can be performed, for example, by performing an angular integration of the rate of rotation signal with respect to the inertial frame over the sliding sample window. As an example, plot 1112 in FIG. 11D shows a total angular displacement signal 1014 corresponding to the total angular displacement of the mobile device 102 with respect to the inertial frame over the sliding period of time. The total angular displacement signal 1014 can be obtained, for example, by integrating one or more of the rate of rotation signals 1006 shown in FIG. 11B on a sliding basis.

The mobile device 102 can determine whether a user has tumbled based on the total angular displacement, and the instantaneous axis of rotation of the mobile device 102. For example, as shown in FIG. 11C, the instantaneous axis of rotation of mobile device 102 is relatively stable from around the 6.5 second mark onward (corresponding to the time in which the user began rolling down the stairs). Further, the axis of rotation is consistently approximately 90° during this time, indicating that the user was rolling along an axis of rotation approximately perpendicular to the direction of gravity. Further, as shown in FIG. 11D, the mobile device 102 experienced a relatively large angular displacement at around the same time period. The combination of these characteristics can be indicative of a tumbling fall.

In some cases, the mobile device 102 can determine that a user has tumbled if the one or more instantaneous axes of rotation are greater than a threshold angular value and/or and if the angular displacement is greater than a threshold displacement value. In some cases, the mobile device 102 can determine that a user has tumbled if the one or more instantaneous axes of rotation are relatively large (e.g., greater than threshold angular value) and/or consistent over a threshold period of time (e.g., approximately 90° over a period of 1 second, 2 seconds, 3 seconds, or some period of time).

In some cases, the mobile device 102 can also identify different types of tumbling falls. For example, if the one or more instantaneous axes of rotation are approximately 90° with respect to the direction of gravity, this can signify a tumble in which a user rolls headlong or sideways (e.g., somersaults or logrolls). As another example, if the one or more instantaneous axes of rotation is between 0° and 90° with respect to the direction of gravity, this can signify a tumble in which a user twists while falling.

In a similar manner as described above, upon identifying that a user has tumbled and may be in need of assistance, the mobile device 102 can automatically take an appropriate action in response. For instance, the mobile device 102 can automatically notify the user or others (e.g., an emergency response system, an emergency contact, or others) regarding the situation. Similarly, in some cases, upon determining that the user has tumble and may be in need of assistance, the mobile device 102 can first notify the user before transmitting messages to others (e.g., before transmitting a notification to the emergency response system, the emergency contact, or others).

The implementations described herein are not limited solely to detecting tumbling falls by a user. In some cases, one or more implementations can be used to determine intentional tumbles or rotations by a user. As an example, a device can use rotational data to determine whether a user has somersaulted or logrolled (e.g., as a part of an athletic activity, such as gymnastics). As another example, a device can use rotational data to determine whether a user has performed a tumble turn during swimming (e.g., to count the number of laps that the user has performed in a swimming pool). In practice, other applications are also possible, depending on the implementation.

Upon identifying that a user has fallen and may be in need of assistance, the mobile device 102 can automatically take an appropriate action in response. For instance, the mobile device 102 can determine that the user has fallen and may be in need of assistance, and in response, automatically notify the user or others regarding the situation. As an example, the mobile device 102 can display a notification to the user to inform the user that he has fallen and may be in need of assistance. Further, the mobile device 102 can transmit a notification to a remote device (e.g., one or more of the server computer system 104 and/or communication devices 106) to inform others of the user's condition. This can include, for example, notifications to an emergency response system, a computer system associated with medical personnel, a computer system associated with a caretaker of the user, a bystander, etc. Notifications can include, for example, auditory information (e.g., sounds), textual information, graphical information (e.g., images, colors, patterns, etc.), and/or tactile information (e.g., vibrations). In some cases, notification can be transmitted in the form of an e-mail, instant chat message, text message (e.g., short message service [SMS] message), telephone message, fax message, radio message, audio message, video message, haptic message (e.g., one or more bumps or vibrations), or another message for conveying information.

In some cases, the mobile device 102 can transmit a message to another system using pre-determined contact information. For example, the user of the mobile device 102 can provide contact information regarding an emergency contact, such a telephone number, an e-mail address, a user name in an instant chat service, or some other contact information. The mobile device 102 can generate a message having a compatible data format (e.g., an audio telephone message, a video telephone message, a text message, an e-mail message, chat message, or some other message), and transmit the message to emergency contact using the provided contact information (e.g., using one or more of the server computer system 104 and/or the communication devices 106).

In some cases, upon determining that the user has fallen and may be in need of assistance, the mobile device 102 can first notify the user before transmitting messages to others (e.g., before transmitting a notification to an emergency response system, an emergency contact, or others). In response, the user can instruct the mobile device 102 not to notify others (e.g., if the user is not in need of assistance). Alternatively, the user can expressly instruct the mobile device 102 to notify others (e.g., if the user is in need of assistance). In some cases, if the user does not respond to the notification, the mobile device 102 can automatically notify others (e.g., in the event that the user is incapacitated and unable to respond). In some cases, the mobile device 102 can notify the user multiple different times, and if no response is received from the user after a period of time (e.g., 25 seconds, or some other period of time), automatically notify others for assistance.

In some cases, the mobile device 102 can determine whether to generate and transmit a notification to others using a state machine. A state machine can specify that the mobile device send a fall alert if it observes a short period of quiescence, a behavior that often occurs after a fall. Then, the mobile device detects incapacity by checking for a period of "long lie" by the user (e.g., a period of time in which the user does not move or arise). If incapacity is detected, the mobile device can automatically transmit a distress call to a third party and/or instruct another device to transmit the distress call). The user can also cancel the distress call (e.g., if the user believes that he does not require assistance).

Figure 12:
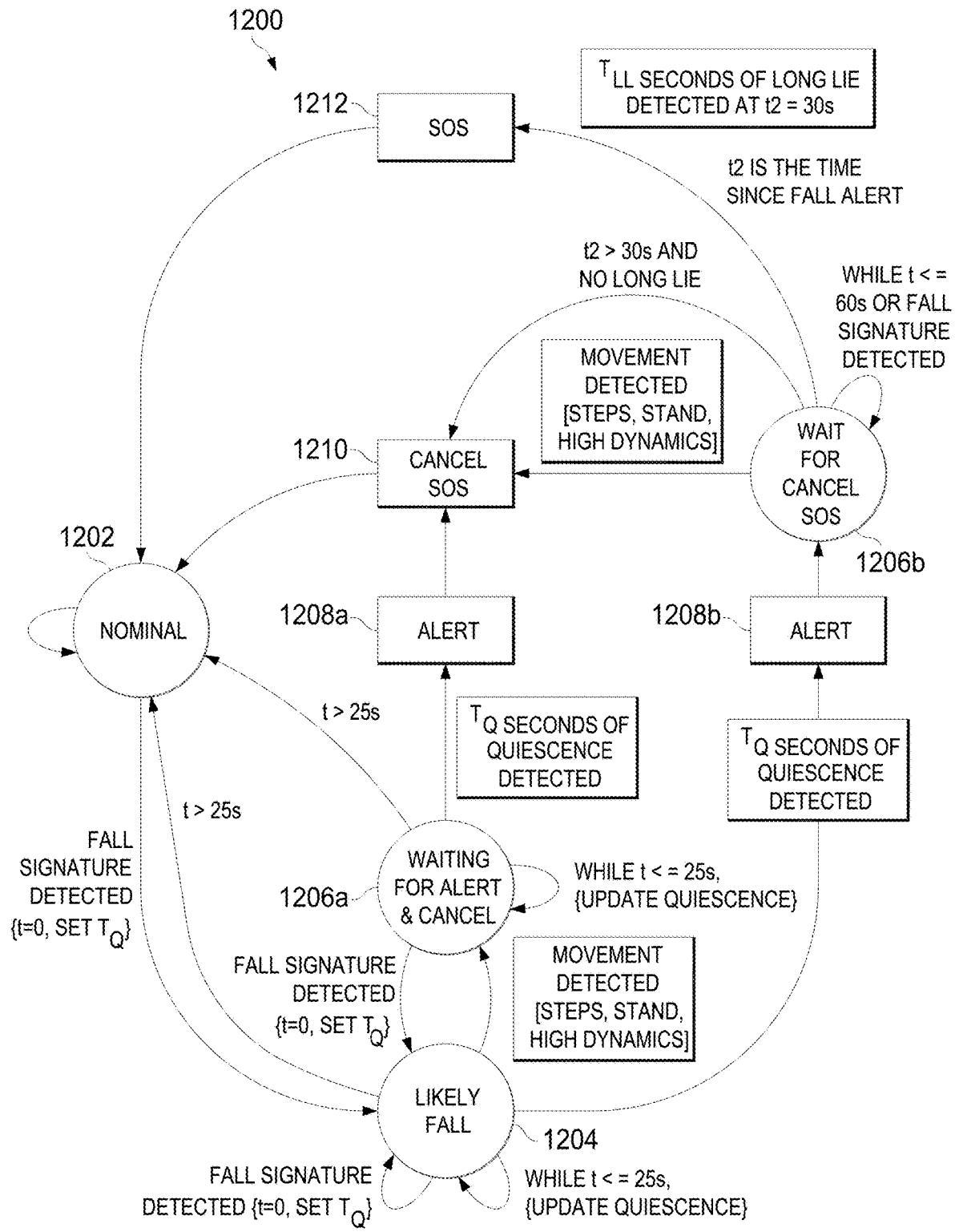
FIG. 12 is a diagram of an example state machine for determining whether to transmit a distress call using a mobile device.

An example state machine 1200 is shown in FIG. 12. In this example, the mobile device begins in a "nominal" state 1202 (e.g., a low alert state of the mobile device), a "likely fall" state 1204 (e.g., an elevated alert state of the mobile device upon detection of a possible fall by the user), "wait" states 1206a and 1206b (e.g., states in which the mobile device waits for additional information, such as a potential input by a user or movement by the user), "alert" states 1208a and 1208b (e.g., states in which the mobile device alerts the user of the mobile device regarding a possible fall and the possibility of sending a distress call to a third-party), a "cancel" state 1210 (e.g., a state in which an impending distress call is canceled), and an "SOS" state 1212 (e.g., a state in which a distress call is conducted). The mobile device can transition between each of the states based on the detection of certain signatures of a fall (e.g., as described herein), detected periods of quiescence (e.g., a lack of movement by the user), and/or inputs by the user.

As an example, the mobile device begins at the "nominal" state 1202. Upon detection of a fall signature (e.g., a combination of sensor measurements and other information indicative of a fall), the mobile device transitions of the "likely fall" state 1204. Upon detection of a period of quiescence $T_Q$ after the fall, the mobile device transitions to the "alert" state 1208b, and alerts the user of the detected fall and informs the user of the possibility of sending a distress call to a third-party (e.g., an emergency responder). The mobile device transitions to the "wait" state 1206b and awaits possible movements by the user. If no user movement is detected during a "timeout" period of time after the transmission of the fall alert elapses (e.g., 30 seconds) and a continuous period of quiescence (e.g., $T_{LL}=10$ seconds) is detected during this time, the mobile device transitions to the "SOS" state 1212 and transmits the distress call. The mobile device then returns to the "nominal" state 1202. This can be useful, for example, if the user has fallen and becomes incapacitated for a lengthy period of time. The mobile device can automatically summon help for the user, even without the user's input.

As another example, the mobile device begins at the "nominal" state 1202. Upon detection of a fall signature, the mobile device transitions of the "likely fall" state 1204. Upon detection of a period of quiescence $T_Q$ after the fall, the mobile device transitions to the "alert" state 1208b, and alerts the user of the detected fall and informs the user of the possibility of sending a distress call to a third-party. The mobile device transitions to the "wait" state 1206b and awaits possible movements by the user. If user movement is detected before a "timeout" period of time after the transmission of the fall alert elapses (e.g., 30 seconds), the mobile device transitions to the "cancel" state 1210, and cancels the distress call. The mobile device then returns to the "nominal" state 1202. This can be useful, for example, if the user has fallen, but affirmatively indicates that he does not require assistance. The mobile device refrain from automatically summon help for the user under this circumstance.

As another example, the mobile device begins at the "nominal" state 1202. Upon detection of a fall signature, the mobile device transitions of the "likely fall" state 1204. Upon detection of certain types of movements after the fall (e.g., stepping movements, standing movements, high dynamic movement, or any other movement indicative of recovery by the user), the mobile device transitions to the "waiting" state 1206*a*. Upon detection of a period of quiescence $T_Q$ after the cessation of movement by the user, the mobile device transitions to the "alert" state 1208*a*, and alerts the user of the detected fall. The mobile device transitions to the "cancel" state 1210, and does not transmit a distress call. The mobile device then returns to the "nominal" state 1202. This can be useful, for example, if the user has fallen, but exhibits signs of recovery. The mobile device can alert the user regarding the fall, but does not automatically summon help for the user under this circumstance.

As another example, the mobile device begins at the "nominal" state 1202. Upon detection of a fall signature, the mobile device transitions of the "likely fall" state 1204. Upon detection of certain types of movements after the fall (e.g., stepping movements, standing movements, high dynamic movement, or any other movement indicative of recovery by the user), the mobile device transitions to the "waiting" state 1206*a*. Upon the passage of 25 seconds without the detection of a period of quiescence $T_Q$, the mobile device returns to the "nominal" state 1202. The mobile device then returns to the "nominal" state 1202. This can be useful, for example, if the user has fallen, but exhibits signs of recovery and continues moving for a lengthy period of time after the fall. The mobile device can refrain from alerting the user or automatically summoning help for the user under this circumstance.

Although time values are shown in FIG. 12, there are merely illustrative examples. In practice, one or more of the time values can differ, depending on the implementation. In some cases, one or more of the time values can be tunable parameters (e.g., parameters that are selected empirically to distinguish between different types or events or conditions).

In some cases, the response sensitivity of the mobile device 102 can vary depending on the characteristics of the user. For instance, the mobile device 102 can determine a probability that the user has fallen and may be in need of assistance. If the probability is greater than a threshold level, the mobile device can automatically notify the user and/or others of the user's fall. The threshold level can vary based on each particular user. For example, if the user is at a higher risk of falling, the threshold level can be lower (e.g., such that the mobile device 102 is more likely to notify the user and/or others about a fall). However, if the user is at a lower risk of falling, the threshold level can be higher (e.g., such that the mobile device 102 is less likely to notify the user and/or others about a fall). The threshold level for each user can be varied based on one or more behavior and/or demographic characteristics of the user, such as the user's age, activity level, walking speed (e.g., maximum observed walking speed over a period of time), or other factors.

Figure 13:
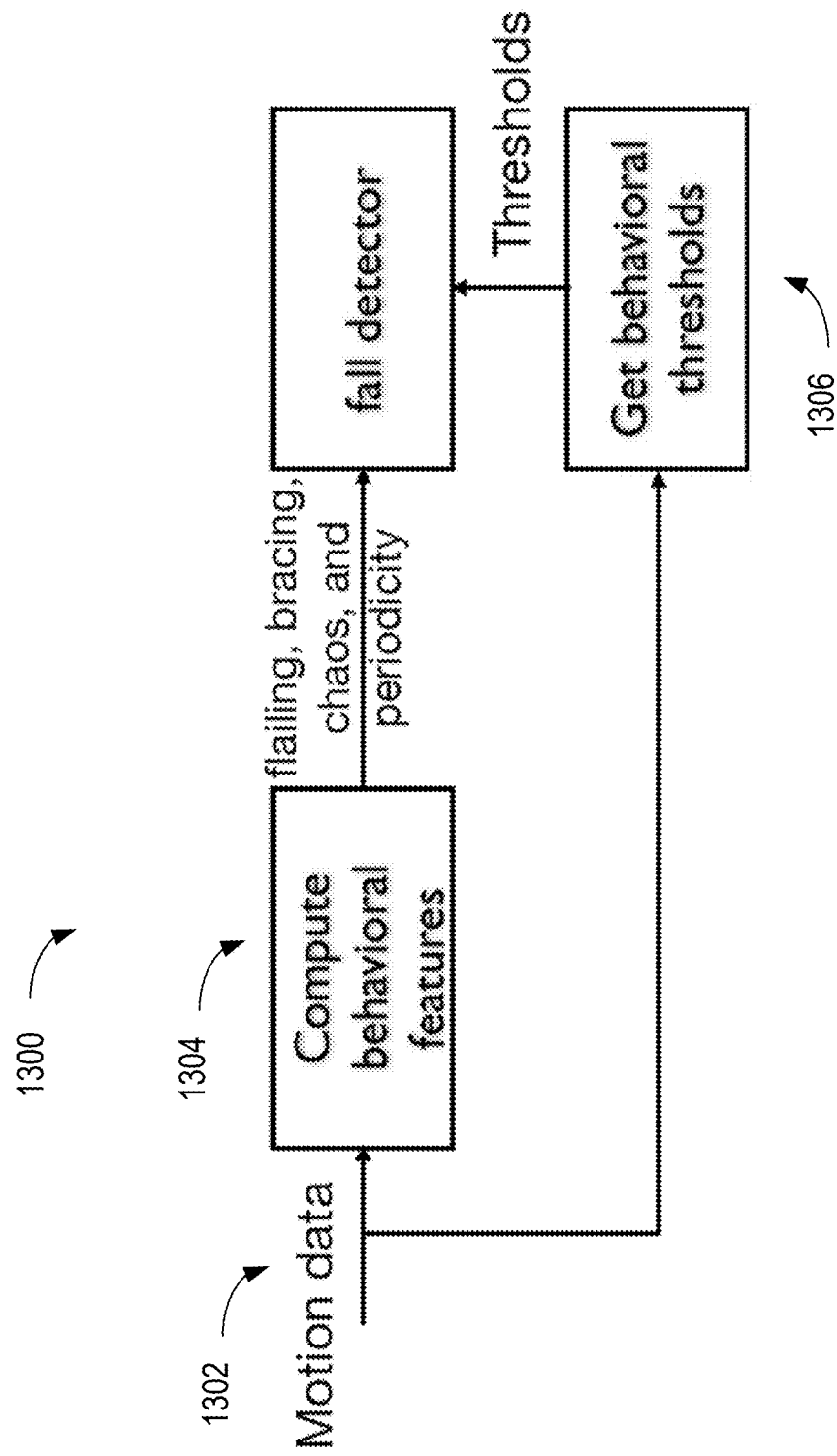
FIG. 13 is a schematic representation of a fall detection technique based on user-specific sensitivity.

As an example, FIG. 13 shows a schematic representation 1300 of a fall detection technique based on user-specific sensitivity. The mobile device receives motion data 1302, and computes behavioral features of the user's motion (e.g., flailing motions, bracing motions, chaotic motions, periodic motions, or other features, as described herein) (1304). Further, the mobile device determines sensitivity thresholds based on the user's behavior and/or demographic characteristics (1306). The mobile device determines whether the user has fallen and/or whether to transmit a distress call based on the determined features and thresholds (e.g., using a fall detector 1308 performing one or more of the techniques described herein).

As described herein, a mobile device can determine whether a user has fallen based, at least in part, on the mobile device's "pose angle," or orientation with respect to the inertial frame. In some cases, this can be determined using information obtained by an accelerometer and/or information from an orientation sensor, such as a gyroscope.

In practice, the dynamic range of the accelerometer can vary, depending on the implementation. For example, the accelerometer can have a dynamic range of 16 g. As another example, the accelerometer can have a dynamic range of 32 g (e.g., to detect a greater range of accelerations).

In some cases, the accelerometer and the gyroscope can each obtain measurements according to the same sample rate (e.g., 200 Hz, 400 Hz, 800 Hz, or some other frequency). In some cases, the accelerometer and gyroscope can each obtain measurements according to different sample rates. As an example, the accelerometer can obtain measurements according to a higher sample rate (e.g., 800 Hz), while the gyroscope can obtain measurements according to a lower sample rate (e.g., 200 Hz). This can be useful, for example, in selectively reducing the power consumption of one sensor (e.g., a sensor that consumes more power during operation) relative to the other to improve the power efficiency of the mobile device. In some cases, the sample rate of the accelerometer and/or gyroscope can be dynamically adjusted during operation. For instance, the sample rate of the accelerometer and/or gyroscope can be selectively increased during certain periods of time and/or in response to certain conditions (e.g., greater user motion), and decreased during certain other periods of time and/or in response to certain other conditions (e.g., lesser user motion).

In some cases, one of the accelerometer or the gyroscope can be used to obtain measurements, while the other sensor is disabled (e.g., such that it does not collect measurements). The disabled sensor can be selectively activated in based on measurements obtained from the active sensor. This can be useful, for example, in reducing the power consumption of the mobile device (e.g., by operating only one of the accelerometer or the gyroscope during certain periods of time, and selectively operating both of the accelerometer or the gyroscope in response to certain conditions).

As an example, the mobile device can disable the gyroscope, and use the accelerometer to obtain acceleration measurements over a period of time. If the measured acceleration is greater than a particular threshold level (e.g., the root mean square [RMS] energy of the accelerometer's acceleration signal is greater than a threshold energy level), the mobile device can activate the gyroscope and collect orientation information. Accordingly, the gyroscope is selectively activated in response to the detection of "significant" motion by the accelerometer.

In some cases, the gyroscope can be disabled if significant motion is no longer detected. For example, if the RMS energy of the accelerometer's acceleration signal is less than the threshold energy level for a particular period of time (e.g., a pre-defined time interval), the mobile device can disable the gyroscope, and continue operating the accelerometer. In some cases, the gyroscope can be disabled a particular period of time after the gyroscope was activated (e.g., after a pre-defined time interval has elapsed since the gyroscope was switched on). In some cases, the gyroscope can be disabled if the RMS energy of the accelerometer's acceleration signal is less than the threshold energy level for a first time interval, or if a second time interval has elapsed since it was activated, whichever occurs first. In practice, the time intervals can vary, depending on the implementation.

Figure 14:
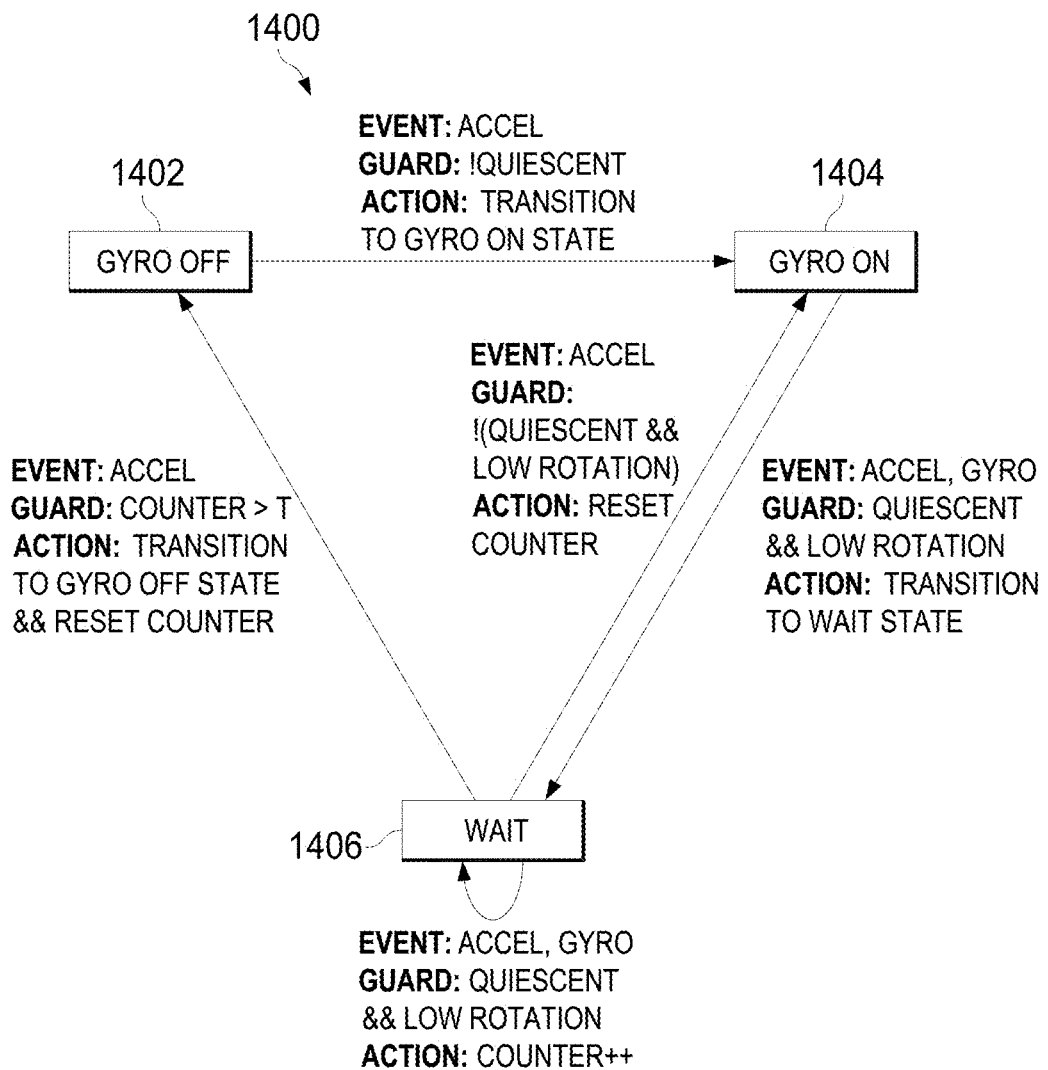
FIG. 14 is a diagram of an example state machine for selectively enabling and disabling a gyroscope.

In some cases, the gyroscope can be selectively enabled and disabled according to a state machine. FIG. 14 shows an example state machine include a "gyro off" state 1402 (corresponding to a disabled state of the gyroscope), a "gyro on" state 1404 (corresponding to an enabled state of the gyroscope), and a "wait" state 1406 (corresponding to a state in which the mobile device waits further information before adjusting the operation of the gyroscope)."

The mobile device begins in the "gyro off" state 1402, in which the gyroscope is disabled. The mobile device transitions of the "gyro on" state 1404 and enables the gyroscope upon detection of a period of non-quiescence based on an acceleration signal obtained from an accelerometer. Upon detection of quiescence and low rotation based on the acceleration signal and an orientation signal from the gyroscope, the mobile device transitions to the "wait" state 1406. If quiescence and low rotation continues, the mobile device periodically increments a counter over time. If the counter exceeds a threshold value, the mobile device returns to the "gyro off" state 1402 and disables the gyroscope, and resets the counter. However, if non-quiescence and/or a sufficiently high degree of rotation is detected, the mobile device instead returns to the "gyro on" state 1404 and keeps the gyroscope enabled, and resets the counter. In this manner, the mobile device selectively enables the gyroscope in response to the detection of movement, and disables it after a period of quiescence and low rotation.

In some cases, the "Quiescence" condition shown in FIG. 14 can be a Boolean value that is true when the following equation is satisfied:

$$thr1 \leq k1*VM + k2*dVM < thr2$$

where VM is the magnitude of the acceleration signal, dVM is the rate of change of the magnitude of the acceleration signal, and thr1 and thr2 are tunable threshold values In some cases, the "Quiescence && Low Rotation" condition shown in FIG. 14 can be a Boolean value that is true when the following equation is satisfied:

$$(thr1+\delta \leq k1*VM + k2*dVM < thr2-\delta) \text{ AND } (rot < thr3)$$

where VM is the magnitude of the acceleration signal, dVM is the rate of change of the magnitude of the acceleration signal, rot is the rotation rate (e.g., as determined based on the gyroscope), δ is a tunable offset value, and thr1, thr2, and thr3 are tunable threshold values.

In some cases, falls can be detected based on a combination or "fusion" of multiple different types of sensor measurements. For instance, falls can be detected based on acceleration measurements (e.g., obtained by an accelerometer), orientation measurements (e.g., obtained by a gyroscope), air pressure measurements (e.g., obtained by a pressure sensor or barometer), altitude measurements (e.g., obtained by an altimeter, pressure sensor, accelerometer, or other sensor), heart rate measurements (e.g., obtained by a heart rate sensor), and/or other types of measurements.

Figure 15:
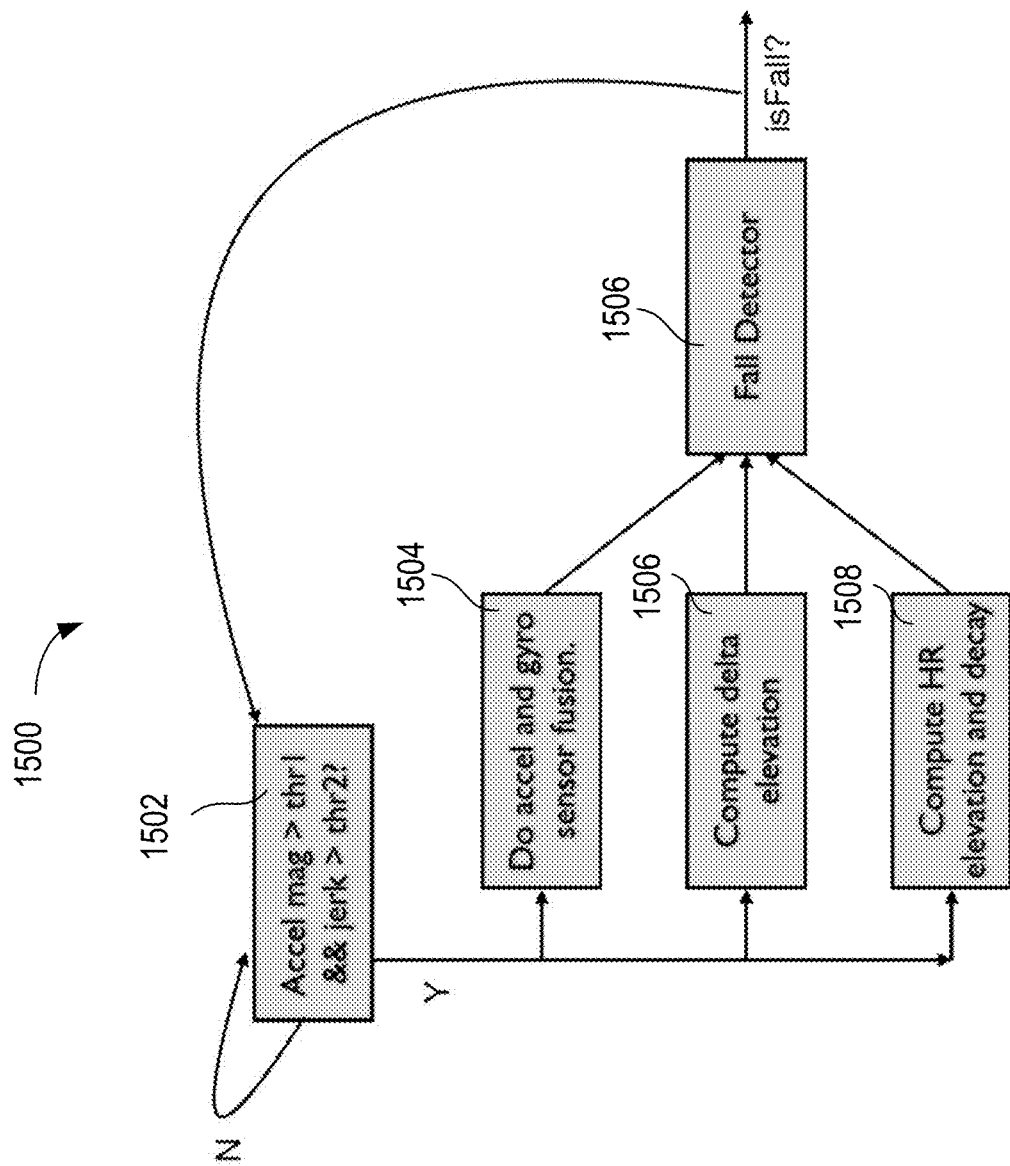
FIG. 15 is a schematic representation of a fall detection technique based on multiple types of sensor measurements.

As an example, FIG. 15 shows a schematic representation 1500 of a fall detection technique based on multiple types of sensor measurements. An accelerometer is used to detect hard impacts (step 1502). Hard impacts can be detected, for example, based on the magnitude of acceleration $\alpha_{mag}$ and the magnitude of jerk $j_{mag}$ measured by the accelerometer over a sliding window. The magnitude of acceleration over the sliding window can be calculated using the following equation:

$$\alpha_{mag} = \text{sqrt}(\max(|x|)^2 + \max(|y|)^2 + \max(|z|)^2)$$

where x, y, and z are the x, y, and z components of the acceleration signal, respectively, and max is taken in a 0.2 second window.

The magnitude of jerk over the sliding window can be calculated using the following equation:

$$j_{mag} = \max(\text{sqrt}(dx^2 + dy^2 + dz^2))$$

where dx, dy, and dz are the derivatives of the x, y, and z components of the acceleration signal, respectively and max is taken in a 0.2 second window.

If $\alpha_{mag}$ is greater than a threshold value thr1 and $j_{mag}$ is greater than a threshold value thr2, the mobile device obtains gyroscopic measurements (stop 1504), elevation or altitude measurements (step 1506), and heartrate information (step 1508), and determines whether a fall has occurred based on the measurements (step 1510).

As an example, accelerometer and gyroscopic measurements can be used to determine an impact direction and the pose angle of the mobile device before, during, and/or after an impact (e.g., as described herein). In some cases, accelerometer measurements can be used to approximate the mobile device's elevation or altitude (e.g., when the mobile device is static). In some cases, accelerometer and gyroscopic measurements can be used in conjunction to approximate the mobile device's elevation or altitude (e.g., when the mobile device is in motion).

As another example, pressure sensors can be used to detect multi-level falls (e.g., a user falling off a ladder). As another example, heart rate sensors can be used to detect changes in heart rate, such as an elevation of heart rate (e.g., due of a fight-or-flight response) or heart rate decay curves (e.g., a person's heart rate decay after a fall may have distinctive characteristics, such as a smaller time constant, compared to the heart rate decay after the end of a physical work out). As another example, accelerometers can be used to detect evaluation or altitude (e.g., when the device is static). As another example, accelerometers can be used to detect evaluation or altitude (e.g., when the device is static).

Figure 16:
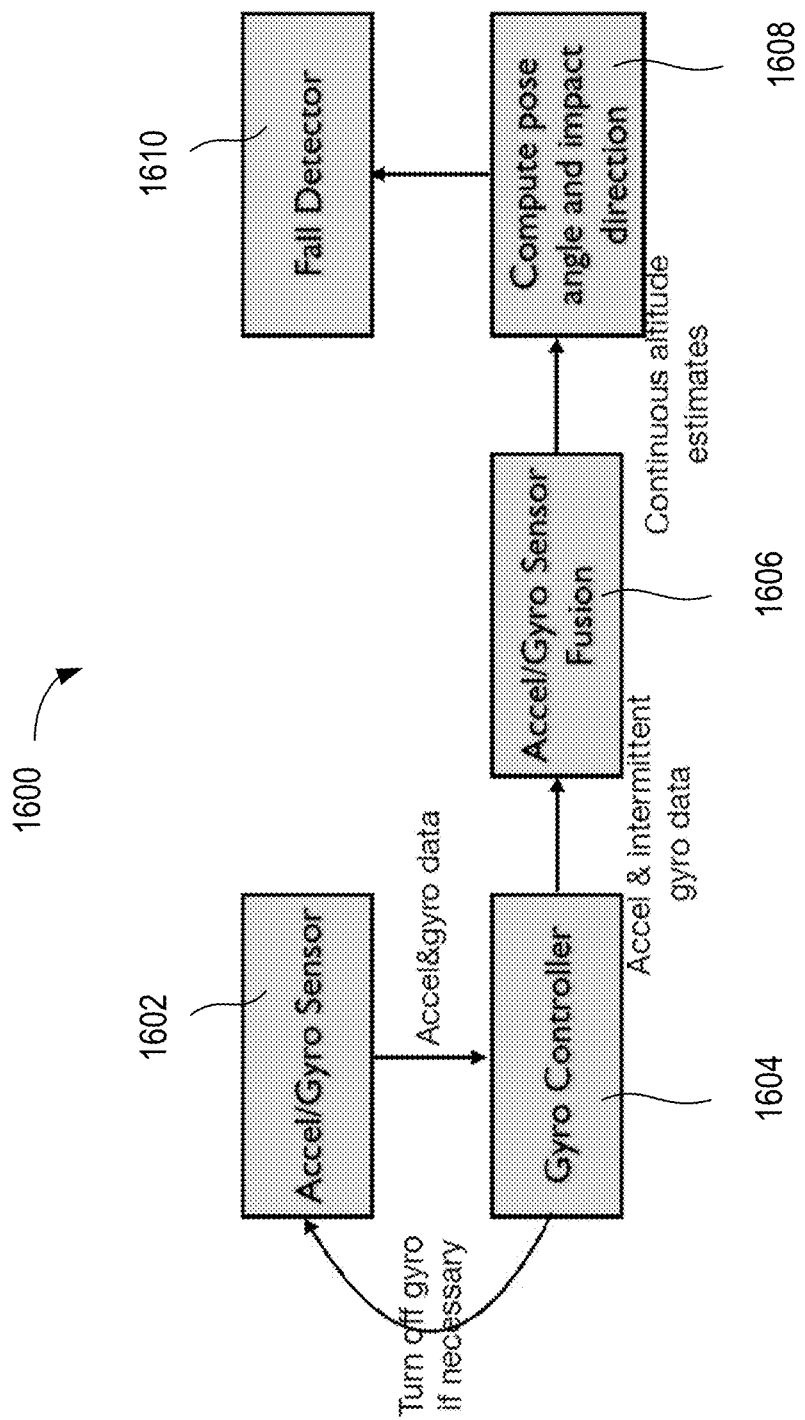
FIG. 16 is a schematic representation of an example usage of an accelerometer and gyroscope in conjunction to determine information regarding the motion of a user

FIG. 16 shows an example use of an accelerometer and gyroscope in conjunction to determine information regarding the motion of a user (e.g., as a part of step 1504 shown in FIG. 15). The accelerometer and the gyroscope generate accelerometer and gyroscopic measurements (step 1602). Based on this information, a gyroscopic controller can selectively turn off the gyroscope during certain periods of time (e.g., as described with respect to FIG. 14) (step 1604). The accelerometer and gyroscopic measurements are used in conjunction (e.g., "fused") to obtain information regarding the device, such as the altitude or elevation of the device (step 1606). Further, this information can be used to determine other information about the device, such as the pose angle and direction from which an impact is experienced by the mobile device (step 1608). The mobile device determines whether a fall has occurred based on the measurements (step 1610).

Figure 17:
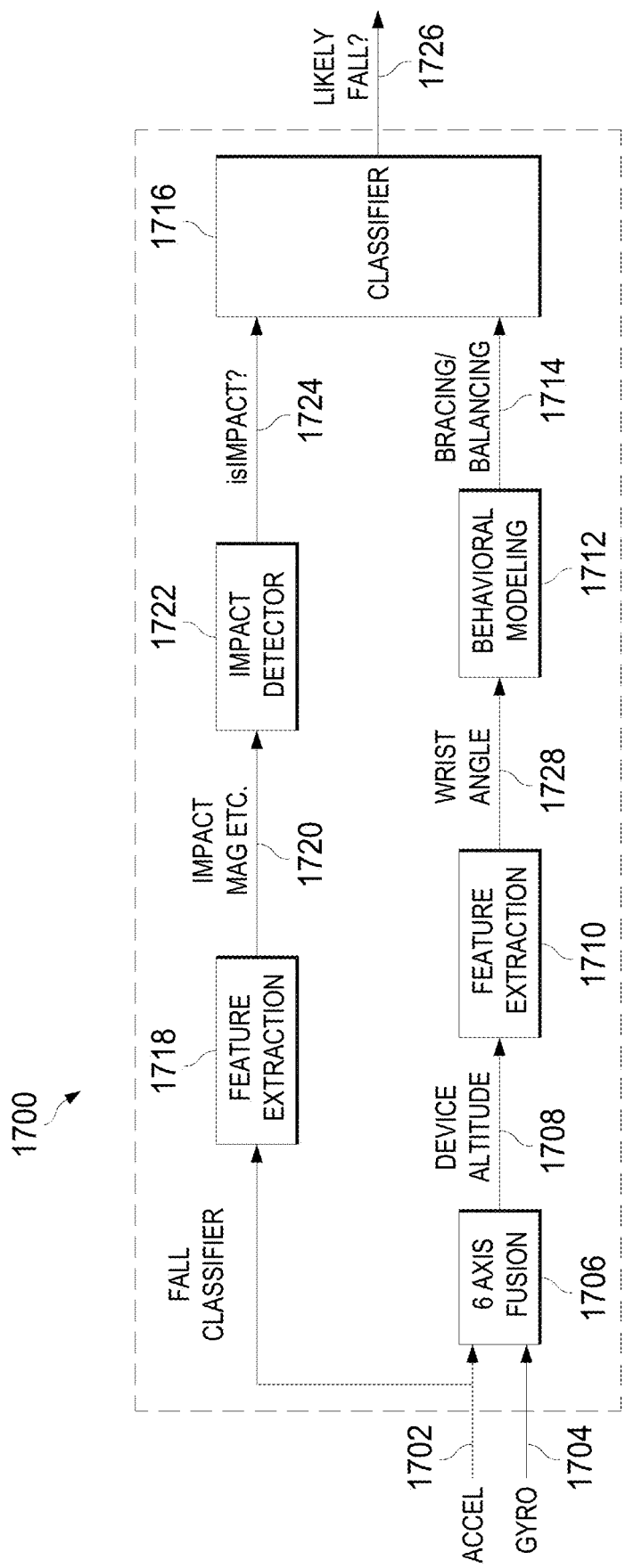
FIG. 17 is a schematic representation of an example fall classifier.

An example fall classifier 1700 is shown in FIG. 17. The fall classifier 1700 can be used to determine whether a user has fallen, and if so, the type or nature of the fall. The fall classifier 1700 can be implemented, for example, using one or more of the components of the system 100 shown in FIG. 1 (e.g., the mobile device 102).

The fall classifier 1700 receives inputs indicating the measured motion of the user, and outputs information indicating whether the user has fallen, and if so, the type or nature of the fall. For instance, as shown in FIG. 1700, the fall classier receives acceleration data 1702 indicating an acceleration experienced by a mobile device worn by a user (e.g., measured using an accelerometer), and gyroscopic data 1704 indicating an orientation of the mobile device (e.g., measured using a gyroscope).

The acceleration data 1702 and gyroscopic data 1704 are combined or "fused" together by a sensor fusion module 1706 (e.g., using one or more of the techniques described herein), and are considered in conjunction by the fall classifier 1700. In some cases, the acceleration data 1702 and the gyroscopic data 1704 can be combined with respect to one or more spatial axes (e.g., six).

The acceleration data 1702 and the gyroscopic data 1704 can be used in conjunction to determine information regarding the motion characteristics of the user. As an example, this data can be used to determine the altitude 1708 of the mobile device.

Further, the acceleration data 1702 and the gyroscopic data 1704 data can be input into a feature extraction module 1710, which identifies one or more features or characteristics of the acceleration data 1702 and the gyroscopic data 1704. The feature extraction module 1710 can perform one or more of the techniques described herein. As an example, the feature extractor 1710 can determine a wrist angle 1710 of the user (e.g., by determining a pose angle of the mobile device as it is worn by the user on his wrist).

Further, a behavior of the user can be determined using a behavioral modeling module 1712. The behavior of a user can be modeling one or more of the techniques described herein. As an example, based on changes of the pose angle of the mobile device 102, the behavioral modeling module 1712 can determine behavioral information 1714, such as whether the user is performing a bracing motion (e.g., thrusting his arms out to arrest forward momentum), a balancing motion (e.g., throwing his arms out to regain balance), a flailing motion (e.g., fluttering his arms during and after an impact), or another motion. In some cases, a bracing motion can be detected based on features such as the wrist traversing a negative arc length before impact, and the wrist pointing toward the ground at the moment of impact. In some cases, a balancing motion can be detected based on features such as the wrist traversing a positive arc length as the user attends to regain balance. In some cases, a failing motion can be detected based on features such as the wrist making a one or more rapid reversals in motion, either as part of a grasping reflex, or due to repeated secondary impacts with the ground. The behavioral information 1714 can be input into a classification module 1716 to aid in the detection and classification of falls.

The fall classifier 1700 can also analyze aspects of the acceleration data 1702 separately from the gyroscopic data 1704. For example, the acceleration data 1702 can be input into a feature extraction module 1718, which identifies one or more features or characteristics of the acceleration data 1702. The feature extraction module 1718 can perform one or more of the techniques described herein. As an example, the feature extractor 1718 can determine impact information 1720, such as the magnitude of an impact experienced by the user, motions made by the user prior to the impact, and motions made by the user after the impact. As another example, the feature extractor 1718 can determine a degree of chaos in the user's motions over a period of time.

The impact information 1720 can be input into an impact detector 1722, which determine if the user actually experienced an impact, and if so, the type or nature of the impact. The impact detector 1722 can perform one or more of the techniques described herein. As an example, the impact detector 1722 can output an indication 1724 regarding whether the user experienced an impact.

Information from the impact detector 1722 can the behavioral modeling module 1712 can be used to determine whether the user has fallen, and if so, the type or nature of the fall. As an example, based on inputs from a the impact detector 1722 and the behavioral modeling module 1712, the classification module 1716 can determine that the user has slipped, tripped, rolled, or experienced some other type of fall. As another example, based on inputs from the impact detector 1722 and the behavioral modeling module 1712, the classification module 1716 can determine that the user has experienced an impact, but has not fallen. As another example, based on inputs from the impact detector 1722 and the behavioral modeling module 1712, the classification module 1716 can determine that the user has fallen, but has recovered. The classification module 1716 outputs fall information 1726 indicating whether the user has fallen, and if so, the type or nature of the fall.

Figure 18:
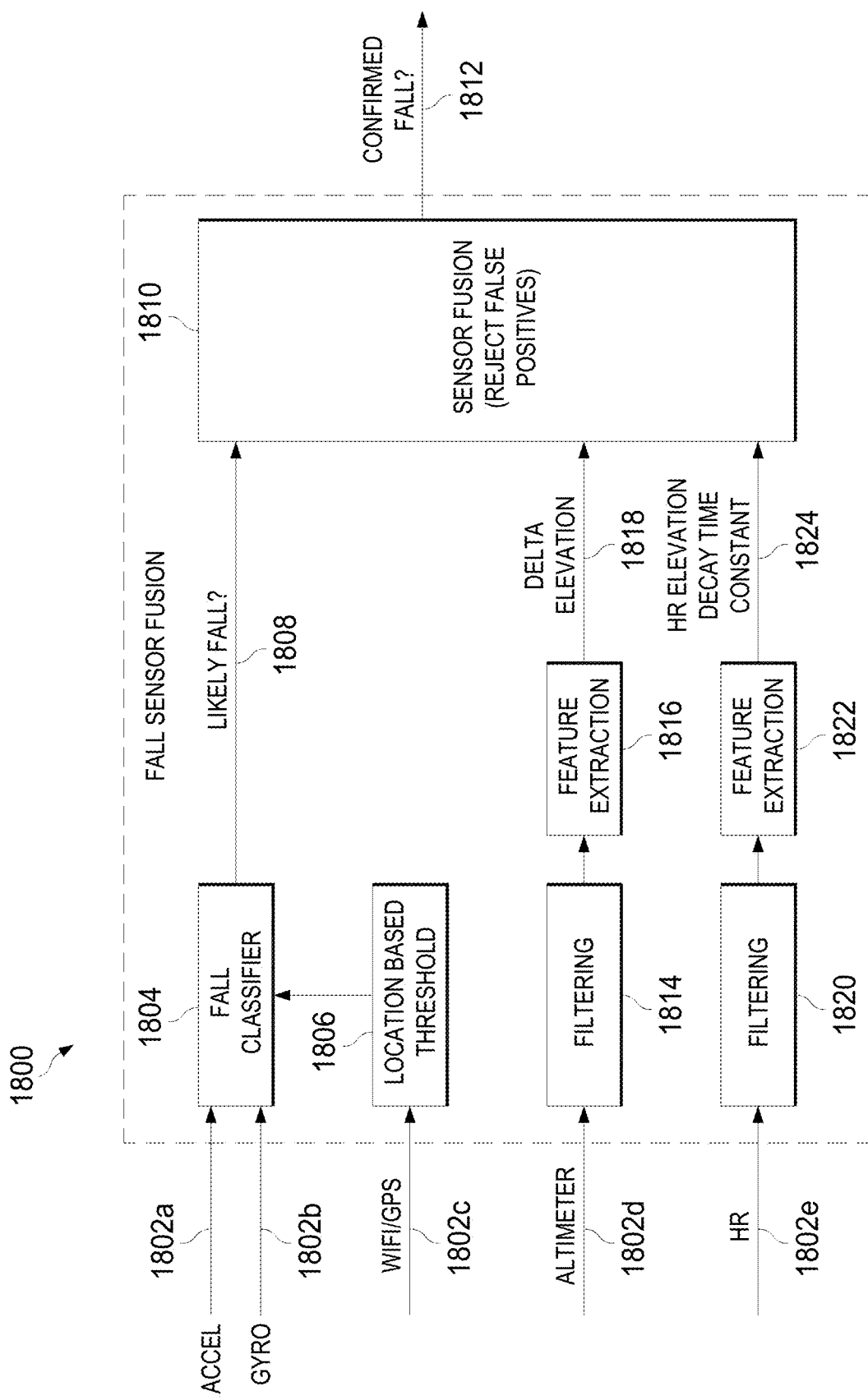
FIG. 18 is a schematic representation of an example fall sensor fusion module.

As described above, multiple types of sensor measurements can be used in conjunction to determine a user's motion characteristics. As an example, FIG. 18 shows a fall sensor fusion module 1800 used to determine whether a user has fallen, and if so, the type or nature of the fall. The sensor fusion module 1800 can be implemented, for example, using one or more of the components of the system 100 shown in FIG. 1 (e.g., the mobile device 102).

The fall sensor fusion module 1800 receives inputs from several different sensors. For example, the fall sensor fusion module 1800 receives acceleration data 1802a indicating an acceleration experienced by a mobile device worn by a user (e.g., measured using an accelerometer), and gyroscopic data 1802b indicating an orientation of the mobile device (e.g., measured using a gyroscope). As another example, the sensor fusion module 1800 receives location data 1802c indicating a location of the mobile device (e.g., measured using a Global Navigation Satellite System receiver, such as the Global Position System receiver, and/or a wireless transceiver, such as a Wi-Fi radio. As another example, the sensor fusion module 1800 receives altitude data 1802d indicating an altitude or elevation of the device (e.g., measured using an altimeter, barometer, or other altitude sensor). As another example, the sensor fusion module 1800 receives heart rate data 1802d indicating a heart rate of a user wearing the mobile device (e.g., measured using a heart rate sensor).

As described herein, the acceleration data 1802a and the gyroscopic data 1802b can be used to determine whether a user has fallen. For example, the acceleration data 1802a and the gyroscopic data 1802b can be input into a fall classifier 1804. In general, the fall classifier 1804 can function in a similar manner as described with respect to FIG. 17. For example, the fall classifier 1804 can determine one or more features based on the acceleration data 1802a, and determine whether the user experienced an impact based on those features. Further, the fall classifier 1804 can determine one or more features based on both the acceleration data 1802a and the gyroscopic data 1802b, and model a behavior of the user based on the features. Further, the fall classifier 1804 can determine whether a user has fallen based on the detected impacts and/or the modeled behavior.

Further, the fall classifier 1804 can determine whether a user has fallen based, at least in part, on the location data 1802c. For example, the location data 1802c can be input into a threshold module 1806. The threshold module 1806 determines information regarding the location of the mobile device 102. For example, the threshold module 1806 can determine whether the mobile device is at a user's home, at a user's place of work, at a public area (e.g., a store, gym, swimming pool, etc.), or some other location. As another example, the threshold module 1806 an determine whether the mobile device is being worn by the user while the user is driving, biking, skating, skateboarding, or traveling using some other mode of transportation. This information can be input into the fall classifier 1804 to improve the detection of falls. For example, a user may be more likely to fall while he is at home, rather than traveling in a car. Accordingly, the fall classifier 1804 can increase the sensitivity with which is detects falls upon determining that the user is at home, versus when the user is driving a car. As another example, a user may be more likely to fall while he is outside while it is snowing or raining, rather than when it is not snowing or raining. Accordingly, the fall classifier 1804 can increase the sensitivity with which is detects falls upon determining that the user is outside and determining that rain or snow is occurring at the location (e.g., based on information obtained from a weather service), versus when it is not raining or snowing at the user's location.

The fall classifier 1804 outputs fall data 1808 indicating whether the user has experienced a fall, and if so, the type or nature of the fall. The fall data 1808 can be input into a fusion module 1810, which rejects false positives by the fall classifier 1804. For example, the fusion module 1810 can receive fall data 1808 indicating that a fall was occurred. However, based on additional information received by the fusion module 1810, the fusion module 1810 can override the fall data 1808, and determine that a fall was not occurred. The fusion module 1810 outputs confirmation data 1812 confirming whether the user has experienced a fall, and if so, the type or nature of the fall.

In some cases, the fusion module 1810 can determine whether the fall data 1808 is a false positive based on the altitude data 1802*d*. For example, the altitude data 1802*d* can be input into a filter module 1814. The filter module 1814 can be used to isolate particular components of the altitude data 1802*d* (e.g., particular frequencies or frequency ranges). The filtered altitude data 1802*d* is input into a feature extraction module 1816, which determines feature data 1818 indicating one or more features of the altitude of the mobile device. As an example, the feature extraction module 1816 can determine the change in altitude or elevation of the mobile over a period of time. The feature data 1818 is input into the fusion module 1810, and can be used to identify potential false positives. For example, if the mobile device experienced a significant change in elevation (e.g., several feet, or several levels or stories), the fusion module 1810 may determine that a false positive is less likely. As another example, if the mobile device did not experience any change in elevation, the fusion module 1810 may determine that a false positive is more likely.

In some cases, the fusion module 1810 can determine whether the fall data 1808 is a false positive based on the heart rate data 1802*e*. For example, the heart rate data 1802*e* can be input into a filter module 1820. The filter module 1820 can be used to isolate particular components of the heart rate data 1802*e* (e.g., particular frequencies or frequency ranges). The filtered heart rate data 1802*e* is input into a feature extraction module 1822, which determines feature data 1824 indicating one or more features of the heart rate of the user wearing the mobile device. As another example, the feature extraction module 1822 can determine an elevation or increase of the user's heart rate after a fall. As another example, the feature extraction module 1822 can determine a subsequent decay or recovery of the heart rate (e.g., as the heart rate returns to normal). As another example, the feature extraction module 1822 can determine a decay time constraint associated with the decay or recovery in heart rate (e.g., a time constant indicating the rate of decay after elevation). The feature data 1824 is input into the fusion module 1810, and can be used to identify potential false positives. For example, if the user's heart rate increased (e.g., due to a fight-or-flight response), the fusion module 1810 may determine that a false positive is less likely. As another example, a user's rate heart often decays more quickly after a fall than after a period of exercise. Accordingly, the mobile device can compare the user's decay time constant to a decay time constant sampled after the user had exercised. If the user's decay time constant is smaller than the exercise-related decay time constant, the fusion module 1810 may determine that a false positive is less likely.

As described above, the mobile device can automatically transmit a distress call to a third party (e.g., an emergency responder) in response to detecting a fall, and determining that the user may be in need of assistance. In a similar manner as described above (e.g., with respect to FIG. 12), the mobile device can first alert a user regarding a potential transmission of a distress call (e.g., after a fall), and allow the user to confirm whether to proceed with the call. The user can manually initiate the distress call in response to the alert (e.g., can inputting a command into the mobile device). However, if the user does not respond to the alert, the mobile device can determine whether the call should proceed based on the user's behavior after the call. For example, if the user does not move after the fall (e.g., indicating that the user is injured or unresponsive), the mobile device can proceed with the call. However, if the user exhibits activity (e.g., indicating that the user has recovered), the mobile device can cancel the call. This gradual escalation can be beneficial, for example, in reducing the number of false positives regarding a fall, and decreasing the likelihood that a third party will be called unnecessarily.

Figure 19:
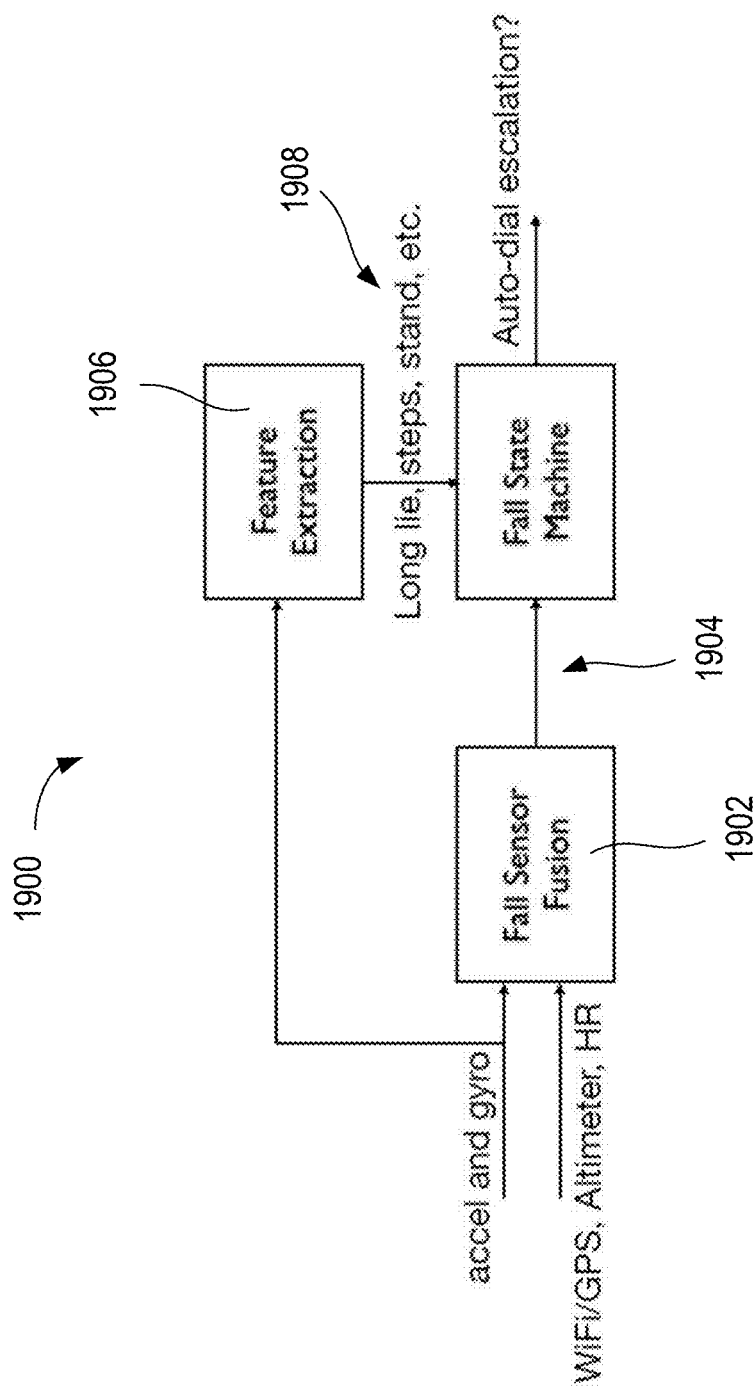
FIG. 19 is a schematic representation of an example distress call module.

In some cases, a mobile device can determine whether to transmit a distress call based on measurements obtained by several different sensors. As an example, FIG. 19 shows a distress call module 1900 used to determine whether to transmit a distress call to a third party. The distress call module 1900 can be implemented, for example, using one or more of the components of the system 100 shown in FIG. 1 (e.g., the mobile device 102).

The distress call module 1900 includes a fusion module 1902 for determining whether a user has fallen, and if so, the type or nature of the fall. The fusion module 1902 can operate in a similar manner as described with respect to FIG. 18. For example, the fusion module 1902 can receive several types of sensor data, such as acceleration data, gyroscopic data, location data, altitude data, and/or heart rate data. Based on this information, the fusion module 1902 can determine whether a user wearing the mobile device has fallen, and identify potential false positives. The fusion module 1902 outputs confirmation data 1904 confirming whether the user has experienced a fall, and if so, the type or nature of the fall.

Further, the distress call module 1900 determines information regarding the motion of the user wearing the mobile device. For example, the acceleration data and gyroscopic data can be input into a feature extraction module 1906. The feature extraction module 1906 determines one or more features regarding the motion of the user, such as whether the user has moved for a period of time after a fall, whether the user can taken any steps after a fall, whether the user has stood up after a fall, or other features. The feature extraction module 1906 outputs feature data 1908 indicating each of the extracted features.

Figure 20:
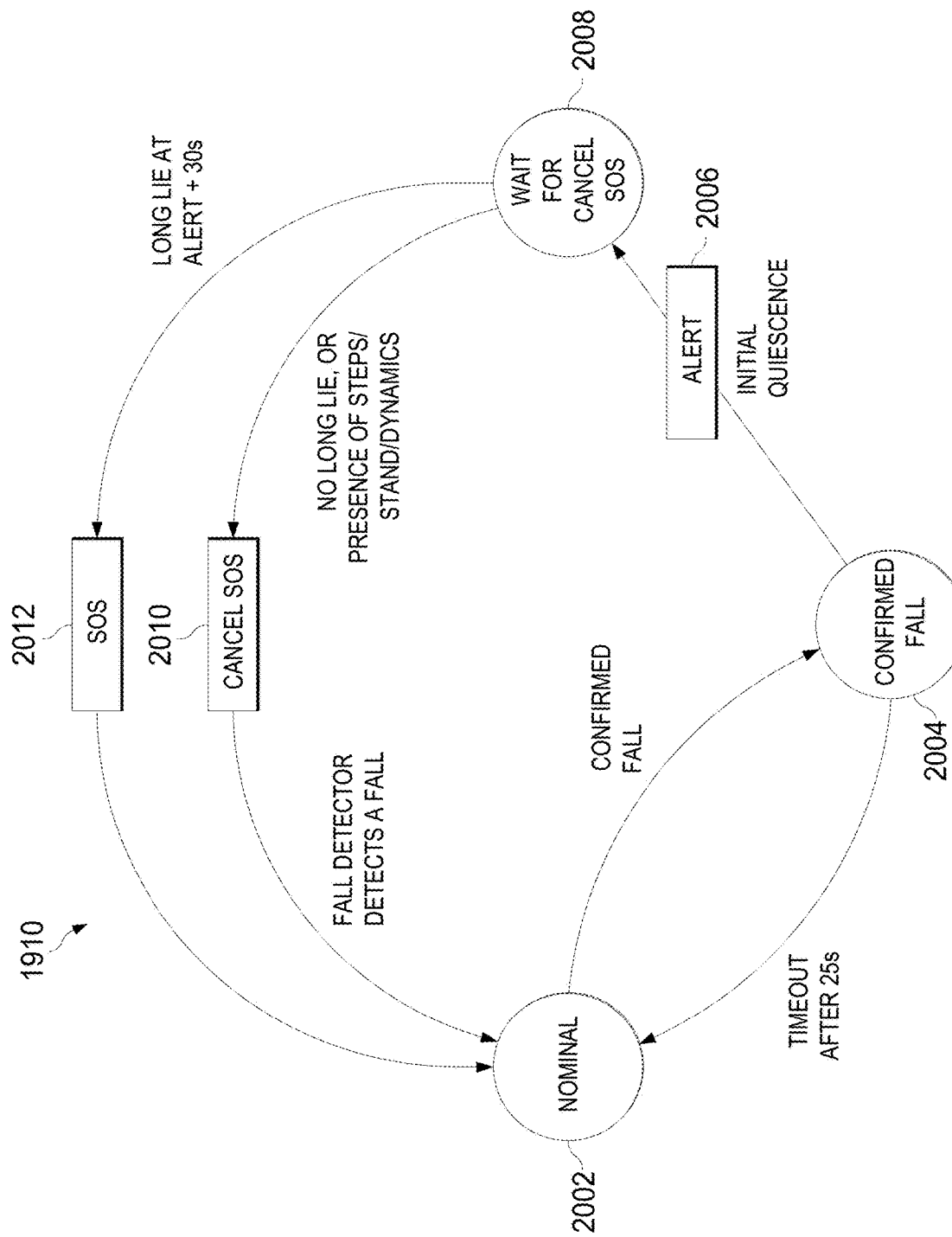
FIG. 20 is a schematic representation of an example fall state machine.

The confirmation data 1904 and the feature data 1908 can input into a fall state machine 1910. The fall state machine 1910 determines, based on the inputs, whether to transmit a distress call to a third party. An example fall state machine 1910 is shown in FIG. 20.

In this example, the mobile device begins in a "nominal" state 2002 (e.g., a low alert state), a "confirmed fall" state 2004 (e.g., an elevated alert state upon detection of a fall by the fusion module 1902), an "alert" state 2006 (e.g., a state in which the mobile device alerts the user of the mobile device regarding a fall and the possibility of sending a distress call to a third-party), a "wait" state 2008 (e.g., a state in which the mobile device waits for additional information, such as a potential input by a user), a "cancel" state 2010 (e.g., a state in which an impending distress call is canceled), and an "SOS" state 2012 (e.g., a state in which a distress call is conducted). The mobile device can transition between each of the states based on the detection of certain signatures of a fall (e.g., as described herein), detected periods of quiescence (e.g., a lack of movement by the user), and/or inputs by the user.

As an example, the mobile device begins at the "nominal" state 2002. Upon detection of a confirmed fall (e.g., by the fusion module 1902), the mobile device transitions of the "confirmed fall" state 2004. Upon detection of a period of quiescence $T_Q$ after the fall, the mobile device transitions to the "alert" state 2006, and alerts the user of the detected fall and informs the user of the possibility of sending a distress call to a third-party (e.g., an emergency responder). The mobile device transitions to the "wait" state 2008 and awaits input from the user in response to the alert. If no user movement is detected during a long-lie period of time $T_{LL}$ after the transmission of the fall alert (e.g., 30 seconds), the mobile device transmits to the "SOS" state 2012 and transmits the distress call. The mobile device then returns to the "nominal" state 2002. This can be useful, for example, if the user has fallen and becomes incapacitated for a lengthy period of time. The mobile device can automatically summon help for the user, even without the user's input.

As another example, the mobile device begins at the "nominal" state 2002. Upon detection of a confirmed fall, the mobile device transitions of the "confirmed fall" state 2004. Upon detection of certain types of movements after the fall within the period of quiescence $T_Q$ (e.g., stepping movements, standing movements, high dynamic movement, or any other movement indicative of recovery by the user), the mobile device returns to the "nominal" state 2002. This can be useful, for example, if the user has fallen, but exhibits signs of movement and recovery after the fall. The mobile device can refrain from alerting the user or automatically summoning help for the user under this circumstance.

As an example, the mobile device begins at the "nominal" state 2002. Upon detection of a confirmed fall (e.g., by the fusion module 1902), the mobile device transitions of the "confirmed fall" state 2004. Upon detection of a period of quiescence $T_Q$ after the fall, the mobile device transitions to the "alert" state 2006, and alerts the user of the detected fall and informs the user of the possibility of sending a distress call to a third-party (e.g., an emergency responder). The mobile device transitions to the "wait" state 2008 and awaits input from the user in response to the alert. Upon detection of certain types of movements within the long-lie period of time $T_{LL}$ after the transmission of the fall alert (e.g., stepping movements, standing movements, high dynamic movement, or any other movement indicative of recovery by the user), the mobile device transitions to the "cancel" state 2010, and does not transmit a distress call. The mobile device then returns to the "nominal" state 2002. This can be useful, for example, if the user has fallen, but exhibits signs of recovery. The mobile device can alert the user regarding the fall, but does not automatically summon help for the user under this circumstance.

Although time values are described with respect to FIG. 20, there are merely illustrative examples. In practice, one or more of the time values can differ, depending on the implementation. In some cases, one or more of the time values can be tunable parameters (e.g., parameters that are selected empirically to distinguish between different types or events or conditions).

In some cases, the system 100 can determine that the user 110 has fallen, determine the severity of the injury suffered by the user 110 due to the fall, and perform one or more actions (or refrain from performing one or more actions) in response. As an example, the system 100 can determine that a user 110 has fallen, but has suffered no injury or only a minor injury such that he is able to recover without assistance from others. In response, the system 100 can refrain from generating and transmitting a notification to others. As another example, a system 100 can determine that a user 110 has fallen and has suffered a more severe injury such that he may be in need of assistance. In response, the system 100 can generate and transmit a notification to others to assist the user.

Figure 21:
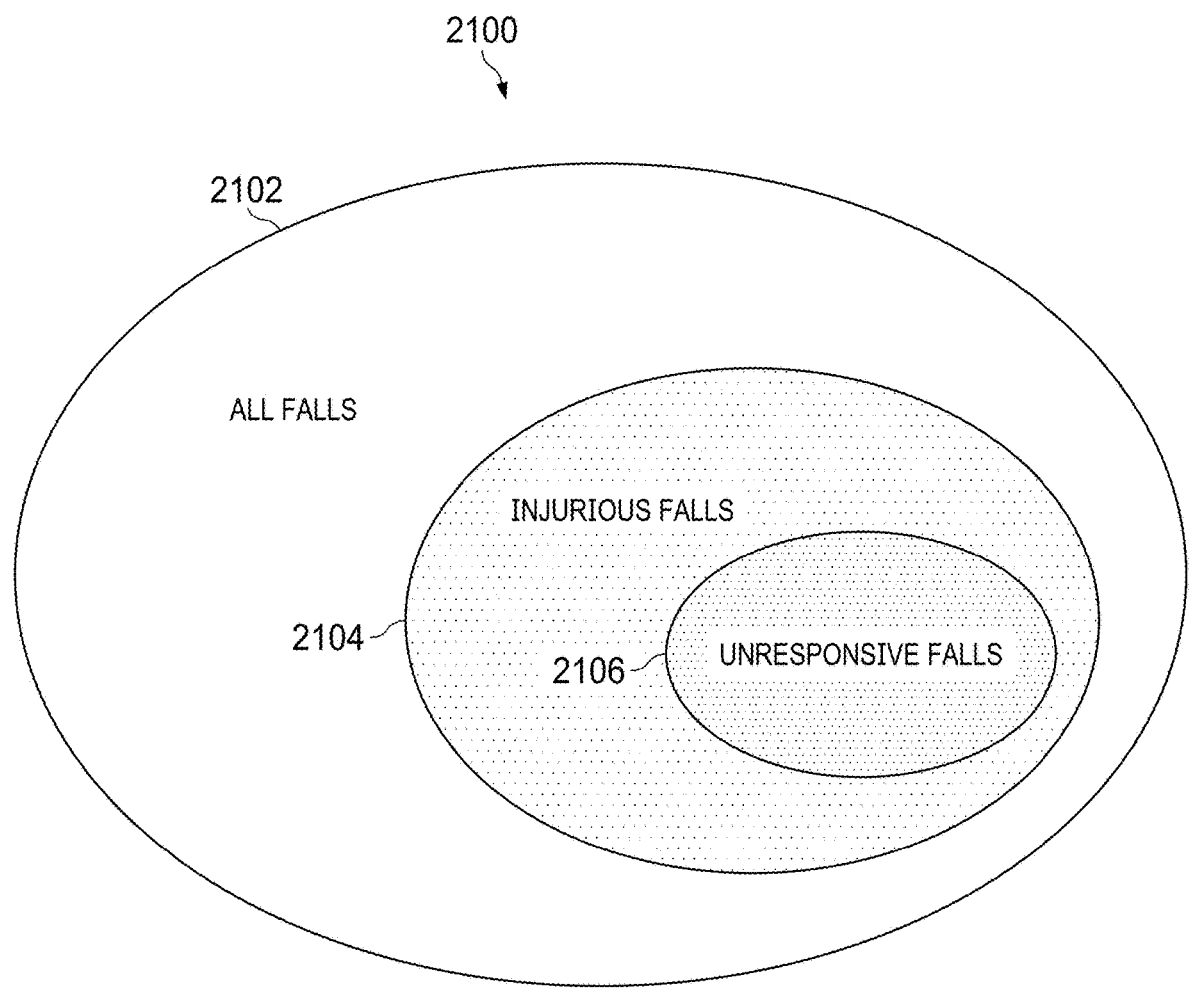
FIG. 21 is a diagram of different types of falls that may be experienced by a user

As an illustrative example, FIG. 21 shows a diagram 2100 classifying different types of falls that may be experienced by a user. In this example, the set of all of types of falls that may be experienced by a user is represented by a boundary 2102. Further, the subset of falls that result in injury to a user is represented by a boundary 2104 within the boundary 2102. Further, the subset of falls that result in injury to a user and cause the user to be unresponsive is represented by a boundary 2106 within the boundary 2104.

In some implementations, a system 100 can distinguish between each of these types of falls, and perform a different action in response. For example, if the user has suffered a fall that has injured him and rendered him unresponsive, the system 100 can generate and transmit a notification to others to assist the user, even if the user has not expressly instructed the system 100 to do so after the fall. As another example, if the user has suffered a fall that has injured him but has not rendered him unresponsive, the system 100 can generate and transmit a notification to others to assist the user (e.g., after receiving confirmation from the user to do so after the fall). As another example, if the user has suffered a fall that has neither injured him nor rendered him unresponsive, the system 100 can refrain from generating and transmitting a notification to others to assist the user.

Although example categories or types of falls are shown in FIG. 21, these are merely illustrative examples. In practice, falls can be classified according to other categories or types, either instead or in addition to those shown in FIG. 21.

As described herein, in some implementations, the system 100 can determine whether the user has fallen based on motion data obtained before, during, and/or after an impact experienced by the user 110. In some implementations, the system 100 can make this determination by detecting the motion characteristics of a user, and determining whether the motion characteristics are indicative of a user experiencing an impact, anticipating a fall (e.g., performing a bracing motion), and/or reacting to a fall. Based on this information, the system 100 can determine a probability that the user experienced a fall.

Figure 22A:
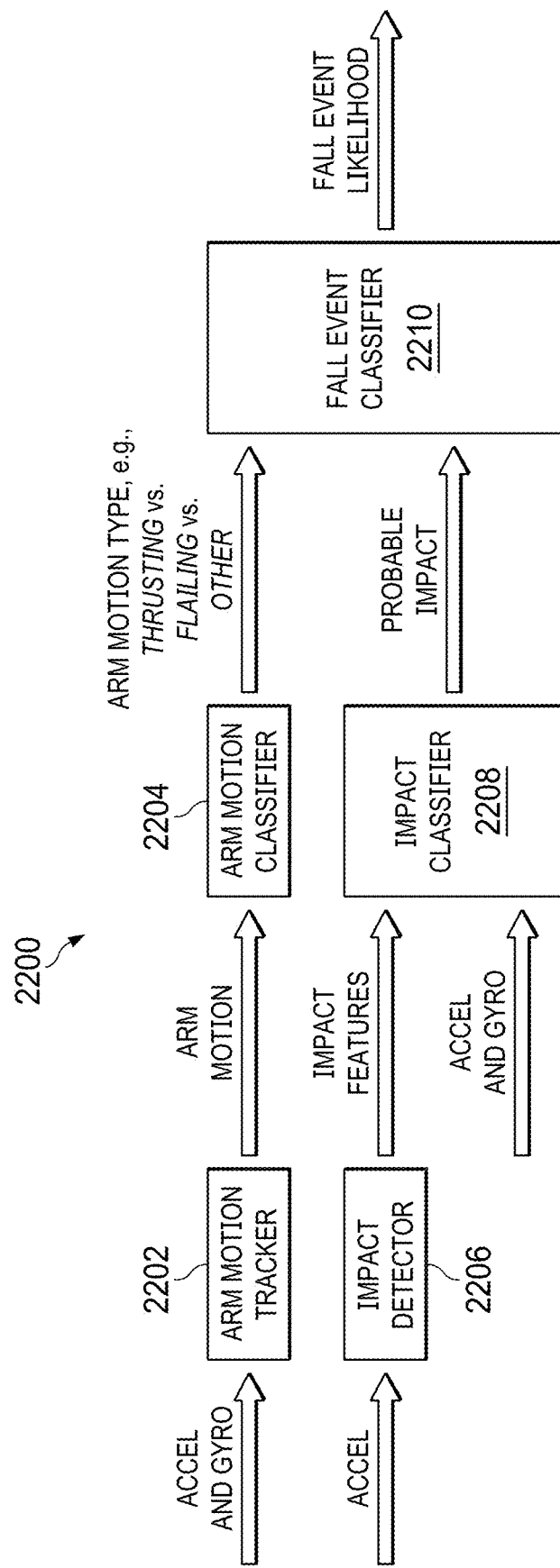
FIG. 22A is a schematic representation of an example fall detection module.
Figure 22B:
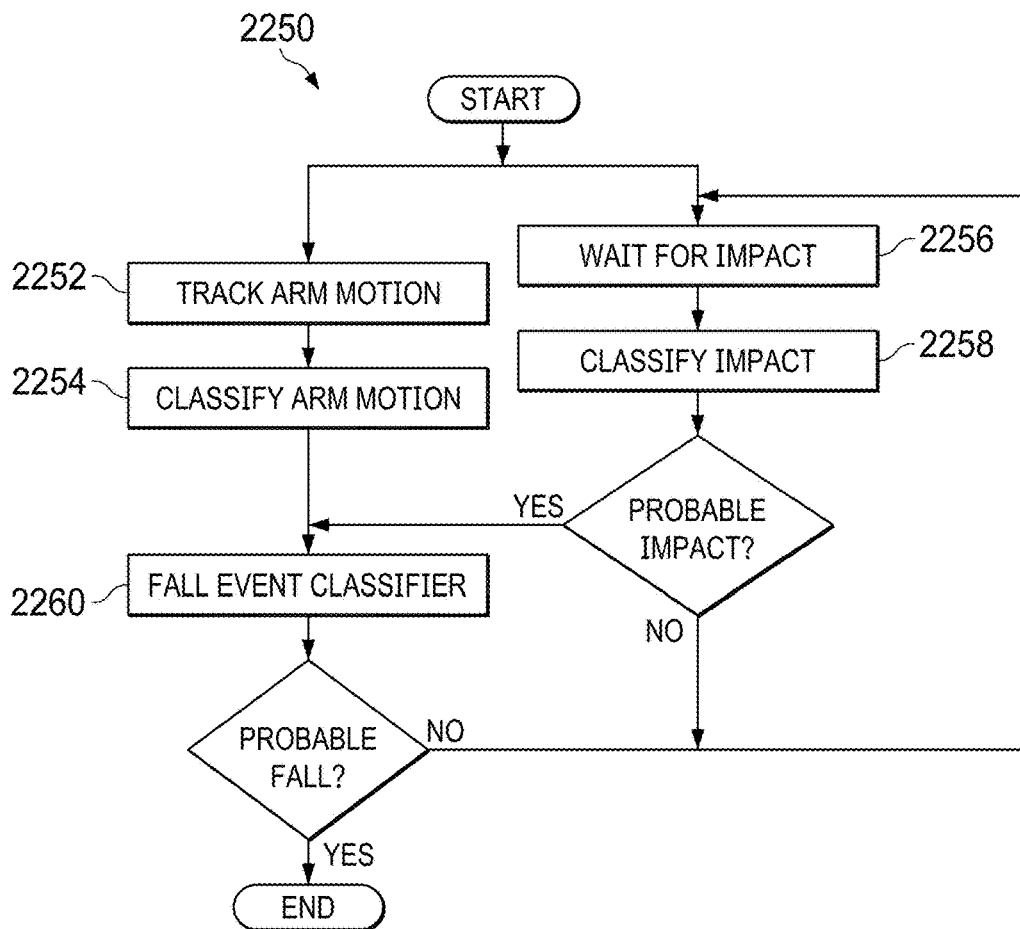
FIG. 22B is flow chart diagram of an example process for determining a likelihood that a user has fallen.

An examples, FIG. 22A shows an fall detection module 2200, and FIG. 22B shows an process 2250 can be performed at least in part by the fall detection module 2200. The fall detection module 2200 can be implemented, for example, one or more of the components of the system 100 shown in FIG. 1 (e.g., the mobile device 102).

As shown in FIG. 22A, the fall detection module 2200 includes an arm motion tracker module 2202, an arm motion classifier module 2204, an impact detector module 2206, and impact classifier module 2208, and a fall event classifier module 2210.

During operation of the fall detection module 2200, the arm motion tracker module 2202 receives sensor measurements from one or more sensors worn by a user on his arm. For example, the arm motion tracker module 2202 can receive acceleration data obtained from one or more accelerometers worn by the user on his arm, and orientation data obtained from one or more gyroscopes worn by the user on his arm. Based on these sensor measurements, the arm motion tracker module 2202 determines the motion of a user's arm over a period of time. For example, the arm motion tracker module 2202 can determine that the user has rotated along one or more axes and/or translated along one or more axes.

The arm motion tracker module 2204 provides information regarding the motion of the user's arm to the arm motion classifier module 2204. Based on this information, the arm motion classifier module 2204 determines a type of motion performed by the user's arm. As an example, the arm motion classifier module 2204 can determine the user has performed a bracing motion (e.g., thrusting his arms out to arrest forward momentum), a balancing motion (e.g., throwing his arms out to regain balance), a flailing motion (e.g., fluttering his arms during and after an impact), or another motion using his arm. Example techniques for classifying the motion of a user's arm are described, for instance, with respect to FIG. 6. The arm motion tracking module 2204 provides information regarding the type of motion performed by the user's arm to the fall event classifier module 2210 for further processing.

During operation of the fall detection module 2200, the impact detector module 2206 also receives sensor measurements from one or more sensors worn by a user on his arm. For example, the impact detector module 2206 can receive acceleration data obtained from one or more accelerometers worn by the user on his arm. Based on these sensor measurements, the impact detector module 2206 determines one or more features or characteristics that may be indicative of an impact experienced by a user over a period of time. For example, the impact detector module 2206 can determine the magnitude of the acceleration measured by the one or more features with respect to one or more dimensions, a jerk measured by the one or more features with respect to one or more dimensions, a time associated with each of the measurements, and/or any other property that may be indicative of an impact.

The impact detector module 2206 provides information regarding the determined features or characteristics to the impact classifier module 2208. Based on these sensor measurements, the impact classifier module 2208 determines a likelihood that the user has experienced an impact. The impact classifier module 2208 can also use additional sensor information to make this determination. For example, the fall detection module can make this determination based on acceleration data obtained from one or more accelerometers worn by a user on his arm, and orientation data obtained from one or more gyroscopes worn by a user on his arm. The impact classifier module 2208 provides information regarding the likelihood that the user has experienced an impact to the fall event classifier module 2210 for further processing.

The fall event classifier module 2210 determines a likelihood that the user experienced a fall based on the information received from the arm motion classifier module 2204 and the impact classifier module 2208. For example, the fall event classifier module 2210 can determine that the user is more likely to have experienced a fall if the user has experienced an impact. As another example, the fall event classifier module 2210 can determine that the user is more likely to have experienced a fall if the user's arm was moved in a particular manner prior to an impact (e.g., the user thrusted his arm forward, flailed his arm, etc.).

In some embodiments, the fall detection module 2200 can determine a likelihood that a user has fallen using the process 2250 shown in FIG. 22B. According to the process 2250, the fall detection module 2200 tracks the motion of a user's arm (e.g., using sensor data from one or more sensor worn by the user on his arm, and the arm motion tracker module 2202) (step 2252). Based on the sensor measurements, the fall detection module 2200 determines a type of motion performed by the user's arm (e.g., using the arm motion classifier module 2204) (step 2254). As an example, the arm motion classifier module 2204 can determine the user has performed a bracing motion, a balancing motion, a flailing motion, or another motion using his arm.

Concurrently with tracking the motion of a user's arm and determining the type of motion performed by the user's arm, the fall detection module 2200 collects sensor data that may be indicative of a user experiencing an impact (e.g., using the impact detector module 2206) (step 2256). Based on the sensor data, the fall detection module 2200 determines a likelihood that the user has experienced an impact (e.g., using the impact classifier module 2208) (step 2258). If the fall detection module 2200 determines that the user is unlikely to have experienced an impact, the fall detection module 2200 continues collecting sensor data and waiting for the occurrence of an impact.

If the fall detection module 2200 determines that the user is likely to have experience an impact, the fall detection module 2200 determines a likelihood that the user has experienced a fall (e.g., using the fall event classifier module 2210) (step 2260). If the fall detection module 2200 determines that the user is unlikely to have experienced a fall, the fall detection module 2200 continues collecting sensor data and waiting for the occurrence of an impact and tracking the motion of the user's arm.

If the fall detection module 2200 determines that the user is unlikely to have experienced a fall, the fall detection module 2200 can provide this information to the system 100. Based on this information, the system 100 can determine whether to perform one or more actions (or refrain from performing one or more actions) in response to the determination. For example, the system 100 to can generate and transmit a notification to others to assist the user (or refrain from doing so), such as using one or more of the techniques described herein.

As described herein, in some implementations, a system 100 can determine whether a user is has fallen and is in need of assistance based on the activity level of a user. For instance, an athletic user who is highly active (e.g., historically exhibits frequent and intense movements) may be at a lower risk of falling in a manner that requires assistance. However, a frail user who is not active (e.g., historically exhibits infrequent and slight movements) may be at a higher risk of falling in a manner that requires assistance.

Figure 23:
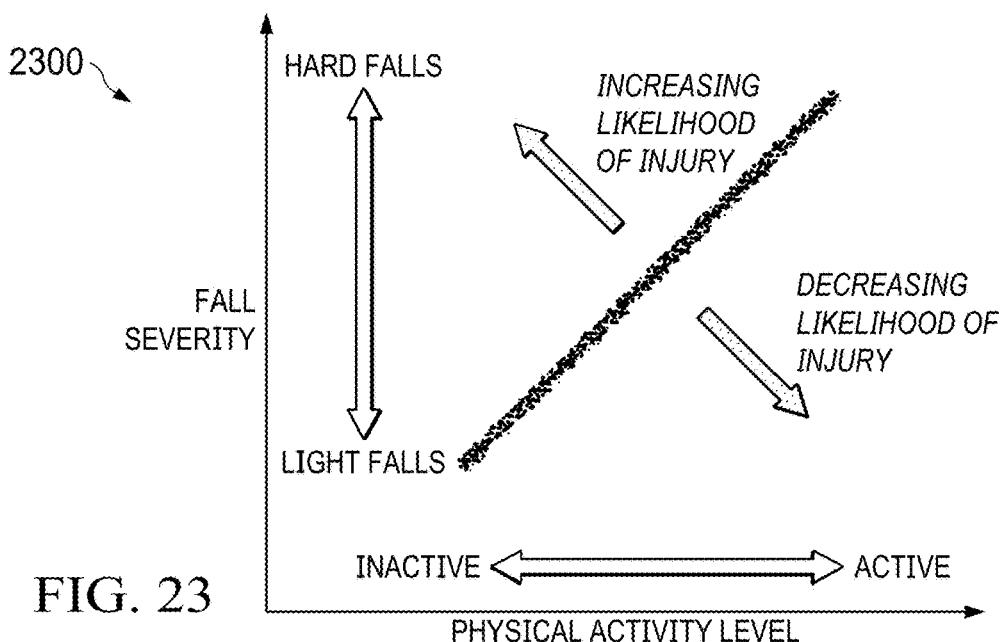
FIG. 23 shows an example plot of a user's physical historical activity level and an expected severity of a fall experienced by the user.

As an example, FIG. 23 shows an example plot of a user's physical activity level (horizontal axis) and an expected severity of a fall experienced by the user (vertical axis). Users that have a relatively higher physical activity level (e.g., corresponding to the right portion of the plot) may be expected to experience less severe falls (e.g., corresponding to the lower portion of the plot). Accordingly, for these users, the system 100 can be configured such that it is less likely to generate and transmit a notification to other users (e.g., to reduce false positives).

In contrast, users that have a relatively lower physical activity level (e.g., corresponding to the left portion of the plot) may be expected to experience more severe falls (e.g., corresponding to the upper portion of the plot). Accordingly, for these users, the system 100 can be configured such that it is more likely to generate and transmit a notification to other users (e.g., to reduce false negatives).

In some implementations, the activity level of a user can be determined based on factors such as the user's age and/or historical information regarding a user's physical activities over time (e.g., the average number of steps that the user takes each day).

As described herein, in some implementations, the system 100 can determine that a user is likely to have fallen, and selectively performing certain actions (e.g., generating and transmitting a notification to others) depending on the motion characteristics of the user before and after the fall. For instance, in some implementations, the system 100 can compare the user's activities prior to the fall to the user's activities after the fall. If after a fall, the user cannot resume his pre-fall activities, the system 100 can determine that the user may have suffered from an injury and perform one or more actions in response (e.g., generate and transmit a notification to others to assist the user).

Figure 24:
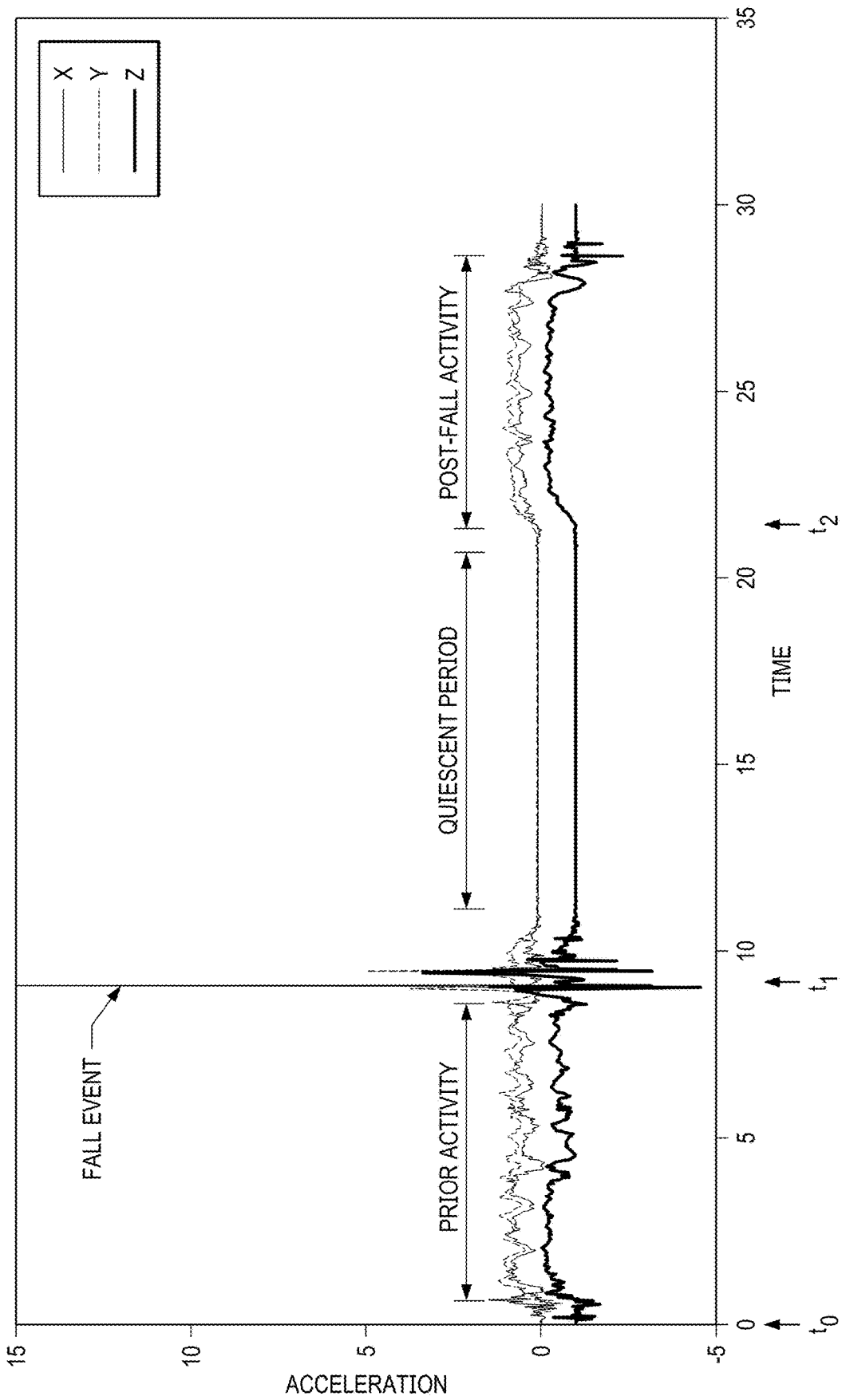
FIG. 24 shows example acceleration data collected by accelerometers positioned on a user's body before a fall, at the time of the fall, and after the fall.

As an example, FIG. 24 shows example acceleration data 2400 collected by accelerometers positioned on a user's body before a fall (the time interval $t_0$ to $t_1$), at the time of the fall (time $t_1$), and after the fall (time interval after $t_1$). In this example, the user performed a physical activity prior to the fall (corresponding to variations in the acceleration data collected during the time interval $t_0$ to $t_1$), and experienced a fall at the time $t_1$ (corresponding to a large spike in the accelerometer data collected at time $t_1$). After the fall, the user did not move during a "quiescent" period of time (corresponding to little to no variation in the acceleration data collected after the fall until a time $t_2$). As an example, the user may have been stunned from the fall and/or was recovering from the fall. After the quiescent period of time, the user began moving again (corresponding to variations in the acceleration data collected after the time $t_2$).

Figure 25:
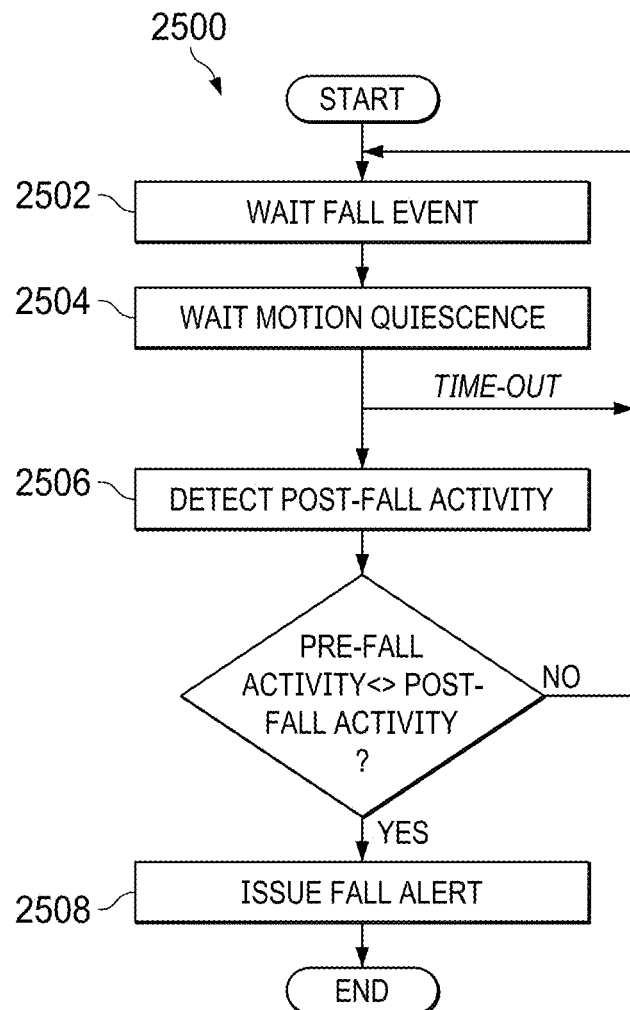
FIG. 25 is a flow chart diagram of an example process for generating and transmitting a notification.

The system 100 can determine whether to perform certain actions (e.g., generating and transmitting a notification to others) depending on the motion characteristics of the user before and after the fall. As an example, FIG. 25 shows an example process 2500 for generating and transmitting a notification. The process 2500 can be implemented, for example, one or more of the components of the system 100 shown in FIG. 1 (e.g., the mobile device 102).

According to the process 2500, a device (e.g., the mobile device 102 and/or one or more other components of the system 100) gathers sensor data from one or more sensors positioned on a user's body, and uses the sensor data to determine whether the user has fallen (step 2502). Example techniques for determining whether a user has fallen are described herein.

Upon determining that the user has fallen, the device waits for a "quiescent" period of time after the fall (step 2504). During this time, the device does not generate and transmit any notifications to others. However, the device continues to gather sensor data to track the motion of the user. In practice, the length of the quiescent period of time can vary, depending on the implementation. In some implementations, the quiescent period of time can be selected empirically.

After the quiescence period of time has passed, the device determines the type of activity that is being performed by the user (step 2506). As an example, device can determine that the user is performing a certain type of activity, such as walking, running, swimming, playing a sport, etc. This determination can be made, for example, using an activity classifier based on the sensor data (e.g., as described herein).

Further, the device compares the user's "post-fall" activity to the user's "pre-fall" activity (step 2508). The user's pre-fall activity can be determined in a similar manner as in the user's post-fall activity. For example, the type of activity that the user was performing prior to the fall can be determined by an activity classifier based on sensor data gather prior to the fall.

If the user's pre-fall activity is not the same as (or is not substantially similar to) the pre-fall activity (e.g., free-fall activity< >post-fall activity, or free-fall activity≠post-fall activity), the device can perform one or more actions in response. For instance, the device can generate and transmit a notification to others to assist the user (step 2508). As an example, if the user was running prior to the fall, but is no longer running in the "post-fall" period, the device can determine that the user may be injured, and can summon help for the user. As an example, if the user was swimming prior to the fall, but is no longer swimming in the "post-fall" period, the device can determine that the user may be injured, and can summon help for the user.

If the user's pre-fall activity is the same as (or substantially similar to) the pre-fall activity (e.g., free-fall activity=post-fall activity), the device can refrain from generating and transmitting a notifications to others, but can continue gathering sensor data and monitoring the user for falls. As an example, if the user was running prior to the fall, is also running in the "post-fall" period, the device can determine that the user is unlikely to be injured, and can refrain from summing help for the user.

Figure 26:
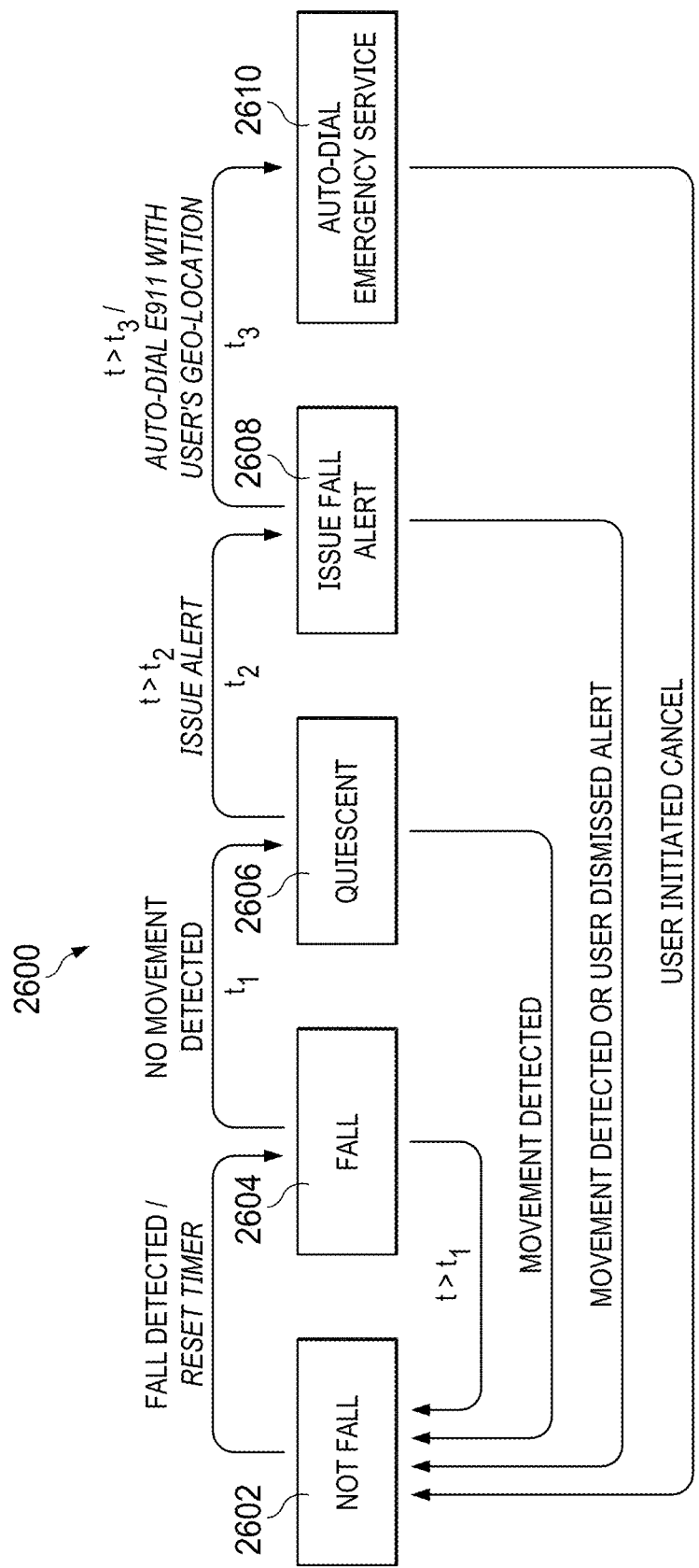
FIG. 26 is a diagram of an example state machine for determining whether to generate and transmit a notification.

As described herein, the system 100 can determine whether to generate and transmit a notification to others using a state machine. An example state machine is shown in FIG. 26. In this example, a device (e.g., a mobile device 102) begins in a "no fall" state 2602 (e.g., corresponding to an absence of a detected fall by a user). If the device determines that the user has fallen (e.g., at a time $t_0$), the device transitions to a "fall" state 2604, and resets a timer. After the reset, the timer begins increasing over time.

After transition to the "fall" state, the device waits for a first period of time (e.g., until a time $t_1$ after the time $t_0$). This can be beneficial, for example, as it enables the user's movements to "settle" after a fall, prior to the device analyzing the nature of the fall and deciding whether to take any action. In practice, the length of the first period of time can vary, depending on the implementation. For example, the length of the first period of time can be one second, two seconds, three seconds, or any other period of time. In some implementations, the length of the second period of time can be selected empirically.

After waiting for the first period of time, the device determines whether the user has moved during a second period of time (e.g., between the time $t_1$ and a time $t_2$, where time $t_2$ is after time $t_1$) (state 2606). If the device determines that the user has moved during the second period of time (e.g., between the time $t_1$ and a time $t_2$), the device returns to the "not fall" state 2602, and refrains from generating and transmitting a notification to others regarding the detected fall. In practice, the length of the second period of time can vary, depending on the implementation. For example, the length of the second period of time can be one second, two seconds, three seconds, or any other period of time. In some implementations, the length of the second period of time can be selected empirically.

The device can determine whether the user has moved based on measurements obtained by one or more sensors worn by the user. For example, the device can receive acceleration measurements obtained by one or more acceleration sensors worn by the user. If the acceleration measurements change by a sufficiently large degree during the second period of time after the detected fall (e.g., the change in acceleration exceeds a particular threshold level), the device can determine that the user has moved after the fall. As another example, the device can receive orientation measurements obtained by one or more orientation sensors (e.g., gyroscopes) worn by the user. If the orientation measurements change by a sufficiently large degree during the second period of time after the detected fall (e.g., the change in orientation exceeds a particular threshold level), the device can determine that the user has moved after the fall. In some implementations, the threshold levels and/or the length the second period of time can be selected empirically (e.g., based on experimental studies that identify differences between situations in which a user requires assistance and situations in which a user does not).

As another example, in some implementations, the device can determine whether the user has moved by determining whether the user is walking or has stood up within the second period of time after the detected fall. As an example, the device can obtain acceleration measurements (e.g., obtained by one or more acceleration sensors), orientation measurements (e.g., obtained by one or more orientation sensors, such as gyroscopes), altitude measurements (e.g., obtained by one or more altitude sensors, such as barometers), and/or other measurements obtained by one or more sensors worn by the user. If the device determines that the measurements are indicative of the user walking and/or standing up during the second period of time after the detected fall, the device can determine that the user has moved. In some implementations, the device can make this determination by determining whether the measurements match or are sufficiently similar to pre-determined patterns of measurements known to be indicative of a user walking or standing. In some implementations, the time interval and/or the pre-determined patterns of measurements can be selected empirically (e.g., based on experimental studies that identify distinguishing characteristics in measurements of users walking and/or standing, versus measurements of users performing other types of activities).

If the device determines that the user has not moved during the second period of time, the device transitions to an "alert" state 2608, and prepares to summon assistance for the user. For example, at the end of the second period of time (e.g., at the time $t_2$), the device can present a notification to the user (e.g., a visual, auditory, and/or haptic notification) indicating that a request for assistance will be transmitted. If the user does not instruct the device to cancel the transmission by the end of a third period of time (e.g., between the time $t_2$ and a time $t_3$, where time $t_3$ is after time $t_2$), the device can transition to an "auto-dial" state and automatically transmit a notification to an emergency responder (state 2610). For example, the device can automatically dial an emergency response system, such as "911," or initiating some other communication session. This can be beneficial, for example, as it provides the user with an opportunity to manually cancel a transmission if assistance is not required. However, the device will proceed with the transmission if the user does not respond (or is unable to respond). In practice, the length of the third period of time can vary, depending on the implementation. For example, the length of the third period of time can be one second, two seconds, three seconds, or any other period of time. In some implementations, the length of the third period of time can be selected empirically.

Further, device can provide information to assistant the emergency responder in locating and treating the user. For example, the device can transmit the location of the user (e.g., as determined through a location determining subsystem of the device), the nature of the emergency, or other information.

When the device is in the auto-dial state 2610, the user can also instruct the device to cancel the automatic notification and/or terminate the communication system. For example, prior to the time $t_3$, the user can instruct the device to cancel the automatic notification. In response, the device transitions back to the "not fall" state 2602 and refrains from generating and transmitting a notification to others. As another example, after the time $t_3$, the user can instruct the device to cancel the automatic notification. In response, the device transitions back to the "not fall" state 2602 and terminates the transmission.

In some implementations, the system 100 can determine the severity of an injury suffered by the user 110 due to a fall based on multiple types of sensor data. For example, the system 100 can make this determination based on accelerometer data that is indicative of a user's movements, gyroscope data that is indicative of changes in the orientation of the user's body, and altimeter data that is indicative of a user's change in altitude.

Figure 27:
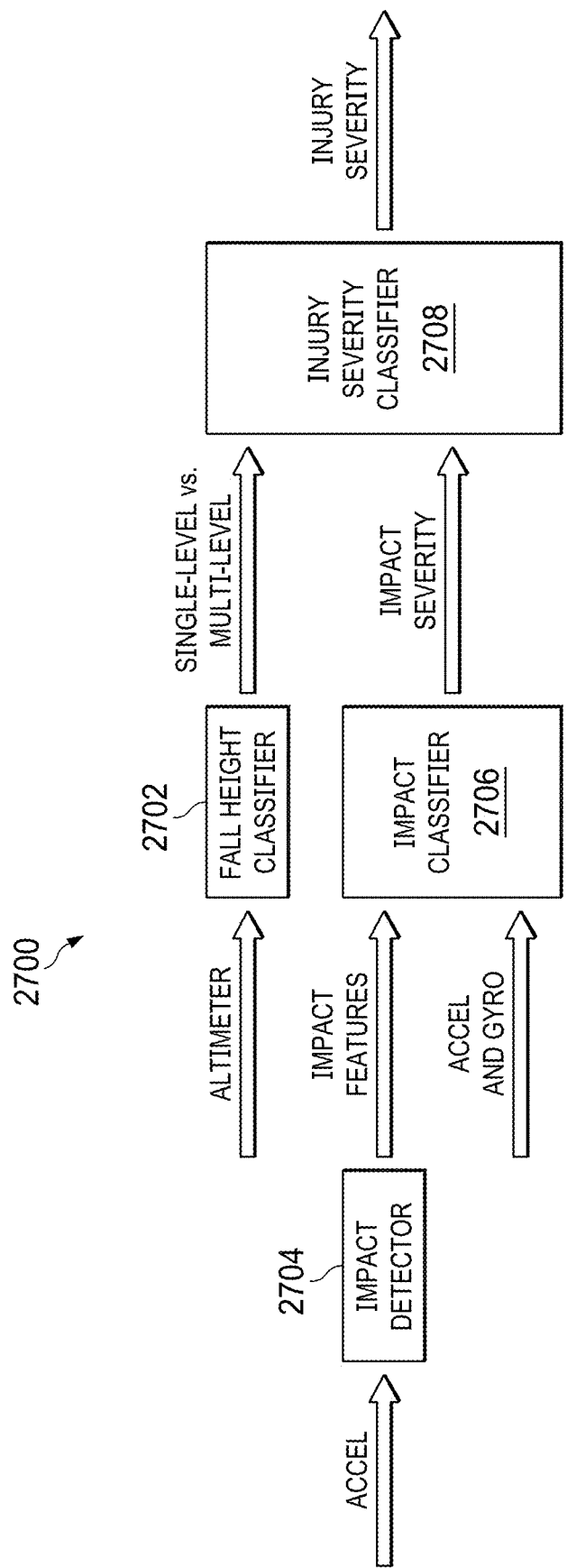
FIG. 27 is as schematic representation of shows a fall detection module for determining a severity of a user's injury due to a fall.

As an example, FIG. 27 shows a fall detection module 2700 for determining a severity of a user's injury due to a fall. The fall detection module 2700 can be implemented, for example, one or more of the components of the system 100 shown in FIG. 1 (e.g., the mobile device 102).

As shown in FIG. 27, the fall detection module 2700 includes a fall height classifier module 2702, an impact detector module 2704, and impact classifier module 2706, and an injury severity classifier module 2708.

During operation of the fall detection module 2700, the fall height classifier module 2702 receives sensor measurements from one or more sensors worn by a user on his body. For example, the fall height classifier module 2702 can receive altitude data obtained from one or more altimeters worn by the user on his body. Based on these sensor measurements, the fall height classifier module 2702 determines the altitude of a user over a period of time.

Further, the fall height classifier module 2702 can classify changes in the user's altitude over time. For example, based on the sensor data, the fall height classifier module 2702 can determine whether a user's altitude changed in a way that is indicative of the user falling a relatively shorter distance (e.g., a "single level" fall, such as falling down a flight of stairs) or the user falling a relatively longer distance (e.g., a "multi-level" fall, such as falling from a ladder or balcony"). In some implementations, the fall height classifier module 2702 can make this determination by determining a change in the user's altitude over a particular period of time, and determining whether that chance in altitude falls within different ranges (e.g., a relatively shorter distance range for single level falls, or a relatively longer distance range for multi level falls). The ranges can be determined empirically (e.g., based on observations of test subjects falling under various conditions).

Although two example classifications are described above, these are merely illustrative examples. In practice, the fall height classifier module 2702 can classify changes in the user's altitude according to any number of difference classes or types, either instead of or in addition to those described above.

During operation of the fall detection module 2700, the impact detector module 2704 also receives sensor measurements from one or more sensors worn by a user on his arm. For example, the impact detector module 2704 can receive acceleration data obtained from one or more accelerometers worn by the user on his arm. Based on these sensor measurements, the impact detector module 2704 determines one or more features or characteristics that may be indicative of an impact experienced by a user over a period of time. For example, the impact detector module 2704 can determine the magnitude of the acceleration measured by the one or more features with respect to one or more dimensions, a jerk measured by the one or more features with respect to one or more dimensions, a time associated with each of the measurements, and/or any other property that may be indicative of an impact.

The impact detector module 2704 provides information regarding the determined features or characteristics to the impact classifier module 2706. Based on these sensor measurements, the impact classifier module 2706 determines a severity of an impact experienced by the user. The impact classifier module 2706 can also use additional sensor information to make this determination. For instance, the fall detection module can make this determination based on acceleration data obtained from one or more accelerometers worn by a user on his arm, and orientation data obtained from one or more gyroscopes worn by a user on his arm. As an example, the impact classifier module 2706 can classify an impact as more severe if changes in the sensor data are higher in magnitude (e.g., the variation in acceleration, jerk, and/or orientation is higher). As another example, the impact classifier module 2706 can classify an impact as less severe if changes in the sensor data are lower in magnitude (e.g., the variation in changes in acceleration, jerk, and/or orientation is lower). The impact classifier module 2706 provides information regarding the severity of the impact experienced by the user to the injury severity classifier module 2708 for further processing.

The injury severity classifier module 2708 determines a severity of an injury suffered by the user based on the information received from the fall height classifier module 2702 and the impact classifier module 2706. For example, injury severity classifier module 2708 can determine that the user is more likely to have experienced a severe injury if the user has experienced a severe impact and/or has fallen a longer distance. As another example, injury severity classifier module 2708 can determine that the user is more likely to have experienced a less severe injury if the user has experienced a less severe impact and/or has fallen a shorter distance.

As another example, the injury severity classifier module 2708 can determine that the user is more likely to have experienced a severe injury if the user has experienced multiple impacts over time. As another example, injury severity classifier module 2708 can determine that the user is more likely to have experienced a less severe injury if the user has experienced fewer impacts over time.

As another example, the injury severity classifier module 2708 can determine that the user is more likely to have experienced a severe injury if the user has experienced multiple impacts over time, where at least some of the impacts are dissimilar to one another. This can be beneficial, for example, as tumbling falls (in which the user is more likely to experience multiple varying impacts in a sequence) may be more likely to result in severe injury.

For instance, the severity classifier module 2708 can determine, for each impact experienced by the user, a set of characteristics associated with that impact. The characteristics can include, for example, the magnitude of the impact, the distance fallen by the user, the axis or axes of rotation of the user, the acceleration of the user, the jerk of the user, the orientation of the user, any changes thereof, and/or any other characteristic of the impact. The injury severity classifier module 2708 can determine that the user is more likely to have experienced a severe injury if the user experienced impacts that are relatively dissimilar to one another. Further, the injury severity classifier module 2708 can determine that the user is less likely to have experienced a severe injury if the user experienced impacts that are relatively similar to one another. The dissimilarity (or dissimilarity) between characteristics can be determined, for example, based on an arithmetic difference between the characteristics of the impacts and/or by determining a percentage of variation between the characteristics of the impacts. In some implementations, impacts may be similar to one another if the difference between their respective characteristics is less than a particular threshold value and/or the percentage of variation between their respective characteristics is less than a threshold percentage. In some implementations, impacts may be dissimilar to one another if the difference between their respective characteristics is greater than a particular threshold value and/or the percentage of variation between their respective characteristics is greater than a threshold percentage.

In some implementations, the injury severity classifier module 2708 can determine a severity of an injury suffered by the user based on one or more of these factors in combination.

As described herein, the system 100 can determine whether a user has fallen in a way that eliminates or otherwise reduces the occurrence of false positives (e.g., incorrect determinations that the user has fallen and/or is in need of assistance, when the user has not actually fallen and/or is not actually in need of assistance). In some implementations, these determinations can be made on a user specific basis. For instance, these determinations can be made for a particular user based on historical sensor data that had been previously collected regarding that user, historical information regarding that user's previous activities, the personal characteristics of the user (e.g., physical characteristics, age, demographic, etc.), and/or other information specific to the user.

In some implementations, the system 100 can generate and maintain a database of information that is specific to each user. The database includes one or more data records, each including information regarding an impact or "event" that was previously experienced by the user. As an example, a data record can include an indication of an impact that was previously experienced by the user (e.g., a unique identifier). Further, the data record can include sensor data collected by sensors worn on the user's body prior to, during, and/or after the impact (e.g., accelerometer data, gyroscope data, altimeter data, or any other sensor data). Further, the data record can include an indication of a type of activity that was being performed by the user at the time of the event (e.g., walking, running, swimming, playing a sport, riding a bicycle, etc.), as determined by an activity classifier module. Further, a data record can include metadata regarding the impact, such as the time when the impact occurred, the date when the impact occurred, the day of week when the impact occurred, and/or the location where the impact occurred. Further, the data record can include an indication whether the impact had been previously classified as a fall or not as a fall. This classification may be determined automatically (e.g., based on one or more of the techniques described herein) or manually by a user (e.g., based on input or feedback provided by the user after the impact).

The database can be used to determine user-specific characteristics that may be indicative of a fall. For example, the system 100 can cluster the data records with respect to one or more dimensions of information (e.g., time, day of week, sensor data, activity type, whether the user has fallen, etc.) into two or more clusters. At least one of the clusters can correspond to instances of the user previously experiencing an impact and falling. Further, at least one of the clusters can correspond to instances of the user previously experiencing an impact and not falling. In some implementations, data records can be clustered using a clustering technique such as K-means clustering.

The clustered data records can be used as "templates" to interpret newly collected sensor data to determine whether the user has fallen. For example, the system 100 can gather sensor data regarding the user has he goes about his daily life. When the user experiences an impact, the system 100 can collect information regarding the impact, such as sensor data collected from the user before, during, and/or after the impact, the time of day of the impact, the day of week or the impact, the geographic location of the impact, the type of activity that was being performed by the user, etc. Further, the system 100 can compare the collected information to the information contained in clustered data records. If the collected information is similar to the information in one of the clusters, the system 100 can determine whether the user has fallen based on whether the cluster corresponds to instances of the user falling or instances of the user not falling.

As an example, if the user regularly participates in a regularly scheduled contact sport (e.g., football), he may experience impacts according to a recurring schedule (e.g., during the same time of the day, same time of the week, etc.) and/or at the same geographical locations (e.g., in certain football fields). Further, the activity type of the user may be similar during each of those impacts (e.g., playing football), and the motion characteristics of the user may be similar during each of those impacts (e.g., corresponding to the user being tackled by others). Further, after those impacts, he may provide feedback to the system 100 that each of those impacts were associated with the sport, and where not falls in which he needed medical assistance. The system 100 can generate data records for these impacts or "events," then cluster them together into one or more clusters (e.g., based on their similarities in time, location, activity type, and sensor data). Further, system 100 can indicate that the one or more clusters are not associated with a fall.

In the future, the user may again play football according to his recurring schedule and typical location. During this time, the system 100 can collect sensor data to detect whether the user has experienced an impact (e.g., one or more of the techniques described herein). Upon detecting an impact, the system 100 can determine whether the characteristics of the impact (e.g., the time, location, activity type, and/or sensor data regarding the impact) are similar to those of the clustered data records. In this example, as the user is playing in a similar manner, at a similar time, and at a similar location. Accordingly, the system 100 can determine that the newly detected impact is similar to those in one or more clusters of data records that are not associated with a fall. In response, the system 100 can refrain from generating and transmitting a notification to others to assist the user.

After playing football, the user may return to his home and fall down a flight of stairs. During this time, the system 100 can collect sensor data to detect whether the user has experienced an impact. Upon detecting an impact, the system 100 can determine whether the characteristics of the impact are similar to those of the clustered data records. In this example, as the user is in a different location than those in the "not a fall" cluster of data records, has experienced an impact at a time of day that is different from his usual football schedule, was performing a different type of activity, and experienced an impact with motion characteristics different from those associated with playing football. Accordingly, the system 100 can determine that the newly detected impact is sufficiently different from those in one or more clusters of data records that are not associated with a fall. In response, the system 100 can generate and transmit a notification to others to assist the user.

In this manner, the system 100 can adapt its fall detection behavior based on the specific behavior and characteristics of the user of time. Further, the system 100 can continuously "learn" and improve its detection over time. For example, as the system 100 gathers more information regarding the user over the course of several impacts, the system 100 can update its database with new data records, and re-cluster the data records to find new associations and trends with respect to the collected information. Based on the re-clustered data records, the system 100 can determine whether new impacts experienced by the user are likely to be a fall.

In some implementations, the system 100 can discard, ignore, and/or give certain data records less weight based on their age. For example, if a data record is older than a particular threshold age, the system 100 can discard or ignore that data record, such that it is not included in the clusters (e.g., such that the impact associated with that impact is no longer considered). As another example, the system 100 can give that data record less weight in the cluster process (e.g., such that the impact associated with that impact has less influence in determining whether a user has fallen). This can be useful, for example, as it enables the system 100 to adapt to changes in the user's behavior over time.

As described above, in some implementations, a user can manually provide input or feedback regarding whether an impact was a fall (e.g., in which he needed medical assistance) or not a fall (e.g., in which he did not need medical assistance). As an example, after the system 100 has detected an impact, the system 100 can prompt the user to classify the impact as a fall or non-fall. The system 100 can include the user's input in the data record for that impact, and can use the input to cluster the data records in the database.

In some implementations, the system 100 can apply a user's input with respect to one impact to other impacts having similar characteristics. This may be beneficial, for example, in reducing the number of times that the system 100 asks the user for manual input. As an example, if a user experienced multiple similar impacts, the system 100 may cluster the data records associated with those impacts into a common cluster. If the user indicates that one of those impacts did not correspond to a fall, the system 100 can update each of the data records in that cluster to indicate that it is not associated with a fall. In this manner, the number of false positives can be reduced or eliminated, even if the user had previously erroneously indicated that other impacts within the same cluster had corresponded to falls.

In some implementations, the system 100 can cluster data records according to at multiple types of clusters according to the likelihood that each cluster corresponds to a fall. For example, the system 100 can cluster data records according to at least three clusters: "fall" clusters, "non-fall" clusters, and "near fall" clusters. The "fall" clusters are more likely to be associated with a fall (e.g., the information contained within them exhibit correlations or trends that more strongly distinguish from them "non-fall" clusters). The "near fall" clusters are less to be associated with a fall (e.g., the information contained within them exhibit correlations or trends that less strongly distinguish from them "non-fall" clusters). In some implementations, the likelihood that a cluster corresponds to fall can be express as a posterior ratio or probability.

When determining whether a newly detected impact corresponds to a fall, the system 100 can ignore the "near fall" clusters (e.g., clusters that only moderately likely to correspond to a fall), and only consider "fall" cluster (e.g., clusters that are much more likely to correspond to a fall) and "non-fall" clusters (e.g., clusters that are much less likely to correspond to a fall). This can be useful, for example, as the enables the system 100 to classify newly detected impacts based on "template" information that is more representative or indicative or falls and non-falls (rather than information that is only weakly correlated with one or the other, and may lead to ambiguous results). Thus, the system 100 can make classifications in a more accurate and/or predictable manner.

In some implementations, the database of information that is specific to a particular user can be maintained exclusively on the user's personal devices (e.g., his smart watch and/or smart phone, rather than a remote server). Further, the clustering and classification process can be performed exclusively on the user's personal devices. This can be useful, for example, in maintaining the privacy of the user. Nevertheless, in some implementations, at least some of the data of information can be maintained on one or more remote servers, either in addition to or instead of the user's personal devices. Similarly, in some implementations, at least a portion of the clustering and classification process can be performed on one or more remote servers, either in addition to or instead of the user's personal devices.

Figure 28:
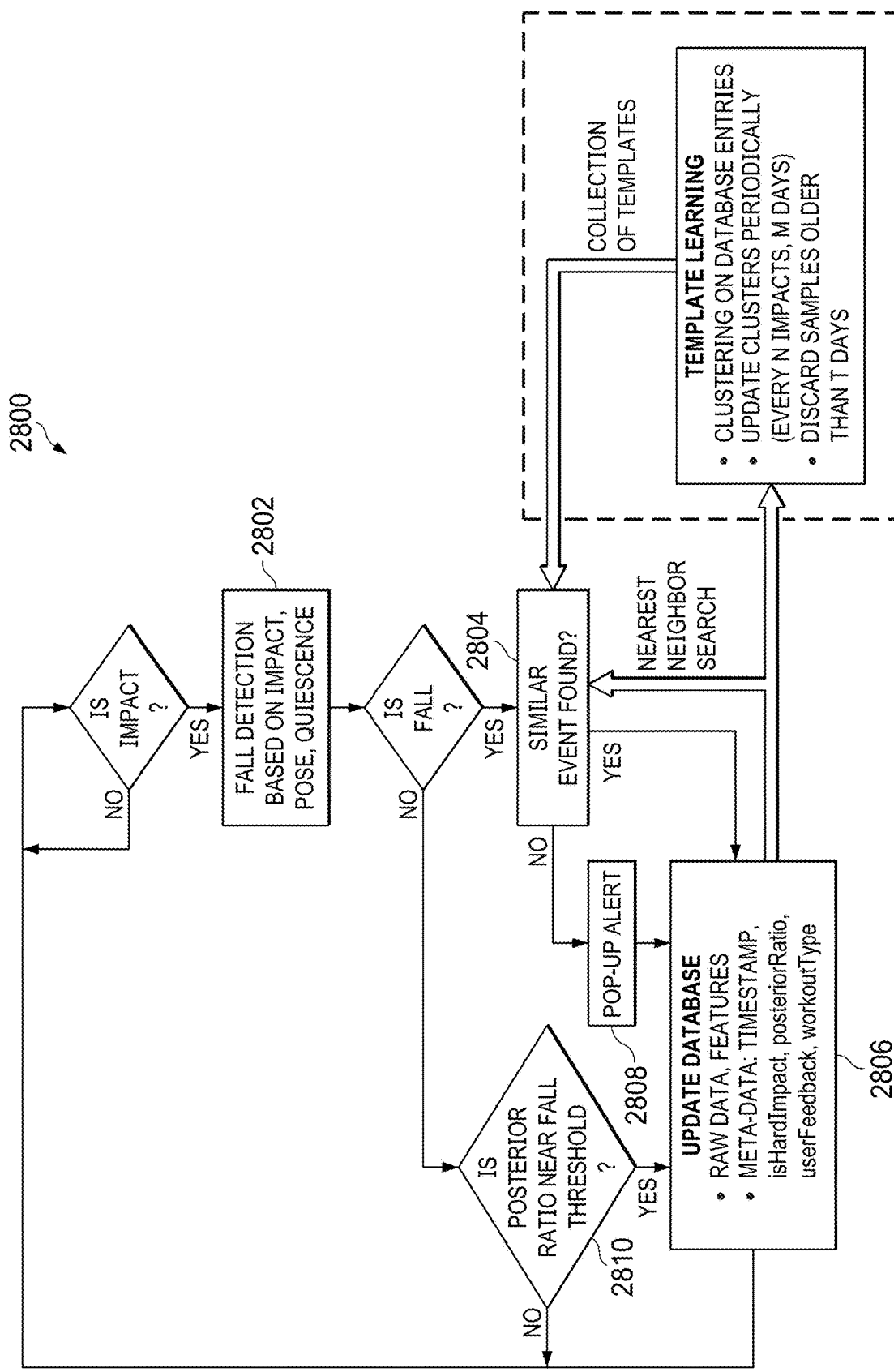
FIG. 28 is a flow chart diagram of an example process for making user-specific determinations whether a user has fallen.

An example process 2800 for making user-specific determinations whether a user has fallen is shown in FIG. 28. The process 2800 can be implemented, for example, one or more of the components of the system 100 shown in FIG. 1 (e.g., the mobile device 102).

According to the process 2800, a device (e.g., a mobile device 102) makes an initial determination whether a user has fallen based on sensor data obtained from sensors worn by the user on his body (step 2802). As examples, the device can obtain sensor data regarding an impact (e.g., acceleration data and/or jerk data), the pose angle or orientation of a device worn by the user and/or user, and/or the motion of the device and/or the user (e.g., whether the user is quiescent or active). Example techniques for determining whether a user has fallen based on sensor data are described herein.

In some implementations, the device can determine whether the user has fallen by calculating a probability metric (e.g., a posterior ratio). If the metric is higher than a first threshold value, the device can determine that the use has fallen. If the metric is lower than the first threshold value, the device can determine that the user has not fallen. In practice, the first threshold value can be selected empirically.

If the device determines that the user has fallen, the device determines if the detected fall is similar to a previously recorded event in a database (step 2804).

For example, if the newly detected fall has similar characteristics (e.g., similar time, day, activity type, sensor data, etc.) as those stored in one or more data records (or clusters of data records) in a database specific to the user, the device can determine that the newly detected fall is similar to one or more of the user's previously detected falls. In response, the device can update the database to include information regarding the newly detected fall (step 2806). For instance, the device can generate a data record for the newly detected fall, and include information regarding the fall. Example information includes sensor data collected by sensors worn on the user's body prior to, during, and/or after the impact, an indication of a type of activity that was being performed by the user at the time of the event, and metadata regarding the impact (e.g., the time when the fall occurred, the date when the fall occurred, the day of week when the fall occurred, and/or the location where the fall occurred). Further, the new data record can be clustered with the one or more data records to which it is similar (e.g., added to an existing cluster).

If the newly detected fall does not have similar characteristics as those stored in any of the data records in the database, the device can determine that the newly detected fall is not similar to one or more of the user's previously detected falls. In response, the device can generate an alert to a user (e.g., a pop up alert on a display device) asking the user for further input (step 2808). In response, the user can provide additional information regarding the fall. For example, the user can provide feedback regarding whether he had actually fallen, the type of activity that he was performing, or any other information regarding the event.

Similarly, the device can update the database to include information regarding the newly detected fall (step 2806). For instance, the device can generate a data record for the newly detected fall, and include information regarding the fall. Example information includes sensor data collected by sensors worn on the user's body prior to, during, and/or after the impact, an indication of a type of activity that was being performed by the user at the time of the event, and metadata regarding the impact (e.g., the time when the fall occurred, the date when the fall occurred, the day of week when the fall occurred, and/or the location where the fall occurred). Further, the new data record can include the information provided by the user (e.g., whether he had actually fallen, the type of activity that he was performing, or any other information regarding the event).

Referring back to step 2802, if the device instead determines that the user has not fallen, the device determines whether the probability metric associated with the newly detected event is near the threshold level (step 2804). As an example, the device can determine whether the probability metric associated with newly detected event is above a second threshold level that is less than the first threshold level. If the probability metric is lower than the second threshold value (e.g., it is not "near" the first threshold level for determining whether the user has fallen), the device can refrain from updating the database, and continue gathering sensor information regarding the user.

If the probability metric is greater than the second threshold level (e.g., it is "near" the first threshold level for determining whether user has fallen), the device can update the database to include information regarding the newly event (step 2806). For instance, the device can generate a data record for the newly detected event, and include information regarding the event. Example information includes sensor data collected by sensors worn on the user's body prior to, during, and/or after the event, an indication of a type of activity that was being performed by the user at the time of the event, and metadata regarding the event (e.g., the time when the event occurred, the date when the event occurred, the day of week when the event occurred, and/or the location where the event occurred).

During this process, the device can also update its database based on newly collection information to "learn" and improve its detection over time (step 2812). For example, the device can re-cluster the data records to find new associations and trends with respect to the collected information. In some implementations, the device can re-cluster the data records continuously over time. In some implementations, the device can re-cluster the data records periodically over time (e.g., every M days). In some implementations, the device can re-cluster the data records periodically based on the number of events that it has detected (e.g., every N detected events or impacts). Further, in some implementations, the device can discard data records base on their age (e.g., discard data records over than T days). In practice, each of M, N, and T can vary, depending on the implementation.

As described herein, the resulting database can be used to determine whether a user has fallen (e.g., in a manner that eliminates or otherwise reduces the occurrence of false positives).

In some implementations, the device can also identify false positives by measuring the impacts that the user experiences over a period of time, and identifying one or more patterns that may be indicative of a false positive.

For example, the device that determine, based on accelerometer measurements, that the user experienced multiple impacts over a period of time according to a periodic or approximately periodic sequence. For instance, the device may determine that the user experienced multiple impacts that recur according to a particular frequency, or recur according to a particular frequency within a particular tolerance range (e.g., ±5%, ±10%, ±15%, or some other tolerance range). In response, the device can determine that user is less likely to have experienced a fall. This could be useful, for example, in differentiating falls from repetitive physical activities (e.g., golfing, tennis, racquetball, badminton, batting in baseball or software, boxing, etc.). In some implementations, the period of time and/or the tolerance range can be selected empirically (e.g., based on experimental studies that identify differences between falls and other types of activities).

As another example, the device that determine, based on accelerometer measurements, that the user experienced multiple similar impacts over a period of time. For example, the device may determine that the user experienced multiple impacts having an intensity, a magnitude, and/or a power that are equal to one another or within a particular tolerance range of one another (e.g., ±5%, ±10%, ±15%, or some other tolerance range). In response, the device can determine that user is less likely to have experienced a fall. This could be useful, for example, in differentiating falls from repetitive physical activities (e.g., golfing, tennis, racquetball, badminton, batting in baseball or software, boxing, etc.). In some implementations, the period of time and/or the tolerance range can be selected empirically (e.g., based on experimental studies that identify differences between falls and other types of activities).

In some implementations, the device can also identify false positives by determining the smoothness of a user's movements over a period of time (e.g., leading up to the user experiencing an impact and/or after a user experiences in impact). For example, if the user's movements are relatively smooth over the period of time, the device can determine that the user is less likely to have experienced a fall. In contrast, if the user's movement are relatively less smooth over the period of time, the device can determine that the user is more likely to have experienced a fall. This could be useful, for example, in differentiating falls (e.g., which in some implementations may be characterized by relatively erratic movement) from physical activities that are characterized by relatively smooth movement. In some implementations, the period of time can be selected empirically (e.g., based on experimental studies that identify differences between falls and other types of activities).

The smoothness of a user's movements can be determined, for example, by obtaining accelerometer measurements as the user moves, and determining the intensity of changes in the acceleration measurements (e.g., "jerk") and/or the frequency of those changes. For instance, relatively smoother movement could correspond to less intense and/or less frequent changes in the acceleration measurements over a particular period of time, and relatively less smooth movement could correspond to more intense and/or more frequent changes in the acceleration measurements over a particular period of time.

In some implementations, the device can also identify false positives by determining the user's acceleration over a period of time with respect to multiple different directions or axes. Acceleration that is more intense with respect to one or more axes relative to one or more other axes may be less likely to be indicative of a fall. As an example, the device can obtain accelerometer measurements as the user moves, and determine the acceleration with respect to multiple different components according to an internal frame of reference. For instance, a first component can correspond to acceleration in a first direction parallel to the direction of gravity (a "vertical" direction), and a second component can correspond to acceleration in a second direction parallel to the direction of gravity (a "horizontal" direction). If the acceleration in the horizontal direction is sufficiently intense (e.g., greater than a first threshold level) and the acceleration in the vertical direction is sufficiently low (e.g., less than a second threshold level), the device can determine that user is less likely to have experienced a fall. This could be useful, for example, in differentiating falls (e.g., which in some implementations may be characterized by more intense acceleration in the vertical direction than in the horizontal direction) from physical activities in which the user experience acceleration that is predominantly in the horizontal direction rather than the vertical direction. In some implementations, the period of time, the first threshold value, and/or the second threshold value can be selected empirically (e.g., based on experimental studies that identify differences between falls and other types of activities).

Although the foregoing examples are described with respect to one mobile device at a time (e.g., the mobile device 102), in some implementations, multiple devices can be used in conjunction to perform the techniques described herein. As an example, multiple devices (e.g., a smart watch, a smartphone, and/or a remote server) can be communicatively coupled to one another (e.g., through one or more wireless communication links), and can exchange sensor data and/or other information gathered by each device. In some implementations, one device can collect sensor data, and provide the sensor data to another device for processing according to the techniques described herein. As an example, a smart watch can collect sensor data (e.g., as the smart watch may be more likely to be consistently positioned on a user's body than the smart phone), and provide the sensor data to a smart phone and/or a remote server for processing (e.g., as the smart phone and/or the remove server may have access to greater computation resources than the smart watch). In some implementations, multiple devices can collect sensor data concurrently, and provide the sensor data to other device for processing according to the techniques described. As an example, a smart watch and a smart phone can concurrently collect sensor data, and provide the sensor data to each other and/or a remote server for processing.

Example Processes

Figure 29:
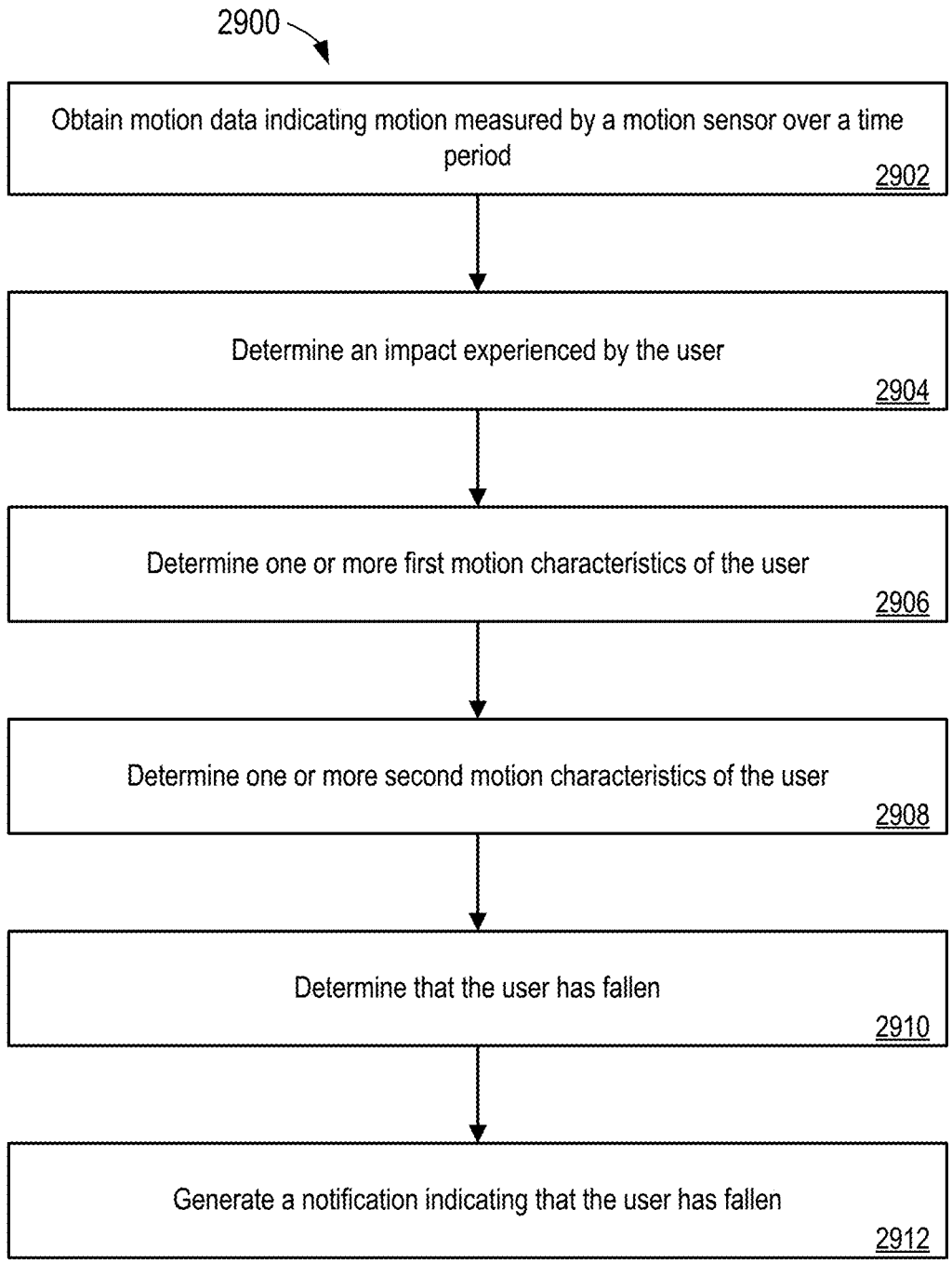
FIG. 29 is a flow chart diagram of an example process for determining whether a user has fallen and/or may be in need of assistance.

An example process 2900 for determining whether a user has fallen and/or may be in need of assistance using a mobile device is shown in FIG. 29. The process 2900 can be performed for example, one or more of the components of the system 100 shown in FIG. 1 (e.g., the mobile device 102). In some cases, some or all of the process 2900 can be performed by a co-processor of the mobile device. The co-processor can be configured to receive motion data obtained from one or more sensors, process the motion data, and provide the processed motion data to one or more processors of the mobile device.

In the process 2900, a mobile device (e.g., the mobile device 102 and/or one or more other components of the system 100) obtains motion data indicating motion measured by a motion sensor over a time period (step 2902). The sensor is worn by a user. As an example, as described with respect to FIGS. 1 and 2A, a user can attach a mobile device, such as a smart watch, to his arm or wrist, and goes about his daily life. This can include, for example, walking, running, sitting, laying down, participating in a sport or athletic activity, or any other physical activity. During this time, the mobile device uses a motion sensor in the mobile device (e.g., an accelerometer) to measure an acceleration experienced by the sensor over a period of time. Sensor data can be presented in the form of a time-varying acceleration signal (e.g., as shown in FIG. 3).

The mobile device determines an impact experienced by the user based on the motion data (step 2904), the impact occurring during a first interval of the time period. Example techniques for determining an impact are described above (e.g., with respect to FIGS. 3-5).

The mobile device determines, based on the motion data, one or more first motion characteristics of the user during a second interval of the time period (step 2906), the second interval occurring prior to the first interval. The second interval can be, for example, a "pre-impact" time period. Determining the first motion characteristics can include, for example, determining that the user was walking during the second interval, determining that the user was ascending or descending stairs during the second interval, and/or determining that the user was moving a body part according to a flailing motion or a bracing motion during the second interval. Example techniques for determining motion characteristics during the "pre-impact" time period are described above (e.g., with respect to FIG. 6).

The mobile device determines, on the motion data, one or more second motion characteristics of the user during a third interval of the time period (step 2908), the third interval occurring after the first interval. The third interval can be, for example, a "post-impact" time period. Determining the second motion characteristics can include, for example, determining that the user was walking during the third interval, determining that the user was standing during the third interval, and/or determining that an orientation of a body part of the user changed N or more times during the third interval. Example techniques for determining motion characteristics during the "pre-impact" time period are described above (e.g., with respect to FIGS. 7 and 8).

The mobile device determines that the user has fallen based on the impact, the one or more first motion characteristics of the user, and the one or more second motion characteristics of the user (step 2910). The mobile device can also determine that whether the user may be in need of assistance (e.g., as a result of the fall). Example techniques for determining whether a user has fallen and may be in need of assistance are described above (e.g., with respect to FIG. 9).

As an example, the mobile device can determine, based on the motion data, that the impact is greater than a first threshold value, and determining, based on the motion data, that a motion of the user was impaired during the third interval. Based on these determinations, the mobile device can determine that the user has fallen and may be in need of assistance.

As another example, the mobile device can determine, based on the motion data, that the impact is less than a first threshold value and greater than a second threshold value. Further, the mobile device can determine, based on the motion data, that the user was at least one of walking during the second interval, ascending stairs during the second interval, or descending stairs during the second interval. Further, the mobile device can determine, based on the motion data, that the user was moving a body part according to a flailing motion or a bracing motion during the second interval. Further, the mobile device can determine, based on the motion data, that a motion of the user was impaired during the third interval. Based on these determinations, the mobile device can determine that the user has fallen and may be in need of assistance.

In some cases, the mobile device can determine that the user has fallen based on a statistical model (e.g., a Bayesian statistical model). For example, a statistical model can be generated based on one or more sampled impacts, one or more sampled first motion characteristics, and one or more sampled second motion characteristics. The one or more sampled impacts, the one or more sampled first motion characteristics, and the one or more sampled second motion characteristics can be determined based on sample motion data collected from a sample population. The sample motion data can indicate motion measured by one or more additional motion sensors over one or more additional time periods, where each additional motion sensor is worn by a respective user of the sample population. Example techniques for generating and using statistical model are described above. In some implementations, the one or more sampled first motion characteristics can include an indication of a type of activity being performed by a particular additional user with respect to the sample motion data, an indication of an activity level of a particular additional user with respect to the sample motion data, and/or an indication of a walking speed of a particular additional user with respect to the sample motion data.

Responsive to determining that the user has fallen, the mobile device generates a notification indicating that the user has fallen (step 2912). As an example, the mobile device can present an indication that the user has fallen on a display device and/or an audio device of the mobile device. As another example, the mobile device can transmit data to a communications device remote from the mobile device indicating that the user has fallen. This can include, for example, an e-mail, instant chat message, text message, telephone message, fax message, radio message, audio message, video message, haptic message, or another message for conveying information. Example techniques for generating notifications are described above.

Figure 30:
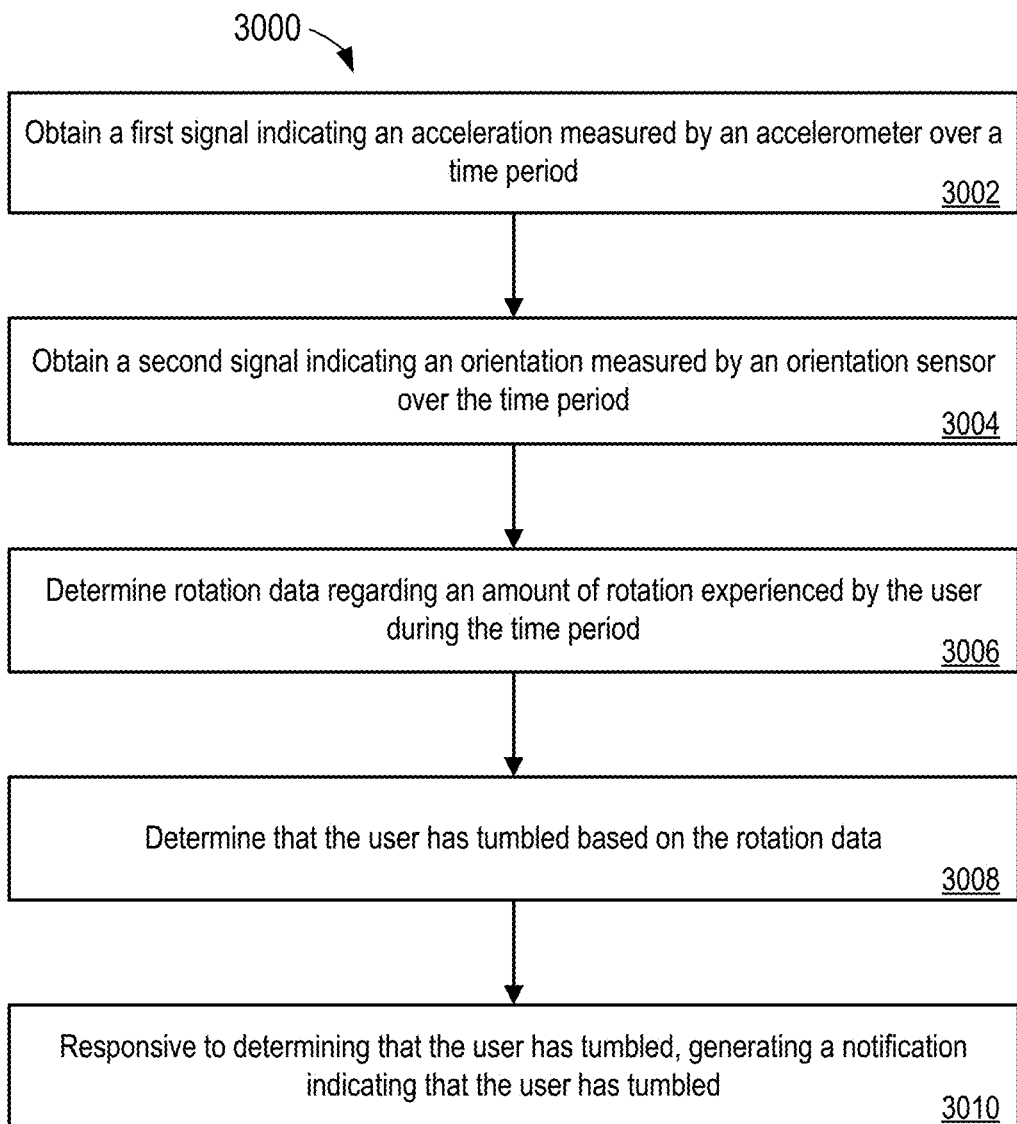
FIG. 30 is a flow chart diagram of an example process for determining whether a user has tumbled and/or may be in need of assistance.

Another example process 3000 for determining whether a user has fallen and/or may be in need of assistance using a mobile device is shown in FIG. 30. The process 3000 can be performed for example, using one or more of the components of the system 100 shown in FIG. 1 (e.g., the mobile device 102). In some cases, some or all of the process 3000 can be performed by a co-processor of the mobile device. The co-processor can be configured to receive motion data obtained from one or more sensors, process the motion data, and provide the processed motion data to one or more processors of the mobile device.

In the process 3000, a mobile device (e.g., the mobile device 102 and/or one or more other components of the system 100) obtains a first signal indicating an acceleration measured by an accelerometer over a time period (step 3002), and a second signal indicating an orientation measured by an orientation sensor over the time period (step 3004). The accelerometer and the orientation sensor are physically coupled to a user. As an example, as described with respect to FIGS. 1 and 2A, a user can attach a mobile device, such as a smart watch, to his arm or wrist, and goes about his daily life. This can include, for example, walking, running, sitting, laying down, participating in a sport or athletic activity, or any other physical activity. During this time, the mobile device uses sensors in the mobile device (e.g., an accelerometer and orientation sensor, such as a gyroscope) to measure an acceleration experienced by the sensors over a period of time and an orientation of the sensors over the period of time. Sensor data can be presented in the form of a time-varying signal (e.g., as shown in FIG. 11A).

The mobile device determines rotation data regarding an amount of rotation experienced by the user during the time period (step 3006). The rotational data can include a third signal corresponding to a rotation rate of the rotation by the user during the time period, an indication of one or more rotational axes of the rotation in a reference coordinate system by the user during the time period (e.g., one or more instantaneous axes of rotation), and/or an indication of an average rotational axis of the rotation by the user during the time period. Examples rotational data is shown and described, for instance, in FIGS. 11A-11D.

The mobile device determines that the user has tumbled based on the rotation data (step 3008). In some cases, this can be performed by determining a variation between the one or more rotational axes of the rotation by the user during the time period and the average rotational axis of the rotation by the user during the time period. Further, the mobile device can determine that the variation is less than a first threshold value. Responsive to determining that the variation is less than the first threshold value, the mobile device can determine a fourth signal corresponding to an angular displacement by the user during the time period based on the third signal (e.g., by integrating the third signal with respect to the period of time).

Further, the mobile device can determine that the angular displacement by the user during the period of time is greater than a second threshold value, and determine that at least one of the one or more rotational axes of the rotation by the user during the period of time is greater than a third threshold value. Responsive to determining that the angular displacement by the user during the period of time is greater than the second threshold value and determining that at least one of the one or more rotational axes of the rotation by the user during the period of time is greater than the third threshold value, the mobile device can determine that the user has tumbled. Otherwise, the mobile device can determine that the user has not tumbled.

Responsive to determining that the user has tumbled, the mobile device generates a notification indicating that the user has tumbled (step 3010). Generating the notification can include presenting an indication that the user has tumbled on at least one of a display device or an audio device of the mobile device and/or transmitting data to a communications device remote from the mobile device. This can include, for example, an e-mail, instant chat message, text message, telephone message, fax message, radio message, audio message, video message, haptic message, or another message for conveying information. The data can include an indication that the user has tumbled. Example techniques for generating notifications are described above.

Figure 31:
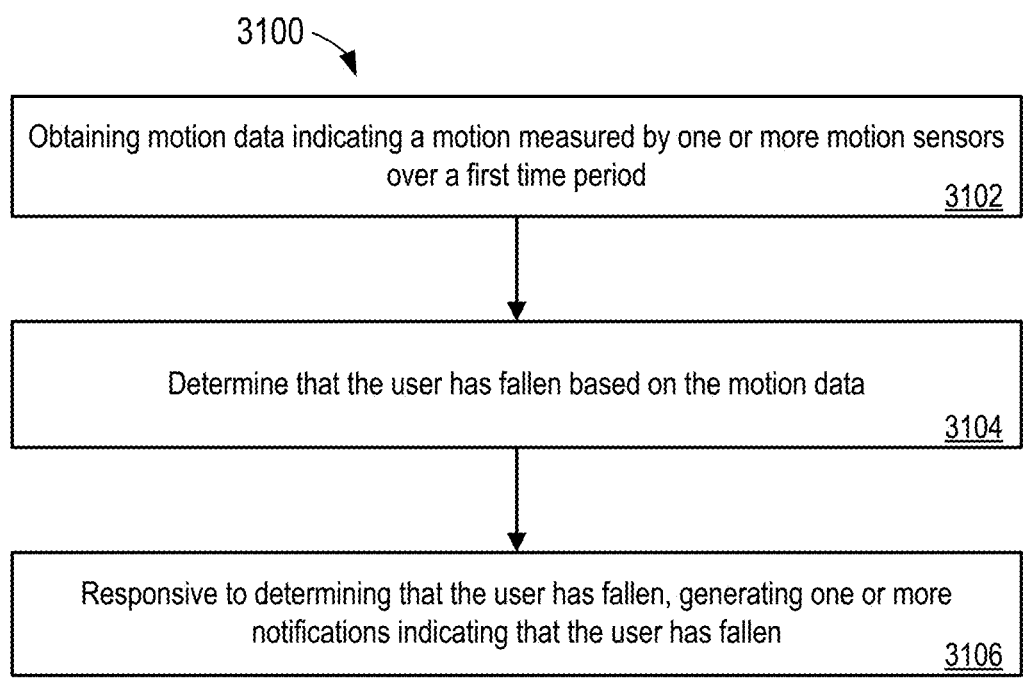
FIG. 31 is a flow chart diagram of an example process for determining whether a user has fallen and/or may be in need of assistance.

Another example process 3100 for determining whether a user has fallen and/or may be in need of assistance using a mobile device is shown in FIG. 31. The process 3100 can be performed for example, using one or more of the components of the system 100 shown in FIG. 1 (e.g., the mobile device 102). In some cases, some or all of the process 3100 can be performed by a co-processor of the mobile device. The co-processor can be configured to receive motion data obtained from one or more sensors, process the motion data, and provide the processed motion data to one or more processors of the mobile device.

In the process 3100, a mobile device (e.g., the mobile device 102 and/or one or more other components of the system 100) obtains motion data indicating a motion measured by one or more motion sensors over a first time period (step 3102). The one or more motion sensors are worn by a user. The one or more motion sensors can include an accelerometer and/or a gyroscope. The mobile device can be a wearable mobile device. Example techniques for obtaining motion data are described above.

The mobile device determines that the user has fallen based on the motion data (step 3104). In some implementations, the mobile device can determine that the user has fallen by determining that the user experienced an impact based on the motion data). In some implementations, the mobile device can determine that the user has fallen by determining a behavior of the user during the first time period. Example techniques for determining whether a user has fallen are described above.

Responsive to determining that the user has fallen, the mobile device generates one or more notifications indicating that the user has fallen (step 3106). In some implementations, generating the one or more notifications can include presenting a first notification to the user indicating that the user has fallen. The first notification can include at least one of a visual message, an audio message, or a haptic message. Example techniques for generating notifications are described above.

In some implementations, the mobile device can receive an input from the user in response to the first notification (e.g., an input indicating a request for assistance by the user). In response to receiving the input, the mobile device can transmit a second notification indicating the request for assistance to a communications device remote from the mobile device. The communications device can be an emergency response system. Further, the second notification can indicate a location of the mobile device.

In some implementations, the mobile device can determine an absence of movement by the user during a second time period after the user has fallen (e.g., indicating that the user is injured or incapacitated). Responsive to determining the absence of movement by the user during the second time period, the mobile device can transmit a second notification indicating a request for assistance to a communications device remote from the mobile device.

In some implementations, the mobile device can determine that the user has moved during a second time period after the user has fallen (e.g., walked, stood up, or perhaps some other type of movement). Responsive to determining that the user has moved during the second time period, the mobile device can refrain from transmitting a second notification indicating a request for assistance to a communications device remote from the mobile device.

In some implementations, the one or more notifications can be generated according to a state machine. Example state machines are shown in FIGS. 12 and 20.

Figure 32:
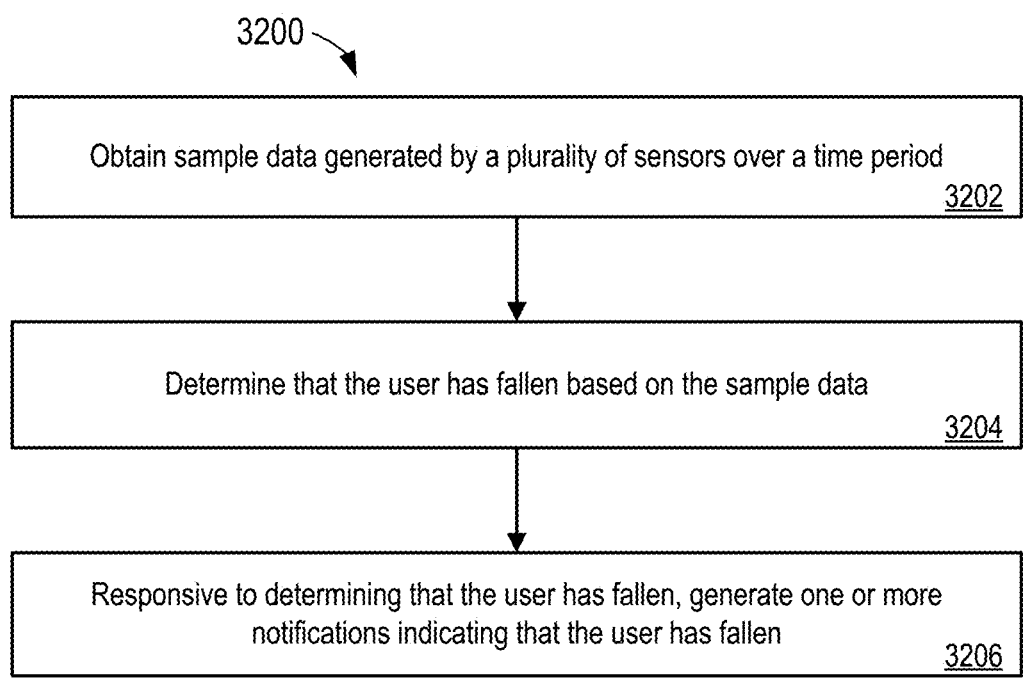
FIG. 32 is a flow chart diagram of an example process for determining whether a user has fallen and/or may be in need of assistance.

Another example process 3200 for determining whether a user has fallen and/or may be in need of assistance using a mobile device is shown in FIG. 32. The process 3200 can be performed for example, as one or more of the components of the system 100 shown in FIG. 1 (e.g., the mobile device 102). In some cases, some or all of the process 3200 can be performed by a co-processor of the mobile device. The co-processor can be configured to receive motion data obtained from one or more sensors, process the motion data, and provide the processed motion data to one or more processors of the mobile device.

In the process 3200, a mobile device (e.g., the mobile device 102 and/or one or more other components of the system 100) obtains sample data generated by a plurality of sensors over a time period (step 3202). The plurality of sensors is worn by a user. The sample data includes motion data indicating a motion of the user obtained from one or more motion sensors of the plurality of sensors. The sample data also includes at least one of location data indicating a location of the mobile device obtained from one or more location sensors of the plurality of sensors, altitude data indicating an altitude of the mobile device obtained from one or more altitude sensors of the plurality of sensors, or heart rate data indicating a heart rate of the user obtained from one or more heart rate sensor of the plurality of sensors. The mobile device can be a wearable mobile device. Example techniques for obtaining sample data are described above.

In some implementations, the one or more motion sensors can include an accelerometer and/or a gyroscope. In some implementations, an accelerometer and a gyroscope can be independently operated to acquire motion data. For example, acceleration data can be obtained using the accelerometer during a first time interval during the period of time. The gyroscope can be disabled during the first time interval. Further, based on the acceleration data obtained during the first time interval, the mobile device can determine that a movement of a user exceeded a threshold level during the first time interval. Responsive to determining that the movement of the user exceeded the threshold level during the first time interval, the mobile device can obtain acceleration data using the accelerometer and gyroscope data using the gyroscope during a second time interval after the first time interval. In some cases, the accelerometer and the gyroscope can be operated according to a state machine. An example state machine is shown in FIG. 14.

In some implementations, the one or more altitude sensors can include at least one of an altimeter or a barometer. The altitude sensors can be used, for example, to measure certain changes in altitude indicate of a fall (e.g., a decrease in altitude indicative of falling off a ladder or structure).

In some implementations, the one or more location sensors can include at least one of a wireless transceiver (e.g., a Wi-Fi radio or cellular radio) or a global Navigation Satellite System receiver (e.g., a GPS receiver).

The mobile devices determines that the user has fallen based on the sample data (step 3204). Example techniques for determining whether a user has fallen are described above.

In some implementations, the mobile device can determine that the user has fallen by determining, based on the motion data, a change in orientation of the mobile device (e.g., a pose angle) during the period of time, and determining that the user has fallen based on the change in orientation.

In some implementations, the mobile device can determine that the user has fallen by determining, based on the motion data, an impact experienced by the user during the period of time, and determining that the user has fallen based on the impact.

In some implementations, the mobile device can determine that the user has fallen by determining, based on the altitude data, a change in altitude of the mobile device during the period of time, and determining that the user has fallen based on the change in altitude.

In some implementations, the mobile device can determine that the user has fallen by determining, based on the heart rate data, a change in heart rate of the user during the period of time, and determining that the user has fallen based on the change in heart rate. Determining the change in heart rate of the user during the period of time cab include determining a rate of decay of the heart rate of the user during the period of time (e.g., a time constant associated with the rate of decay).

In some implementations, the mobile device can determine that the user has fallen by determining, based on the location data, an environmental condition at the location of the mobile device, and determining that the user has fallen based on the environment conditional. The environmental condition can be a weather at the location (e.g., rain, snow, etc.).

In some implementations, the mobile device can determine that the user has fallen based on the motion data, the location data, the altitude data, and the heart rate data (e.g., in conjunction).

Responsive to determining that the user has fallen, the mobile device generates one or more notifications indicating that the user has fallen (step 3206). Generating the one or more notifications can include transmitting a notification to a communications device remote from the mobile device. The communications device can be emergency response system. Example techniques for generating notifications are described above.

Figure 33:
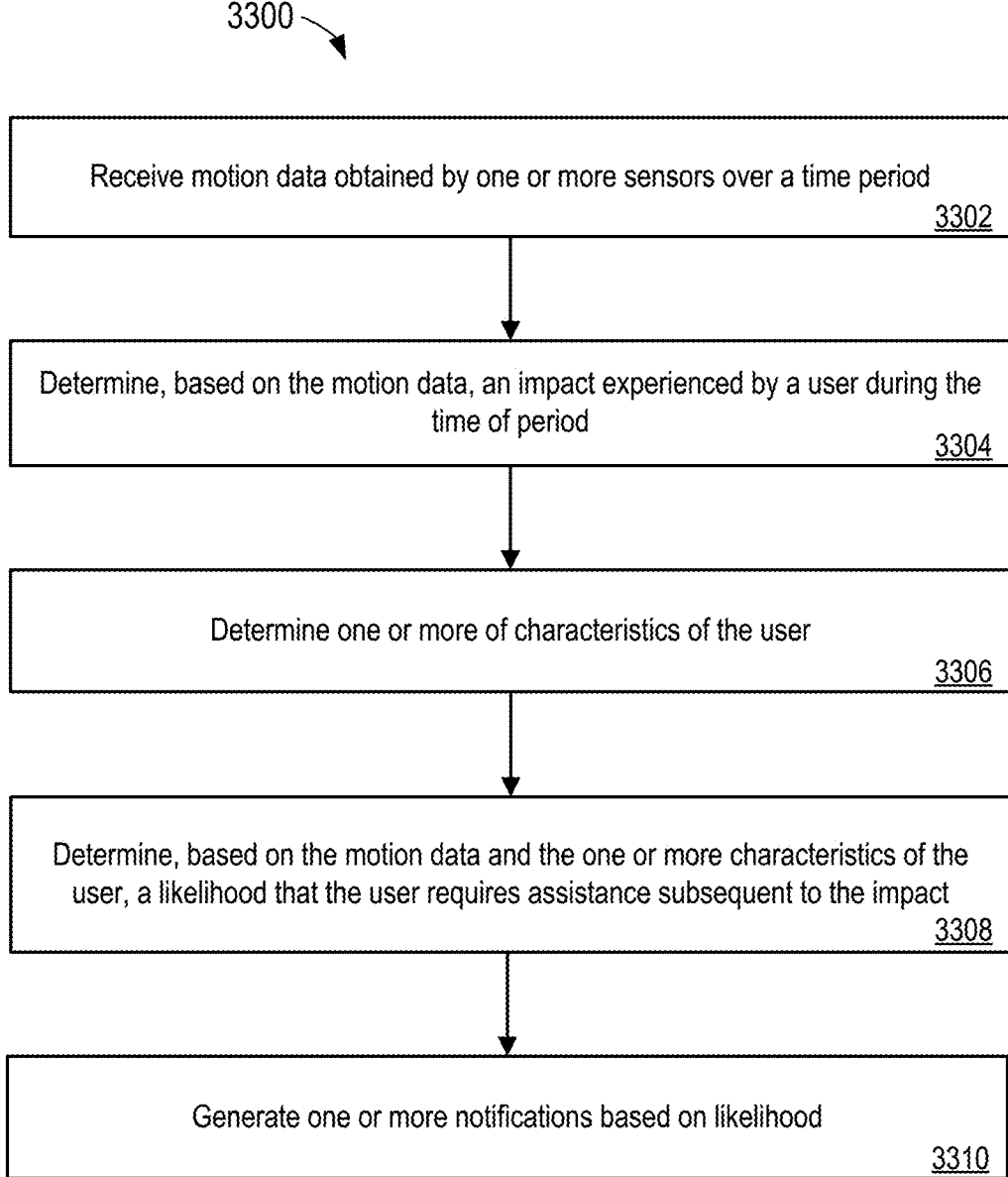
FIG. 33 is a flow chart diagram of an example process for determining whether a user has fallen and/or may be in need of assistance.

Another example process 3300 for determining whether a user has fallen and/or may be in need of assistance using a mobile device is shown in FIG. 33. The process 3300 can be performed for example, as one or more of the components of the system 100 shown in FIG. 1 (e.g., the mobile device 102). In some cases, some or all of the process 3300 can be performed by a co-processor of the mobile device. The co-processor can be configured to receive motion data obtained from one or more sensors, process the motion data, and provide the processed motion data to one or more processors of the mobile device.

In the process 3300, a mobile device (e.g., the mobile device 102 and/or one or more other components of the system 100) receives motion data obtained by one or more sensors over a time period (step 3302). The one or more sensors are worn by a user. In some implementations, the one or more sensors can include one or more accelerometers, gyroscopes, and/or altimeters or barometers.

The mobile device determines, based on the motion data, an impact experienced by the user during the time of period (step 3304).

The mobile device determines one or more of characteristics of the user (step 3306).

The mobile device determines, based on the motion data and the one or more characteristics of the user, a likelihood that the user requires assistance subsequent to the impact (step 3308).

In some implementations, the one or more characteristics of the user can include an age of the user. Further, the likelihood can increase with an increase in the age of the user.

In some implementations, the one or more characteristics of the user can include a gender of the user. Further, the likelihood can depend on the gender of the user.

In some implementations, the one or more characteristics of the user can include a historical physical activity level of the user. Further, the likelihood can increase with a decrease in the historical physical activity level of the user. In some implementations, the historical physical activity level can be indicative of a frequency of movement by the user prior to the impact. In some implementations, the historical physical activity level can be indicative of an intensity of movement by the user prior to the impact.

In some implementations, the one or more characteristics of the user can include a vascular health of the user. Further, the likelihood can increase with a decrease in the vascular health of the user. The vascular health of the user can be determined based on a maximal oxygen uptake ($VO_2$ max) of the user.

In some implementations, the one or more characteristics of the user can include a historical walking speed of the user. The likelihood can increase with a decrease in the historical walking speed of a user.

The mobile device generates one or more notifications based on likelihood (step 3310).

In some implementations, generating the one or more notifications can include determining that the likelihood exceeds a threshold level, and responsive to determining that the likelihood exceeds the threshold level, generating the one or more notifications.

In some implementations, generating the one or more notifications can include transmitting a first notification to a communications device remote from the mobile device. The first notification can include an indication that the user has fallen. The communications device can be an emergency response system.

In some implementations, the mobile device is a wearable mobile device (e.g., a smart watch). In some implementations, at least some of the one or more sensors can be disposed on or in the mobile device. In some implementations, at least some of the one or more sensors can be remote from the mobile device.

Additional details regarding the process 3300 are described above (e.g., with respect to FIG. 23)

Figure 34:
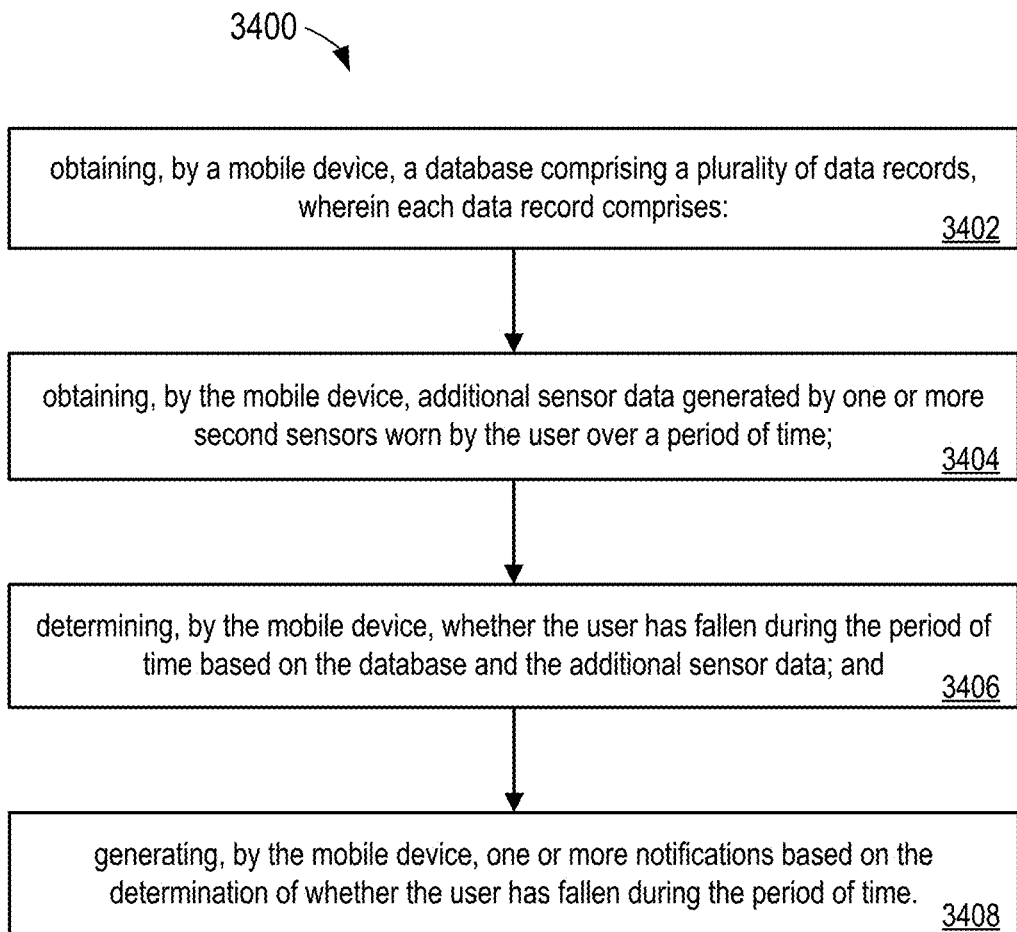
FIG. 34 is a flow chart diagram of an example process for determining whether a user has fallen and/or may be in need of assistance.

Another example process 3400 for determining whether a user has fallen and/or may be in need of assistance using a mobile device is shown in FIG. 34. The process 3400 can be performed for example, as one or more of the components of the system 100 shown in FIG. 1 (e.g., the mobile device 102). In some cases, some or all of the process 3400 can be performed by a co-processor of the mobile device. The co-processor can be configured to receive motion data obtained from one or more sensors, process the motion data, and provide the processed motion data to one or more processors of the mobile device.

In the process 3400, a mobile device (e.g., the mobile device 102 and/or one or more other components of the system 100) obtains a database including several data records (step 3402). Each data record includes an indication of a respective impact previously experienced by a user of the mobile device, and sensor data generated by one or more first sensors worn by the user during that impact. In some implementations, the one or more first sensors can include one or more accelerometers, gyroscopes, and/or altimeters or barometers.

The mobile device obtains additional sensor data generated by one or more second sensors worn by the user over a period of time (step 3404).

In some implementations, the one or more first sensors and the one or more second sensors can include at least one of an accelerometer or an orientation sensor. Further, for each data record, the sensor data can include one or more first signals indicating an acceleration measured by the accelerometer during the impact associated with the data record, and one or more second signals indicating an orientation measured by the orientation sensor during the impact associated with the data record.

In some implementations, the additional sensor data can include one or more additional first signals indicating an acceleration measured by the accelerometer during the period of time, and one or more additional second signals indicating an orientation measured by the orientation sensor during the period of time.

In some implementations, each data record can include metadata regarding the impact associated with the data record. The metadata can include at least one of an indication of a respective time of the impact associated with the data record, or an indication of a respective day of the week of the impact associated with the data record.

The mobile device determines whether the user has fallen during the period of time based on the database and the additional sensor data (step 3406).

In some implementations, determining whether the user has fallen can include determining, based on the additional sensor data, that the user has experienced an impact. Further, in response to determining that the user has experienced the impact, a likelihood that the impact corresponds to the user falling can be determined based on the additional sensor data, In some implementations, determining whether the user has fallen can include determining that the user has fallen based on the determined likelihood. Further, in response to determining that the user has fallen, a similarity metric can be determined. The similarity metric can indicate a similarity between the additional sensor data and the sensor data of one or more clusters of the plurality of data records.

In some implementations, determining whether the user has fallen can include determining, based on the additional sensor data, that the user experienced multiple impacts during the period of time, and determining, based on the additional sensor data, that the multiple impacts are similar to one another. In response to these determinations, a determination can be made that the user is less likely to have fallen during the period of time.

In some implementations, determining whether the user has fallen can include determining, based on the additional sensor data, that the user experienced multiple impacts a periodic sequence during the period of time, and in response, determining that the user is less likely to have fallen during the period of time.

In some implementations, determining whether the user has fallen can include determining, based on the additional sensor data, a smoothness of a movement of the user during the period of time, and determining whether the user has fallen during the period of time based on the smoothness of the movement of the user.

In some implementations, determining whether the user has fallen can include determining, based on the additional sensor data, an acceleration of the user during the period of time with respect to a first direction and a second direction orthogonal to the first direction, and determining that the acceleration in the first direction is greater than a first threshold value and that the acceleration in the second direction is less than a second threshold value. In response to these determinations, a determination can be made that the user is less likely to have fallen during the period of time. In some implementations, the first direction can be orthogonal to a direction of gravity, and the second direction can be parallel to the direction of gravity.

The mobile device generates one or more notifications based on the determination of whether the user has fallen during the period of time (step 3408).

In some implementations, generating the one or more notifications can include determining that the similarity metric is less than a threshold level, and in response, generating a first notification to the user to confirm whether the user has fallen.

In some implementations, generating the one or more notifications can include receiving, from the user, an input indicating that the user has fallen, and in response, transmitting a second notification to a communications device remote from the mobile device. The second notification can include an indication that the user has fallen. In some implementations, the communications device can be an emergency response system.

In some implementations, the process 3400 can also include generating an additional data record based the additional sensor data, and including the additional data record in the database.

In some implementations, the database can be stored on a storage device of the mobile device.

In some implementations, the process 3400 can also include generating, by the mobile device, one or more clusters of the data records based on similarities between the data records. The one or more clusters can be generated using k-means clustering.

In some implementations, at least some of the one or more first sensors or the one or more second sensors can be disposed on or in the mobile device.

In some implementations, at least some of the one or more first sensors or the one or more second sensors can be remote from the mobile device.

In some implementations, at least some of the one or more first sensors can be the same as at least some of the one or more second sensors.

Additional details regarding the process 3400 are described above (e.g., with respect to FIG. 28).

Figure 35:
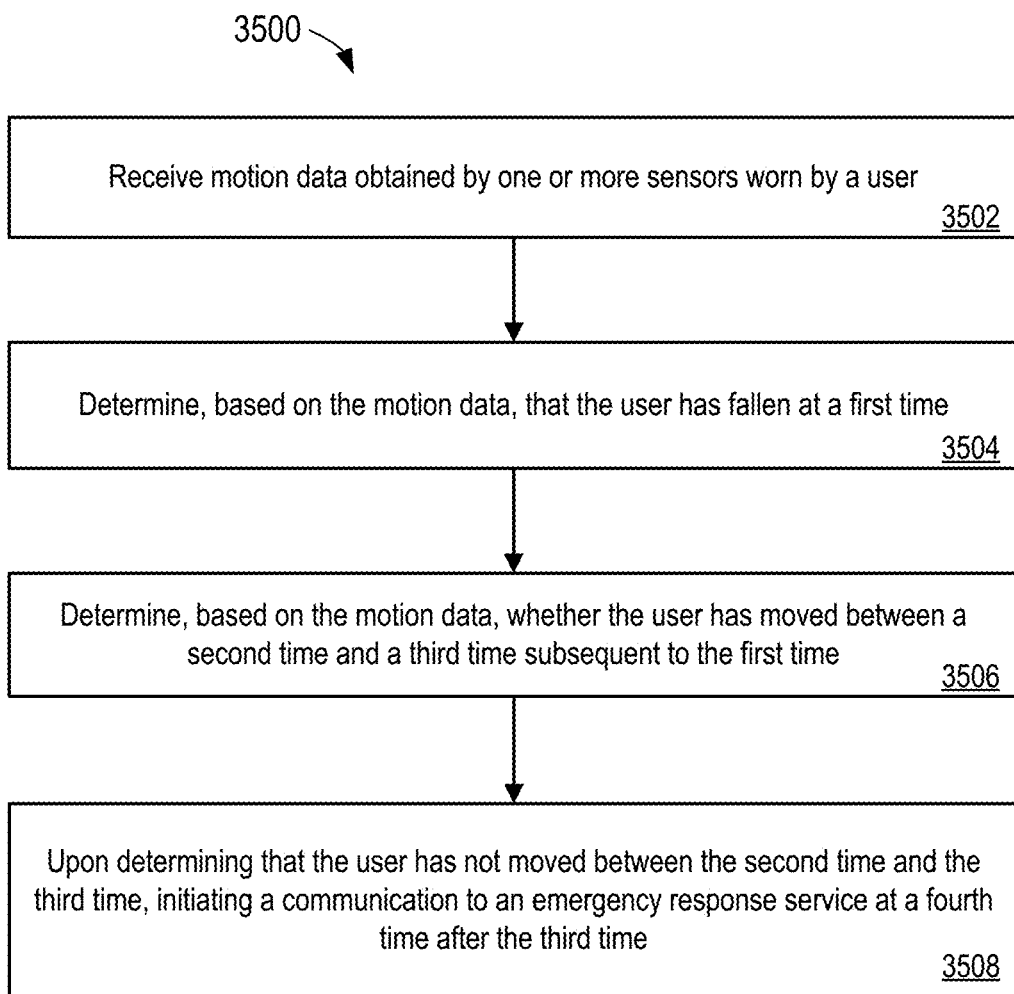
FIG. 35 is a flow chart diagram of an example process for determining whether a user has fallen and/or may be in need of assistance.

Another example process 3500 for determining whether a user has fallen and/or may be in need of assistance using a mobile device is shown in FIG. 35. The process 3500 can be performed for example, as one or more of the components of the system 100 shown in FIG. 1 (e.g., the mobile device 102). In some cases, some or all of the process 3500 can be performed by a co-processor of the mobile device. The co-processor can be configured to receive motion data obtained from one or more sensors, process the motion data, and provide the processed motion data to one or more processors of the mobile device.

In the process 3500, a mobile device (e.g., the mobile device 102 and/or one or more other components of the system 100) receives motion data obtained by one or more sensors (step 3502). The one or more sensors are worn by a user.

The mobile device determines, based on the motion data, that the user has fallen at a first time (step 3504).

The mobile device determines, based on the motion data, whether the user has moved between a second time and a third time subsequent to the first time (step 3506).

In some implementations, the one or more sensors can include one or more accelerometers. Further, the motion data can include one or more acceleration signals obtained by the one or more accelerometers. Further, determining whether the user has moved between the first time and the second time can include determining a change in the one or more acceleration signals between the first time and the second time.

In some implementations, the one or more sensors can include one or more orientation sensors. Further, the motion data can include one or more orientation signals obtained by the one or more orientation sensors. Further, determining whether the user has moved between the first time and the second time can include determining a change in the one or more orientation signals between the first time and the second time.

In some implementations, determining whether the user has moved between the second time and the third time can include determining whether the user is walking between the second time and the third time.

In some implementations, determining whether the user has moved between the second time and the third time can include determining whether the user stood up between the second time and the third time.

Upon determining that the user has not moved between the second time and the third time, the mobile device initiates a communication to an emergency response service at a fourth time after the third time (step 3508). The communication includes an indication that the user has fallen and a location of the user.

In some implementations, upon determining that the user has moved between the second time and the third time, the mobile device can refrain from initiating the communication to the emergency response service.

In some implementations, subsequent to initiating the communication to the emergency response service, the mobile device can receive a command to terminate the communication from the user. In response, the mobile device can terminate the communication.

In some implementations, the mobile device can be a wearable mobile device. In some implementations, at least some of the one or more sensors can be disposed on or in the mobile device. In some implementations, at least some of the one or more sensors can be remote from the mobile device.

Additional details regarding the process 3500 are described above (e.g., with respect to FIG. 26).

Figure 36:
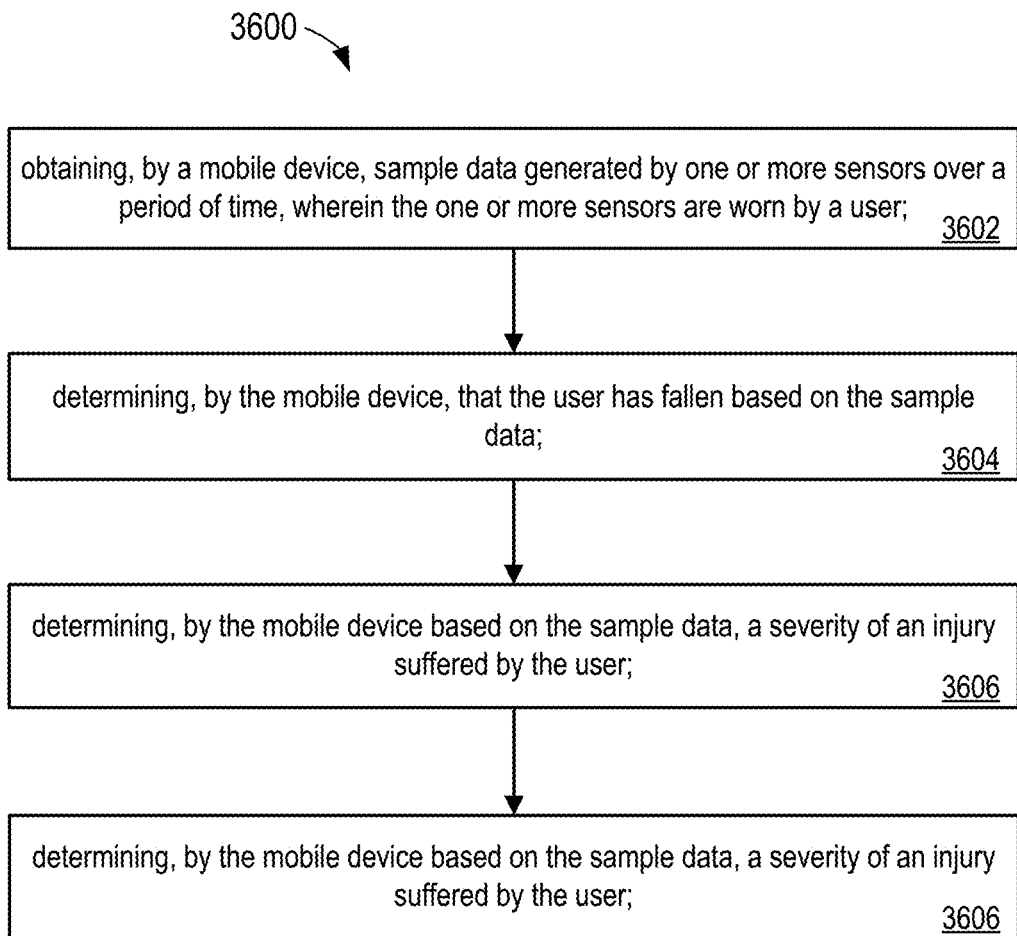
FIG. 36 is a flow chart diagram of an example process for determining whether a user has fallen and/or may be in need of assistance.

Another example process 3600 for determining whether a user has fallen and/or may be in need of assistance using a mobile device is shown in FIG. 36. The process 3600 can be performed for example, as one or more of the components of the system 100 shown in FIG. 1 (e.g., the mobile device 102). In some cases, some or all of the process 3600 can be performed by a co-processor of the mobile device. The co-processor can be configured to receive motion data obtained from one or more sensors, process the motion data, and provide the processed motion data to one or more processors of the mobile device.

In the process 3600, a mobile device (e.g., the mobile device 102 and/or one or more other components of the system 100) obtains sample data generated by one or more sensors over a period of time (step 3602). The one or more sensors are worn by a user.

The mobile device determines that the user has fallen based on the sample data (step 3604).

The mobile device determines, based on the sample data, a severity of an injury suffered by the user (step 3606).

The mobile device generates one or more notifications based on the determination that the user has fallen and the determined severity of the injury (step 3608). In some implementations, generating the one or more notifications can include transmitting a first notification to a communications device remote from the mobile device. The first notification can include an indication that the user has fallen and an indication of the determined severity of the injury suffered by the user. The communications device can be an emergency response system.

In some implementations, the one or more sensors can include at least one of an accelerometer, an orientation sensor, or an altimeter. Further, the sample data can include motion data indicating a motion of the user over the period of time. Further, determining that the user has fallen can include determining, based on the motion data, a first impact experienced by the user during the period of time, and determining, based on the motion data, a change in orientation of a portion of the user's body during the period of time. The portion of the user's body can be (or can include) the user's wrist.

In some implementations, the motion data can include a first signal indicating an acceleration measured by the accelerometer over the period of time, and a second signal indicating an orientation measured by the orientation sensor over the period of time. Further, determining the severity of the injury suffered by the user can include determining, based on the first signal and the second signal, a severity of the first impact experienced by the user.

In some implementations, determining the severity of the injury suffered by the user can include determining, based on the first signal and the second signal, that the user experienced multiple impacts including the first impact during the period of time.

In some implementations, the severity of the injury suffered by the user can be determined based on a similarity between impacts experienced by a user. For example, a first set of characteristics associated with the first impact can be determined based on the first signal and the second signal. Further, a second set of characteristics associated with a second impact experienced by the user during the period of time can be determined based on the first signal and the second signal. Further, a similarity between the first set of characteristics and the second set of characteristics can be determined. In some implementations, a greater degree of similarity between the characteristics of the first and second impacts can correspond to a lesser severity of injury. In some implementations, a lesser degree of similarity between the characteristics of the first and second impacts can correspond to a greater severity of injury.

In some implementations, the motion data can include a third signal indicating an altitude measured by the altimeter over the period of time. Determining the severity of the injury suffered by the user further can include determining, based on the third signal, a distance fallen by the user over the period of time. The severity of the injury can be determined based on the determined severity of the impact experienced by user and the determined distance fallen by the user.

In some implementations, the mobile device can be a wearable mobile device. In some implementations, at least some of the one or more sensors can be disposed on or in the mobile device. In some implementations, at least some of the one or more sensors can be remote from the mobile device.

Additional details regarding the process 3500 are described above (e.g., with respect to FIG. 27).

Example Mobile Device

Figure 37:
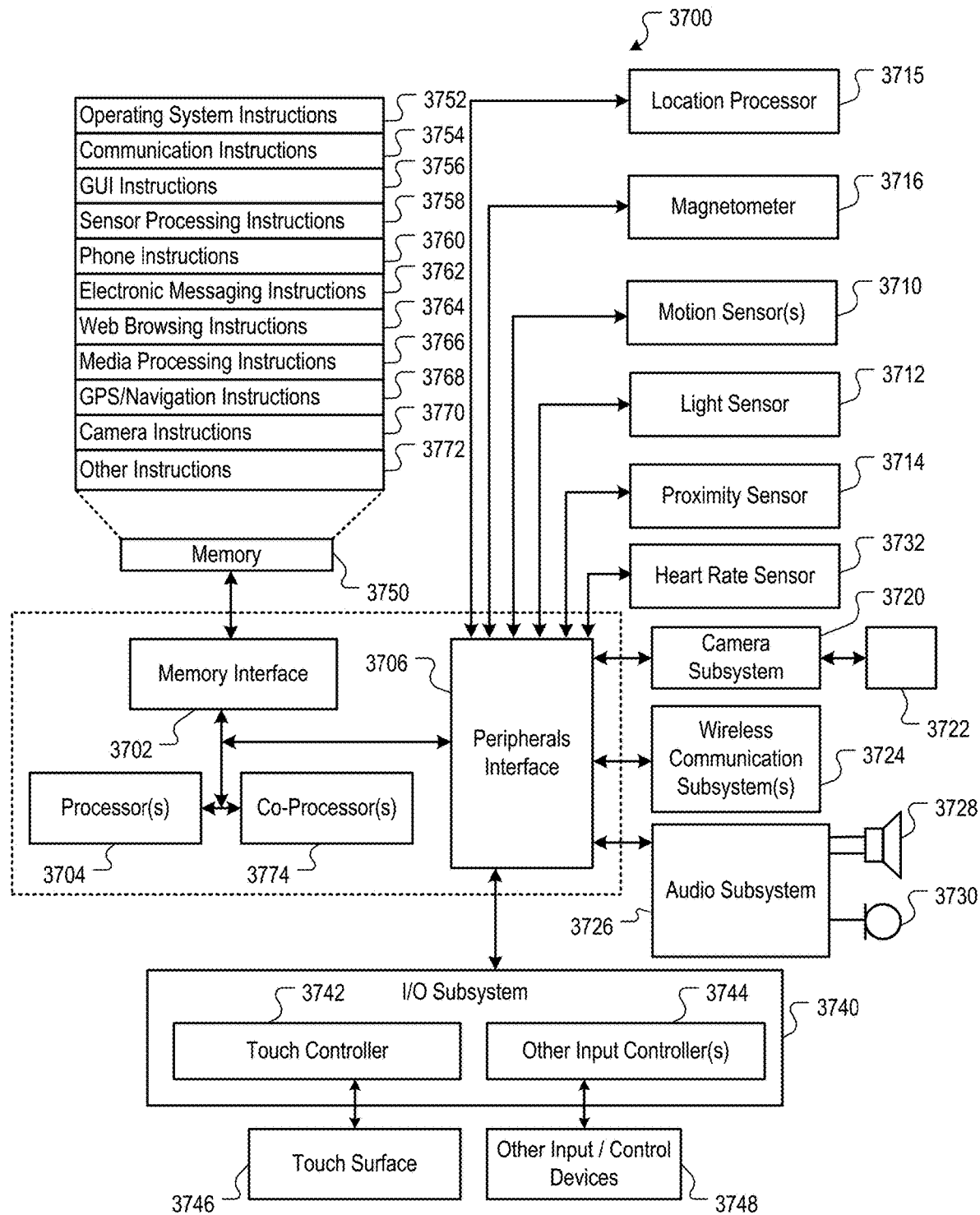
FIG. 37 is a block diagram of an example architecture for implementing the features and processes described in reference to FIGS. 1-36.

FIG. 37 is a block diagram of an example device architecture 2500 for implementing the features and processes described in reference to FIGS. 1-36. For example, the architecture 3700 can be used to implement the mobile device 102, the server computer system 104, and/or one or more of the communications devices 106. Architecture 3700 may be implemented in any device for generating the features described in reference to FIGS. 1-36, including but not limited to desktop computers, server computers, portable computers, smart phones, tablet computers, game consoles, wearable computers, set top boxes, media players, smart TVs, and the like.

The architecture 3700 can include a memory interface 3702, one or more data processor 3704, one or more data co-processors 3774, and a peripherals interface 3706. The memory interface 3702, the processor(s) 3704, the co-processor(s) 3774, and/or the peripherals interface 3706 can be separate components or can be integrated in one or more integrated circuits. One or more communication buses or signal lines may couple the various components.

The processor(s) 3704 and/or the co-processor(s) 3774 can operate in conjunction to perform the operations described herein. For instance, the processor(s) 3704 can include one or more central processing units (CPUs) that are configured to function as the primary computer processors for the architecture 3700. As an example, the processor(s) 3704 can be configured to perform generalized data processing tasks of the architecture 3700. Further, at least some of the data processing tasks can be offloaded to the co-processor(s) 3774. For example, specialized data processing tasks, such as processing motion data, processing image data, encrypting data, and/or performing certain types of arithmetic operations, can be offloaded to one or more specialized co-processor(s) 3774 for handling those tasks. In some cases, the processor(s) 3704 can be relatively more powerful than the co-processor(s) 3774 and/or can consume more power than the co-processor(s) 3774. This can be useful, for example, as it enables the processor(s) 3704 to handle generalized tasks quickly, while also offloading certain other tasks to co-processor(s) 3774 that may perform those tasks more efficiency and/or more effectively. In some cases, a co-processor(s) can include one or more sensors or other components (e.g., as described herein), and can be configured to process data obtained using those sensors or components, and provide the processed data to the processor(s) 3704 for further analysis.

Sensors, devices, and subsystems can be coupled to peripherals interface 3706 to facilitate multiple functionalities. For example, a motion sensor 3710, a light sensor 3712, and a proximity sensor 3714 can be coupled to the peripherals interface 3706 to facilitate orientation, lighting, and proximity functions of the architecture 3700. For example, in some implementations, a light sensor 3712 can be utilized to facilitate adjusting the brightness of a touch surface 3746. In some implementations, a motion sensor 3710 can be utilized to detect movement and orientation of the device. For example, the motion sensor 3710 can include one or more accelerometers (e.g., to measure the acceleration experienced by the motion sensor 3710 and/or the architecture 3700 over a period of time), and/or one or more compasses or gyros (e.g., to measure the orientation of the motion sensor 3710 and/or the mobile device). In some cases, the measurement information obtained by the motion sensor 3710 can be in the form of one or more a time-varying signals (e.g., a time-varying plot of an acceleration and/or an orientation over a period of time). Further, display objects or media may be presented according to a detected orientation (e.g., according to a "portrait" orientation or a "landscape" orientation). In some cases, a motion sensor 3710 can be directly integrated into a co-processor 3774 configured to processes measurements obtained by the motion sensor 3710. For example, a co-processor 3774 can include one or more accelerometers, compasses, and/or gyroscopes, and can be configured to obtain sensor data from each of these sensors, process the sensor data, and transmit the processed data to the processor(s) 3704 for further analysis.

Other sensors may also be connected to the peripherals interface 3706, such as a temperature sensor, a biometric sensor, or other sensing device, to facilitate related functionalities. As an example, as shown in FIG. 37, the architecture 3700 can include a heart rate sensor 3732 that measures the beats of a user's heart. Similarly, these other sensors also can be directly integrated into one or more co-processor(s) 3774 configured to process measurements obtained from those sensors.

A location processor 3715 (e.g., a GNSS receiver chip) can be connected to the peripherals interface 3706 to provide geo-referencing. An electronic magnetometer 3716 (e.g., an integrated circuit chip) can also be connected to the peripherals interface 3706 to provide data that may be used to determine the direction of magnetic North. Thus, the electronic magnetometer 3716 can be used as an electronic compass.

A camera subsystem 3720 and an optical sensor 3722 (e.g., a charged coupled device [CCD] or a complementary metal-oxide semiconductor [CMOS] optical sensor) can be utilized to facilitate camera functions, such as recording photographs and video clips.

Communication functions may be facilitated through one or more communication subsystems 3724. The communication subsystem(s) 3724 can include one or more wireless and/or wired communication subsystems. For example, wireless communication subsystems can include radio frequency receivers and transmitters and/or optical (e.g., infrared) receivers and transmitters. As another example, wired communication system can include a port device, e.g., a Universal Serial Bus (USB) port or some other wired port connection that can be used to establish a wired connection to other computing devices, such as other communication devices, network access devices, a personal computer, a printer, a display screen, or other processing devices capable of receiving or transmitting data.

The specific design and implementation of the communication subsystem 3724 can depend on the communication network(s) or medium(s) over which the architecture 3700 is intended to operate. For example, the architecture 3700 can include wireless communication subsystems designed to operate over a global system for mobile communications (GSM) network, a GPRS network, an enhanced data GSM environment (EDGE) network, 802.x communication networks (e.g., Wi-Fi, Wi-Max), code division multiple access (CDMA) networks, NFC and a Bluetooth™ network. The wireless communication subsystems can also include hosting protocols such that the architecture 3700 can be configured as a base station for other wireless devices. As another example, the communication subsystems may allow the architecture 3700 to synchronize with a host device using one or more protocols, such as, for example, the TCP/IP protocol, HTTP protocol, UDP protocol, and any other known protocol.

An audio subsystem 3726 can be coupled to a speaker 3728 and one or more microphones 3730 to facilitate voice-enabled functions, such as voice recognition, voice replication, digital recording, and telephony functions.

An I/O subsystem 3740 can include a touch controller 3742 and/or other input controller(s) 3744. The touch controller 3742 can be coupled to a touch surface 3746. The touch surface 3746 and the touch controller 3742 can, for example, detect contact and movement or break thereof using any of a number of touch sensitivity technologies, including but not limited to capacitive, resistive, infrared, and surface acoustic wave technologies, as well as other proximity sensor arrays or other elements for determining one or more points of contact with the touch surface 3746. In one implementation, the touch surface 3746 can display virtual or soft buttons and a virtual keyboard, which can be used as an input/output device by the user.

Other input controller(s) 3744 can be coupled to other input/control devices 3748, such as one or more buttons, rocker switches, thumb-wheel, infrared port, USB port, and/or a pointer device such as a stylus. The one or more buttons (not shown) can include an up/down button for volume control of the speaker 3728 and/or the microphone 3730.

In some implementations, the architecture 3700 can present recorded audio and/or video files, such as MP3, AAC, and MPEG video files. In some implementations, the architecture 3700 can include the functionality of an MP3 player and may include a pin connector for tethering to other devices. Other input/output and control devices may be used.

A memory interface 3702 can be coupled to a memory 3750. The memory 3750 can include high-speed random access memory or non-volatile memory, such as one or more magnetic disk storage devices, one or more optical storage devices, or flash memory (e.g., NAND, NOR). The memory 3750 can store an operating system 3752, such as Darwin, RTXC, LINUX, UNIX, OS X, WINDOWS, or an embedded operating system such as VxWorks. The operating system 3752 can include instructions for handling basic system services and for performing hardware dependent tasks. In some implementations, the operating system 3752 can include a kernel (e.g., UNIX kernel).

The memory 3750 can also store communication instructions 3754 to facilitate communicating with one or more additional devices, one or more computers or servers, including peer-to-peer communications. The communication instructions 3754 can also be used to select an operational mode or communication medium for use by the device, based on a geographic location (obtained by the GPS/Navigation instructions 3768) of the device. The memory 3750 can include graphical user interface instructions 3756 to facilitate graphic user interface processing, including a touch model for interpreting touch inputs and gestures; sensor processing instructions 3758 to facilitate sensor-related processing and functions; phone instructions 3760 to facilitate phone-related processes and functions; electronic messaging instructions 3762 to facilitate electronic-messaging related processes and functions; web browsing instructions 3764 to facilitate web browsing-related processes and functions; media processing instructions 3766 to facilitate media processing-related processes and functions; GPS/Navigation instructions 3769 to facilitate GPS and navigation-related processes; camera instructions 3770 to facilitate camera-related processes and functions; and other instructions 3772 for performing some or all of the processes described herein.

Each of the above identified instructions and applications can correspond to a set of instructions for performing one or more functions described herein. These instructions need not be implemented as separate software programs, procedures, or modules. The memory 3750 can include additional instructions or fewer instructions. Furthermore, various functions of the device may be implemented in hardware and/or in software, including in one or more signal processing and/or application specific integrated circuits (ASICs).

The features described may be implemented in digital electronic circuitry or in computer hardware, firmware, software, or in combinations of them. The features may be implemented in a computer program product tangibly embodied in an information carrier, e.g., in a machine-readable storage device, for execution by a programmable processor; and method steps may be performed by a programmable processor executing a program of instructions to perform functions of the described implementations by operating on input data and generating output.

The described features may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., Objective-C, Java), including compiled or interpreted languages, and it may be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer may communicate with mass storage devices for storing data files. These mass storage devices may include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

To provide for interaction with a user the features may be implemented on a computer having a display device such as a CRT (cathode ray tube) or LCD (liquid crystal display) monitor for displaying information to the author and a keyboard and a pointing device such as a mouse or a trackball by which the author may provide input to the computer.

The features may be implemented in a computer system that includes a back-end component, such as a data server or that includes a middleware component, such as an application server or an Internet server, or that includes a front-end component, such as a client computer having a graphical user interface or an Internet browser, or any combination of them. The components of the system may be connected by any form or medium of digital data communication such as a communication network. Examples of communication networks include a LAN, a WAN and the computers and networks forming the Internet.

The computer system may include clients and servers. A client and server are generally remote from each other and typically interact through a network. The relationship of client and server arises by virtue of computer programs running on the respective computers and having a client-server relationship to each other.

One or more features or steps of the disclosed embodiments may be implemented using an Application Programming Interface (API). An API may define on or more parameters that are passed between a calling application and other software code (e.g., an operating system, library routine, function) that provides a service, that provides data, or that performs an operation or a computation.

The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer will employ to access functions supporting the API.

In some implementations, an API call may report to an application the capabilities of a device running the application, such as input capability, output capability, processing capability, power capability, communications capability, etc.

As described above, some aspects of the subject matter of this specification include gathering and use of data available from various sources to improve services a mobile device can provide to a user. The present disclosure contemplates that in some instances, this gathered data may identify a particular location or an address based on device usage.

Such personal information data can include location-based data, addresses, subscriber account identifiers, or other identifying information.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

In the case of advertisement delivery services, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

A number of implementations have been described. Nevertheless, it will be understood that various modifications may be made. Elements of one or more implementations may be combined, deleted, modified, or supplemented to form further implementations. As yet another example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A method comprising:
   receiving, by a mobile device, motion data obtained by one or more sensors worn by a user;
   determining, by the mobile device, and based on the motion data, that the user experienced an impact;
   determining, by the mobile device, and based on the motion data, that the user performed a first wrist motion prior to the impact; and
   determining, by the mobile device, that the user has fallen based on the determination that the user experienced the impact and the determination that the user performed the first wrist motion prior to the impact.

2. The method of claim 1, wherein the first wrist motion comprises a bracing motion by the wrist.

3. The method of claim 2, wherein determining that the user performed the bracing motion comprises determining that the user moved the wrist outward from a body of the user.

4. The method of claim 1, wherein the first wrist motion comprises to a flailing motion by the wrist.

5. The method of claim 4, wherein determining that the user performed the flailing motion comprises determining an orientation of the wrist over time.

6. The method of claim 5, wherein determining that the user performed the flailing motion comprises determining a variation of the orientation of the wrist over time.

7. The method of claim 5, wherein determining that the user performed the flailing motion comprises determining the user reversed a motion of the wrist one or more times.

8. The method of claim 1, wherein the first wrist motion comprises a balancing motion by the wrist.

9. The method of claim 8, wherein determining that the user performed the balancing motion comprises determining the user moved the wrist along a positive arc length.

10. The method of claim 1, wherein the mobile device is a wearable mobile device.

11. The method of claim 1, wherein at least some of the one or more sensors are disposed on or in the mobile device.

12. The method of claim 1, wherein at least some of the one or more sensors are remote from the mobile device.

13. A system comprising:
   one or more processors; and
   one or more non-transitory computer readable media storing instructions that, when executed by the one or more processors, cause the one or more processors to perform operations comprising:
   receiving motion data obtained by one or more sensors worn by a user;
   determining, based on the motion data, that the user experienced an impact;
   determining, based on the motion data, that the user performed a first wrist motion prior to the impact; and
   determining that the user has fallen based on the determination that the user experienced the impact and the determination that the user performed the first wrist motion prior to the impact.

14. The system of claim 13, wherein the first wrist motion comprises a bracing motion by the wrist.

15. The system of claim 13, wherein the first wrist motion comprises to a flailing motion by the wrist.

16. The system of claim 13, wherein the first wrist motion comprises a balancing motion by the wrist.

17. The system of claim 13, wherein the system comprises a wearable mobile device.

18. The system of claim 17, wherein at least some of the one or more sensors are disposed on or in the wearable mobile device.

19. The system of claim 17, wherein at least some of the one or more sensors are remote from the wearable mobile device.

20. One or more non-transitory computer readable media storing instructions that, when executed by one or more processors, cause the one or more processors to perform operations comprising:
- receiving motion data obtained by one or more sensors worn by a user;
- determining, based on the motion data, that the user experienced an impact;
- determining, based on the motion data, that the user performed a first wrist motion prior to the impact; and
- determining that the user has fallen based on the determination that the user experienced the impact and the determination that the user performed the first wrist motion prior to the impact.

* * * * *